(12) United States Patent
Pekari et al.

(10) Patent No.: US 7,714,134 B2
(45) Date of Patent: May 11, 2010

(54) COMPOUNDS AND USE OF TETRAHYDROPYRIDOTHIOPHENES

(75) Inventors: Klaus Pekari, Radolfzell (DE); Thomas Baer, Reichenau (DE); Mathias Schmidt, Konstanz (DE); Thomas Beckers, Konstanz (DE)

(73) Assignee: 4SC AG, Planegg Martinsrid (DE)

( * ) Notice: Subject to any disclaimer, the term of this patent is extended or adjusted under 35 U.S.C. 154(b) by 48 days.

(21) Appl. No.: 11/628,369

(22) PCT Filed: Jun. 10, 2005

(86) PCT No.: PCT/EP2005/052693

§ 371 (c)(1),
(2), (4) Date: Dec. 4, 2006

(87) PCT Pub. No.: WO2005/120642

PCT Pub. Date: Dec. 22, 2005

(65) Prior Publication Data

US 2007/0259911 A1 Nov. 8, 2007

(30) Foreign Application Priority Data

Jun. 11, 2004 (EP) .................................. 04102662
Feb. 23, 2005 (EP) .................................. 05101381

(51) Int. Cl.
*C07D 471/02* (2006.01)
(52) U.S. Cl. ..................................................... 546/114
(58) Field of Classification Search .................. 546/114
See application file for complete search history.

(56) References Cited

U.S. PATENT DOCUMENTS

| | | | |
|---|---|---|---|
| 3,449,439 A | 6/1969 | Kuhnen et al. | |
| 4,963,559 A | 10/1990 | Suzuki | |
| 5,422,335 A | 6/1995 | Hagen et al. | |
| 6,069,620 A | 5/2000 | Nakamura et al. | |
| 2003/0218593 A1 | 11/2003 | Inoue et al. | |
| 2003/0232994 A1 | 12/2003 | Lu et al. | |
| 2004/0171603 A1 | 9/2004 | Pato et al. | |
| 2004/0209943 A1* | 10/2004 | Erickson et al. | 514/444 |
| 2005/0154024 A1 | 7/2005 | Bryans | |

FOREIGN PATENT DOCUMENTS

| | | |
|---|---|---|
| DE | 272 078 A1 | 9/1989 |
| DE | 40 39 734 A1 | 6/1992 |
| WO | WO 9427969 | 12/1994 |
| WO | 98/02440 A1 | 1/1998 |
| WO | 99/46267 A1 | 9/1999 |
| WO | WO 0014090 | 3/2000 |
| WO | WO 0247762 | 6/2002 |
| WO | 02/092076 A1 | 11/2002 |
| WO | WO 03080607 | 10/2003 |
| WO | WO 03084947 | 10/2003 |
| WO | WO 03102153 | 12/2003 |
| WO | 2004/024065 A2 | 3/2004 |
| WO | 2004/024066 A2 | 3/2004 |
| WO | 2004/069149 A2 | 8/2004 |
| WO | WO 2004/065351 | 8/2004 |
| WO | 2004/092156 A1 | 10/2004 |
| WO | WO 2005023818 | 3/2005 |
| WO | 2005/033102 A2 | 4/2005 |
| WO | WO 2005030770 | 4/2005 |
| WO | 2005/044008 A2 | 5/2005 |
| WO | 2005/060711 A2 | 7/2005 |
| WO | 2005/118071 A2 | 12/2005 |
| WO | 2005/118592 A1 | 12/2005 |
| WO | WO 2005/120642 | 12/2005 |
| WO | WO 2006/014135 | 2/2006 |
| WO | WO 2006/084869 | 8/2006 |
| WO | WO 2006/084904 | 8/2006 |
| WO | WO 2006/125813 | 11/2006 |
| WO | WO 2006/125815 | 11/2006 |
| WO | WO 2008020045 | 12/2007 |

OTHER PUBLICATIONS

Bioorganic & Medicinal Chemistry Letters (2002), 12, 1897-1900.*
Database Chemcats, Chemical Abstracts Service, Columbus, Ohio, US; XP002303659; abstract & "Ambinter Screening Library", Jan. 1, 2004.
Database Chemcats, Chemical Abstracts Service, Columbus, Ohio, US; XP002369767; abstract * "Interchim Intermediates", Jan. 18, 2005.
Database Chemcats, Chemical Abstracts Service, Columbus, Ohio, US; XP002369768; abstract & "Ambinter Stock Screening Collection", Jul. 3, 2005.
Database Chemcats, Chemical Abstracts Service, Columbus, Ohio, US; XP002361378; abstract & "Interchim Intermediates", Jan. 18, 2005.
Database Chemcats, Chemical Abstracts Service, Columbus, Ohio, US; XP002303660; abstract & "TimTec Overseas Stock", Jun. 1, 2004.
Database Chemcats, Chemical Abstracts Service, Columbus, Ohio, US; XP002361377; abstract & "Ambinter Screening Library", Jan. 1, 2004.

(Continued)

*Primary Examiner*—D. Margaret Seaman
*Assistant Examiner*—Nizal S Chandrakumar
(74) *Attorney, Agent, or Firm*—Millen, White, Zelano & Branigan, P.C.

(57) ABSTRACT

The compounds of a certain formula (1)

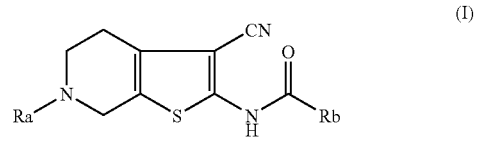

(I)

in which Ra and Rb have the meanings indicated in the description are novel for treating hyperproliferative diseases and/or disorders responsive to the induction of apoptosis. The invention further relates to certain compounds of formula (I), in which Ra and Rb have the meanings indicated in the description.

24 Claims, No Drawings

OTHER PUBLICATIONS

Ashimori et al., "Novel 1,4-Dihydropyridine Calcium Antagonists. I. Synthesis and Hypotensive Activity of 4-(Substituted Pyridel)-1,4-dihydropyridine Derivatives." Chem. Pharm. Bull., v.38(9), pp. 2446-2458, 1990.

Srikrishna et al., "A simple Strategy for Spirocyclopentannulation of Cyclic Ketones. Formal Total Synthesis of (±)-Acorone." *Tetrahedron Letters* v.37(10), pp. 1683-1686, 1996.

Uemura et al., "Highly Efficient Enantioselective Synthesis of Optically Active Carboxylic Acids by RU $(OCOCH_3)_2[(S)-H_8-BINAP]$." *J. Org. Chem.*, v.61, pp. 5510-5516, 1996.

Database Chemcats, Columbus, Ohio, U.S., XP 002377744, 2 pages. Chemical Abstracts, CAS RN 724704-04-5 CAS RN 724704-02-3 XP 002336416, 10 pages.

Fujita, M. et al., "Synthesis and Bioactivities of Novel Bicyclic Thiophenes and 4,5,6,7-Tetrahydrothieno[2,3-c]pyridines as Inhibitors of Tumor Necrosis Factor-alpha (TNF-alpha) Production," Bioorganic & Medicinal Chemistry Letters, vol. 12, pp. 1897-1900 (2002).

Sensfuss, U. et al., "2-Aminothiophenes from Triacetonamine: A Convenient Way to Novel Sterically Hindered Piperidine Derivatives," Heteroatom Chemistry, vol. 9, No. 6, pp. 529-536 (1998).

Sensfuss, U. et al., "An unusual Cascade Reaction Yielding Ortho-Peri-Fused Thienopyridopyrimidines," Heterocycles, vol. 55, No. 1, pp. 171-180 (2001).

Castanedo, G. and Sutherlin, D. "Synthesis of tetrasubstituted thiphenes on solid-support using the Gewald reaction," Tetrahedron Letters, vol. 42, pp. 7181-7184 (2001).

Charette, A. Janes, M. Lebel, H., "Bis(oxazoline) copper(I)-catalyzed enantioselective cyclopropanation of cinnamate esters with diazomethane," Tetrahedron: Asymmetry, vol. 14, pp. 867-872 (2003).

Ezquerra, J., Prieto, L., Avendano, C., Martos, J., And de la Cuesta, E., "Asymmetric Michael Addition Reactions Using Ethyl (S)-4,4-Dimethylpyroglutamate as a Chiral Auxiliary," Tetrahedron Letters, vol. 40, pp. 1575-1578 (1999).

Huang, K., Huang, Z., "A practical and Controllable Enantioselective Synthesis of 2-Phenyl-cyclopropanecarboxylates via a Camphor-Derived Sulfonium Ylide," Synlett, No. 10, pp. 1621-1623 (2005).

Lipshutz, B., Servesko, J., and Taft, B., "Asymmetric 1,4-Hydrosilylations of alpha, beta-Unsaturated Esters," J. Am. Chem. Soc., vol. 126, pp. 8352-8353 (2004).

Lyle, M., Wilson, P., "Synthesis of a New Chiral Nonracemic C2-Symmetric 2,2'-Bipyridyl Ligand and Its Application in Copper (I)-Catalyzed Enantioselective Cyclopropanation Reactions," Organic Letters, vol. 6, No. 5, pp. 855-857.

Sakuma, S., Sakai, M, Itooka, R., and Miyaura, N. "Asymmetric Conjugate 1,4-Addition of Arylboronic Acids to alpha, beta-Unsaturated Esters Catalyzed by Rhodium(I)(S)-binap," J. Org. Chem., vol. 65, pp. 5951-5955 (2000).

Lindstedt, E. and Nilsson, M., "2-Thienyl as Auxiliary Group in Mixed Lithium Diorganocuprates," Acta Chemica Scandinavica, B 40, pp. 466-469 (1986).

Sainsbury, M., Weerasinghe, D., and Dolman, D., Chemistry of 6H-pyridol[4,3-b]carbazoles, Part 9. An Efficient route to 3-[1-(3-Ethylpyridyl)] indoles and the Synthesis of Some New Ellipticines. J.C.S. Perkin I, pp. 587-590.

Tang, W., Wang, W., and Zhang, X., "Phospholane-Oxazoline Ligands for Ir-Catalyzed Asymmetric Hydrogenation," Angew. Chem. Int. Ed., vol. 42, No. 8, pp. 943-946 (2003).

Sep. 3, 2007—SciFinder pp. 1 and 2.

Chemcats, Interchim Intermediates—XP-002361378— "Thieno{2,3-c]pyridine-6(5H)-carboxylic acid, 2-[(3-chlorobenzoyl)amino]-3-cyano-4,7-dihydroethyl ester" pp. 1-5.

Non-Final Office Action dated Jun. 19, 2008 in related U.S. Appl. No. 11/597,556 filed Nov. 26, 2007. (US-2007-0213360-A1).

Non-Final Office Action dated Oct. 8, 2008 in related U.S. Appl. No. 11/883,596 filed Sep. 17, 2007. (US-2008-0096914-A1).

Non-Final Office Action dated Oct. 8, 2008 in related U.S. Appl. No. 11/628,369 filed Dec. 4, 2006. (US-2007-0259911-A1).

Non-Final Office Action dated Jun. 25, 2008 in related U.S. Appl. No. 11/597,142 filed Nov. 20, 2006. (US-2007-0244112-A1).

Non-Final Office Action dated Jun. 3, 2009 in related U.S. Appl. No. 12/411,486, filed Mar. 26, 2009.

Non-Final Office Action dated Jun. 4, 2009 in related U.S. Appl. No. 12/390,827, filed Feb. 23, 2009.

\* cited by examiner

COMPOUNDS AND USE OF TETRAHYDROPYRIDOTHIOPHENES

This application was filed under 35 U.S.C. 371 as a national stage of PCT/EP2005/052693, filed Jun. 10, 2005.

FIELD OF APPLICATION OF THE INVENTION

The invention relates to the contribution made to the art by the finding, that arylamido-substituted tetrahydropyridothiophene derivatives display cell-cycle dependent, anti-proliferative and apoptosis inducing activity.

The invention further relates to certain arylamido-substituted tetrahydropyridothiophene derivatives, which can be used in the pharmaceutical industry for the production of pharmaceutical compositions.

The invention also relates to the use of arylamido-substituted tetrahydropyridothiophene derivatives for the therapy of hyperproliferative diseases, in particular human cancer.

KNOWN TECHNICAL BACKGROUND

Cancer chemotherapy was established with the alkylating agent Cyclophosphamide (Endoxan®), an oxazaphosphorin pro-drug activated preferentially in the tumor. The target of alkylating agents like Cyclophosphamide is DNA and the concept, that cancer cells with uncontrolled proliferation and a high mitotic index are killed preferentially, proved to be very sucessfull. Standard cancer chemotherapeutic drugs finally kill cancer cells upon induction of programmed cell death ("apoptosis") by targeting basic cellular processes and molecules. These basic cellular processes and molecules include RNA/DNA (alkylating and carbamylating agents, platin analogs and topoisomerase inhibitors), metabolism (drugs of this class are named anti-metabolites and examples are folic acid, purin and pyrimidine antagonist) as well as the mitotic spindle apparatus with ($\alpha$, $\beta$-tubulin heterodimers as the essential component (drugs are categorized into stabilizing and destabilizing tubulin inhibitors; examples are Taxol/Paclitaxel®, Docetaxel/Taxotere® and vinca alkaloids).

A subgroup of proapoptotic anticancer agents target cells preferentially in mitosis. In general these agents do not induce apoptosis in non-dividing cells, arrested in the G0, G1 or G2 phase of the cell division cycle. In contrast, dividing cells going through mitosis (M-phase of the cell division cycle), are killed efficiently by induction of apoptosis by this subgroup agents. Therefore, this subgroup or class of anti-cancer agents is described as cell-cycle specific or cell-cycle dependent. Tubulin inhibitors, with Taxol (Paclitaxel®) as a prominent example, belong to this class of cell-cycle specific, apoptosis inducing anti-cancer agents.

PRIOR ART

The international application WO2004/024065 mentions, inter alia, arylamido-substituted tetrahydropyridothiophene derivatives as glucagons antagonists for the treatment of diabetes.

The international application WO2004/024066 mentions, inter alia, arylamido-substituted tetrahydrobenzothiophene derivatives as glucagons antagonists for the treatment of diabetes.

The german document DE4039734 describes, inter alia, N-alkylated tetrahydropyridothiophene derivatives as components of herbicidal agents.

The german document DD272078 describes, inter alia, N-alkylated tetrahydropyridothiophene derivatives with anti-anaphylactic und antihistaminergic properties.

The international application WO2005/033102 describes thiophene-based compounds exhibiting ATP-utilizing enzyme inhibitory activity.

DESCRIPTION OF THE INVENTION

Surprisingly and unanticipatedly, it has now been found that the arylamido-substituted tetrahydropyridothiophene derivatives, which are described in greater details below, are potent and highly efficacious inhibitors of cellular (hyper) proliferation and/or inducers of apoptosis in cancer cells. Therefore, yet unanticipatedly, these tetrahydropyridothiophene derivatives are useful for treating hyperproliferative diseases and/or disorders responsive to the induction of apoptosis, in particular cancer. By having a cell-cycle specific mode of action, these tetrahydropyridothiophene derivates should have a higher therapeutic index compared to standard chemotherapeutic drugs targeting basic cellular processes like DNA replication or interfering with basic cellular molecules like DNA.

Accordingly, it has also been found that certain arylamido-substituted tetrahydropyridothiophene derivatives, which are also described in greater details below, differ from prior art compounds by unanticipated and originative structural features, and have surprising and particularly advantageous properties. Thus, for example, those -compounds according to this invention are potent and highly efficacious inhibitors of cellular (hyper)proliferation and/or cell-cycle specific inducers of apoptosis in cancer cells. Therefore, unanticipatedly, these compounds can be useful for treating (hyper)proliferative diseases and/or disorders responsive to the induction of apoptosis, in particular cancer. By having a cell-cycle specific mode of action, these derivates should have a higher therapeutic index compared to standard chemotherapeutic drugs targeting basic cellular processes like DNA replication or interfering with basic cellular molecules like DNA. Thus, for example, those compounds according to this invention are expected to be useful in targeted cancer therapy.

Yet accordingly, it has also been found, that certain purposively selected arylamido-substituted tetrahydropyridothiophene derivatives, which are also described in greater details below, are clearly distinguishable from compounds mentioned generically in prior art by specific, unanticipated and originative combination of divers structural elements and differ profoundly from previously individualized compounds, and have surprising and particularly advantageous properties, such as e.g. those mentioned above.

The invention thus relates in a first aspect (aspect 1) to the use of compounds of formula I

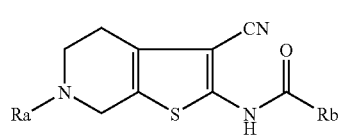

wherein
Ra is —C(O)R1, —C(O)OR2, —C(O)SR2, —C(O)N(R3) R4, —S(O)$_2$R1, or —S(O)$_2$N(R3)R4; and
Rb is optionally substituted by Rba and/or Rbb and/or Rbc, and is aryl, in which aryl is phenyl, or naphthyl;

in which
R1, R2 and R3 may be the same or different and are independently selected from the group consisting of: hydrogen, 1-7C-alkyl, 3-7C-cycloalkyl, Ar, Har and Het, wherein each of said 1-7C-alkyl, 3-7C-cycloalkyl, Ar, Har and Het can be unsubstituted or optionally substituted by at least one substituent independently selected from R5;

each R4 is independently selected from the group consisting of: hydrogen, 1-7C-alkyl, and 3-7C-cycloalkyl, wherein each of said 1-7C-alkyl and 3-7C-cycloalkyl can be unsubstituted or optionally substituted by at least one substituent independently selected from R5;

R5, Rba, Rbb and Rbc may be the same or different and are independently selected from the group consisting of:
1-7C-alkyl, 3-7C-cycloalkyl, Ar, Har, Het, halogen, trifluoromethyl, nitro, cyano, guanidino, amidino,
—C(O)R6, —C(O)OR7, —C(O)N(R8)R9, —S(O)$_2$R6, —S(O)$_2$N(R8)R9,
—N(R10)C(O)R6, —N(R10)C(O)OR7, —N(R10)C(O)N(R8)R9, —N(R10)S(O)$_2$R6,
—N(R10)S(O)$_2$N(R8)R9,
—OC(O)R6, —OC(O)N(R8)R9,
—OR7, —N(R8)R(9), and —SR7, wherein each of said 1-7C-alkyl, 3-7C-cycloalkyl, Ar, Har and Het can be unsubstituted or optionally substituted by at least one substituent independently selected from R11;

R6, R7 and R8 may be the same or different and are independently selected from the group consisting of: hydrogen, 1-7C-alkyl, 3-7C-cycloalkyl, Ar, Har and Het, wherein each of said 1-7C-alkyl, 3-7C-cycloalkyl, Ar, Har and Het can be unsubstituted or optionally substituted by at least one substituent independently selected from R12;

each R9 is independently selected from the group consisting of: hydrogen, 1-7C-alkyl, and 3-7C-cycloalkyl, wherein each of said 1-7C-alkyl and 3-7C-cycloalkyl can be unsubstituted or optionally substituted by at least one substituent independently selected from R12;

each R10 is independently selected from the group consisting of: hydrogen, 1-7C-alkyl, and 3-7C-cycloalkyl;

R11 is selected from the group consisting of: R5 as defined above;

each R12 is independently selected from the group consisting of: R5 as defined above;

each Ar is independently selected from phenyl and naphthyl;

each Har is independently any fully aromatic or partially aromatic mono- or fused bicyclic ring or ring system made up of a first constituent being a 5- or 6-membered monocyclic unsaturated, aromatic heteroaryl ring A, which heteroaryl ring A comprises one to four heteroatoms independently selected from nitrogen, oxygen and sulfur, and, optionally, fused to said first constituent, a second constituent being a benzo group, any 3-7C-cycloalkane group as defined herein, any additional heteroaryl ring A as defined herein afore, or any heterocyclic ring B as defined herein below, whereby said Har ring or ring system is attached to the parent molecular group via a substitutable ring carbon or ring nitrogen atom;

each Het is independently any fully saturated or partially unsaturated mono- or fused bicyclic ring or ring system made up of a first constituent being a 3- or 7-membered monocyclic fully saturated or partially unsaturated, non-aromatic heterocyclic ring B, which heterocyclic ring B comprises one to three heteroatoms independently selected from nitrogen, oxygen and sulfur, and which heterocyclic ring B is optionally substituted by one or two oxo groups, and, optionally, fused to said first constituent, a second constituent being a benzo group, any 3-7C-cycloalkane group as defined herein, or any additional heterocyclic ring B as defined herein afore, whereby said Het ring or ring system is attached to the parent molecular group via a substitutable ring carbon or ring nitrogen atom;

and the salts, solvates or the solvates of the salts thereof;

for the manufacture of pharmaceutical compositions for the treatment, prevention or amelioration of hyperproliferative diseases of benign or malignant behaviour, such as e.g. cancer, and/or disorders responsive to the induction of apoptosis in a mammal.

As used herein, "alkyl" refers to both branched and straight chain saturated aliphatic hydrocarbon groups having the specified numbers of carbon atoms, such as for example:

1-4C-Alkyl is a straight-chain or branched alkyl radical having 1 to 4 carbon atoms. Examples are the butyl, isobutyl, sec-butyl, tert-butyl, propyl, isopropyl, and particularly the ethyl and methyl radicals.

1-7C-Alkyl is a straight-chain or branched alkyl radical having 1 to 7 carbon atoms. Examples are the heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, propyl, isopropyl, ethyl and methyl radicals. An embodiment of 1-7C-alkyl, 1-6C-alkyl or 1-5C-alkyl refers to 1-4C-alkyl, such as e.g. methyl, ethyl, propyl or butyl.

One notable embodiment of herein-mentioned "alkyl" having the specified numbers of carbon atoms refers to the straight-chain radicals thereof.

3-7C-Cycloalkyl stands for cyclopropyl, cyclobutyl, cyclopentyl, cyclohexyl and cycloheptyl, of which cyclopropyl and cyclopentyl are to be emphasized.

3-7C-Cycloalkane stands for cyclopropane, cyclobutane, cyclopentane, cyclohexane and cycloheptane, of which cyclohexane and cyclopentane are to be emphasized.

3-7C-Cycloalkyl-1-4C-alkyl stands for one of the abovementioned 1-4C-alkyl radicals, which is substituted by one of the abovementioned 3-7C-cycloalkyl radicals. Examples which may be mentioned are the 3-7C-cycloalkylmethyl radicals (such as e.g. cyclopropylmethyl or cyclohexylmethyl) and the cyclohexylethyl radical.

Halogen within the meaning of the present invention is iodine, or, particularly, bromine, chlorine or fluorine.

1-4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radicals.

2-4C-Alkoxy represents radicals which, in addition to the oxygen atom, contain a straight-chain or branched alkyl radical having 2 to 4 carbon atoms. Examples which may be mentioned are the butoxy, isobutoxy, sec-butoxy, tert-butoxy, propoxy, isopropoxy and preferably the ethoxy radical.

1-4C-Alkoxy-2AC-alkoxy stands for one of the abovementioned 2-4C-alkoxy radicals which is substituted by one of the abovementioned 1-4C-alkoxy radicals. Examples which may be mentioned are the 2-(methoxy)ethoxy (—O—$CH_2$—$CH_2$—O—$CH_3$), the 2-(ethoxy)ethoxy (—O—$CH_2$—$CH_2$—O—$CH_2$—$CH_3$), and the 2-(isopropoxy)ethoxy radical.

Phenyl-1-4C-alkoxy represents one of the abovementioned 1-4C-alkoxy radicals, which is substituted by a phenyl radical. Examples which may be mentioned are the phenethoxy and the benzyloxy radicals.

Pyridyl-1-4C-alkoxy represents one of the abovementioned 1-4C-alkoxy radicals, which is substituted by a pyridyl radical. Examples which may be mentioned are the 2-pyridylethoxy and the pyridylmethoxy radicals.

Pyridyl includes pyridin-2-yl, pyridin-3-yl and pyridin-4-yl.

3-7C-Cycloalkoxy stands for cyclopropyloxy, cyclobutyloxy, cyclopentyloxy, cyclohexyloxy or cycloheptyloxy, of which cyclopropyloxy and cyclopentyloxy are preferred.

3-7C-Cycloalkyl-1-4C-alkoxy stands for one of the abovementioned 1-4C-alkoxy radicals, which is substituted by one of the abovementioned 3-7C-cycloalkyl radicals. Examples which may be mentioned are the 3-7C-cycloalkylmethoxy radicals (such as e.g. cyclopropylmethoxy or cyclohexylmethoxy) and the cyclohexylethoxy radical.

Completely or predominantly fluorine-substituted 1-4C-alkoxy is, for example, the 2,2,3,3,3-pentafluoropropoxy, the perfluoroethoxy, the 1,2,2-trifluoroethoxy and in particular the 1,1,2,2-tetrafluoroethoxy, the 2,2,2-trifluoroethoxy, the trifluoromethoxy and the difluoromethoxy radical, of which the difluoromethoxy radical is preferred. "Predominantly" in this connection means that more than half of the hydrogen atoms of the 1-4C-alkoxy groups are replaced by fluorine atoms.

(1-4C-Alkoxy-2-4C-alkoxy)-2-4C-alkoxy represents 2-4C-alkoxy radicals, which are substituted by one of the abovementioned 1-4C-alkoxy-2-4C-alkoxy radicals. Examples which may be mentioned are the 2-(2-methoxyethoxy)-ethoxy and the 2-(2-ethoxyethoxy)-ethoxy radicals.

Hydroxy-2-4C-alkoxy represents 2-4C-alkoxy radicals, which are substituted by a hydroxyl group. Examples which may be mentioned are the 2-hydroxyethoxy and the 3-hydroxypropoxy radicals.

1-4C-Alkylcarbonyl represents a radical which, in addition to the carbonyl group, contains one of the abovementioned 1-4C-alkyl radicals. An example which may be mentioned is the acetyl radical.

1-4C-Alkoxycarbonyl represents a radical which, in addition to the carbonyl group, contains one of the abovementioned 1-4C-alkoxy radicals. Examples which may be mentioned are the methoxycarbonyl, the ethoxycarbonyl and the tertbutoxycarbonyl radicals.

1-4C-Alkylcarbonyloxy radicals contain, in addition to the oxygen atom, one of the abovementioned 1-4C-alkylcarbonyl radicals. An example is the acetoxy radical ($CH_3C(O)$—O—).

In addition to the nitrogen atom, mono- or di-1-4C-alkylamino radicals contain one or two of the abovementioned 1-4C-alkyl radicals. Di-1-4C-alkylamino is preferred and here, in particular, dimethyl-, diethyl- or diisopropylamino.

Mono- or Di-1-4C-alkylaminocarbonyl radicals contain in addition to the carbonyl group one of the abovementioned mono- or di-1-4C-alkylamino radicals. Examples which may be mentioned are the N-methyl- the N,N-dimethyl-, the N-ethyl-, the N-propyl-, the N,N-diethyl- and the N-isopropylaminocarbonyl radical.

An 1-4C-alkylcarbonylamino radical is, for example, the propionylamino ($C_3H_7C(O)NH$—) and the acetylamino radical ($CH_3C(O)NH$—).

An 1-4C-alkylsulfonylamino radical is, for example, the propylsulfonylamino ($C_3H_7S(O)_2NH$—), the ethylsulfonylamino ($C_2H_5S(O)_2NH$—) and the methylsulfonylamino ($CH_3S(O)_2NH$—) radical.

A 3-7C-cycloalkylcarbonylamino radical is, for example, the cyclopropylcarbonylamino, the cyclopentylcarbonylamino and the cyclohexylcarbonylamino radical.

A 3-7C-cycloalkylsulfonylamino radical is, for example, the cyclopropylsulfonylamino, the cyclopentylsulfonylamino and the cyclohexylsulfonylamino radical.

As it is known fo the skilled person, the terms imidazolo, pyrazolo, piperidino or morpholino and the like stands for imidazol-1-yl, pyrazol-1-yl, piperidin-1-yl or morpholin4-yl and the like, respectively.

The term (R5)-methyl stand for methyl which is substituted by R5. The term 2-(R5)-ethyl stands for ethyl which is substituted in 2-position by R5. The term 3-(R5)-propyl stands for propyl which is substituted in 3-position by R5.

Ar stands for naphthyl or, particularly, phenyl.

Naphthyl includes naphthalen-1-yl and naphthalen-2-yl.

Har stands for a fully aromatic or partially aromatic mono- or fused bicyclic ring or ring system made up of a first constituent being a 5- or 6-membered monocyclic unsaturated, aromatic heteroaryl ring A, which heteroaryl ring A comprises one to four heteroatoms independently selected from nitrogen, oxygen and sulfur, and, optionally, fused to said first constituent, a second constituent being a benzo group, a 3-7C-cycloalkane group as defined herein, an additional heteroaryl ring A as defined herein afore, or a heterocydic ring B as defined herein below in the context of the definition of Het, whereby said Har ring or ring system is attached to the parent molecular group via a substitutable ring carbon or ring nitrogen atom of any of said constituents.

Examples for Har may include, but are not limited to, 5-membered heteroaryl radicals, such as e.g. furanyl, thiophenyl, pyrrolyl, oxazolyl, isoxazolyl, thiazolyl, isothiazolyl, imidazolyl, pyrazolyl, triazolyl, thiadiazolyl, oxadiazolyl, and 6-membered heteroaryl radicals, such as e.g. pyridinyl, pyrimidinyl, pyrazinyl or pyridazinyl, and the benzo-fused derivatives thereof such as e.g. quinazolinyl, quinoxalinyl, cinnolinyl, quinolinyl, isoquinolinyl, indolyl, isoindolyl, indazolyl, phthalazinyl, benzothiophenyl, benzofuranyl, isobenzofuranyl, benzoxazolyl, benzothiazolyl, benzimidazolyl, benzotriazolyl, benzoxadiazolyl or benzothiadiazolyl, as well as naphthyridinyl, indolizinyl or purinyl.

Het stands for a fully saturated or partially unsaturated mono- or fused bicyclic ring or ring system made up of a first constituent being a 3- or 7-membered monocyclic fully saturated or partially unsaturated, non-aromatic heterocyclic ring B,
which heterocyclic ring B comprises one to three heteroatoms independently selected from nitrogen, oxygen and sulfur,
and which heterocyclic ring B is optionally substituted by one or two oxo groups, and, optionally, fused to said first constituent, a second constituent being a benzo group, a 3-7C-cycloalkane group as defined herein, or an additional heterocyclic ring B as defined herein afore, whereby said Het ring or ring system is attached to the parent molecular group via a substitutable ring carbon or ring nitrogen atom of any of said constituents.

Examples for Het may include, but are not limited to, aziridinyl, azetidinyl, pyrrolidinyl, piperidinyl, homopiperidinyl, pyrazolidinyl, imidazolidinyl, piperazinyl, homopiperazinyl, morpholinyl or thiomorpholinyl, and the partially unsaturated derivatives thereof such as e.g. pyrrolinyl, imidazolinyl or pyrazolinyl, and the oxo substituted derivatives of the aforementioned examples such as e.g. 2-oxopyrrolidinyl, 2-oxoimidazolidinyl, 2-oxopiperidinyl, 2,5-dioxopyrrolidinyl, 2,5-dioxoimidazolidinyl, 2,6-dioxopiperidinyl, 2-oxopiperazinyl, or 5-oxo-1,4-diazepanyl, or S-oxo-thiomorpholinyl or S,S-dioxo-thiomorpholinyl, and the benzo-fused derivatives of the aforementioned examples such as e.g. indolinyl, isoindolinyl, 1,2,3,4-tetrahydroquinolinyl or 1,2,3,4-tetrahydroisoquinolinyl, as well as 1,3-benzodioxolyl, 2,3-dihydro-1,4-benzodioxinyl, 2,3-dihydrobenzothiophenyl, chromenyl, chromanyl, or 2,3-dihydrobenzofuranyl.

More detailed exemplary Het radicals include those isomers of the abovementioned examples which are attached via a ring nitrogen atom, such as e.g., without being limited to, aziridin-1-yl, azetidin-1-yl, pyrrolidin-1-yl, piperidin-1-yl, homopiperidin-1-yl, piperazin-1-yl, homopiperazin-1-yl, morpholin4-yl or thiomorpholin4-yl, or S-oxo-thiomorpholin4-yl or S,S-dioxo-thiomorpholin-4-yl.

Yet more detailed exemplary Het radicals include those isomers of the abovementioned examples which are attached via a ring carbon atom, such as e.g., without being limited to, pyrrolidin-2-yl, pyrrolidin-3-yl, piperidin-2-yl, piperidin-3-yl, piperidin4-yl or piperazin-2-yl.

As used herein, the term "oxo" forms a carbonyl moiety when attached at a carbon atom, a sulfoxide moiety when attached to a sulfur atom and a sulfonyl moiety when two of said terms are attached to a sulfur atom.

In general, unless otherwise noted, the terms "Har" and "Het" include all the possible isomeric forms thereof, particularly the positional isomers thereof. Thus, for example, the term pyridyl or pyridinyl includes pyridin-2-yl, pyridin-3-yl and pyridin4-yl.

Unless otherwise noted, constituents which are optionally substituted as stated herein, may be substituted by their substituents or parent molecular groups at any possible position.

Notably, Ar may be substituted by its substituents or parent molecular groups, unless otherwise noted, at any possible position.

Still yet notably, Har and Het may be substituted, unless otherwise noted, by their substituents or parent molecular groups as mentioned herein at any possible position, such as e.g. at any substitutable ring carbon or ring nitrogen atom.

Further notable, the moiety Rb of compounds of formula I is attached, unless otherwise noted, to the carbonyl portion of the aminocarbonyl group of the scaffold via any possible and allowed position of the Rb ring.

Thus e.g., when Rb is naphthyl, the naphthyl moiety is attached to the adjacent carbonyl group at any possible position of the naphthalene ring; such as e.g., when Rb is naphthyl, naphthalen-1-yl and naphthalen-2-yl are included.

When Rb is Rba- and/or Rbb- and/or Rbc-substituted phenyl, the substituents Rba, Rbb and/or Rbc can be attached, unless otherwise noted, in the ortho, meta or para position with respect to the binding position in which the phenyl ring is bonded to the adjacent carbonyl group, whereby an embodimental emphasis is placed on the attachement in the para or meta position.

When Rb is Rba- and/or Rbb-substituted phenyl, the substituents Rba and/or Rbb can be also attached, unless otherwise noted, in the ortho, meta or para position with respect to the binding position in which the phenyl ring is bonded to the adjacent carbonyl group, whereby an embodimental emphasis is placed on the attachement in the para or meta position, and whereby another embodimental emphasis is placed on the attachement in the para or, particularly, meta position.

Unless otherwise noted, rings containing quatemizable imino-type ring nitrogen atoms (—N=) may be preferably not quatemized on these imino-type ring nitrogen atoms by the mentioned substituents or parent molecular groups.

Unless otherwise noted, any heteroatom of a heterocyclic ring with unsatisfied valences mentioned herein is assumed to have the hydrogen atom(s) to satisfy the valences.

When any variable occurs more than one time in any constituent, each definition is independent.

The person skilled in the art is aware on account of his/her expert knowledge that certain combinations of the variable characteristics mentioned in the description of this invention lead to chemically les stable compounds. This can apply, for example, to certain compounds, in which —in a manner being disadvantageous for chemical stability—two heteroatoms (S, N or O) would directly meet or would only be separated by one carbon atom. This can also apply, for example, to certain free acid derivatives, such as e.g. certain carbamic acid derivatives containing a free carbamic acid function (N—C(O)OH). Those compounds of formula I according to this invention, in which the combination of the abovementioned variable substituents does not lead to chemically less stable compounds, are therefore preferred.

Suitable salts for compounds of formula I according to this invention—depending on substitution—are all acid addition salts or all salts with bases. Particular mention may be made of the pharmacologically tolerable inorganic and organic acids and bases customarily used in pharmacy. Those suitable are, on the one hand, water-insoluble and, particularly, water-soluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

On the other hand, salts with bases are—depending on substitution—also suitable. As examples of salts with bases are mentioned the lithium, sodium, potassium, calcium, aluminium, magnesium, titanium, ammonium, meglumine or guanidinium salts, here, too, the bases being employed in salt preparation in an equimolar quantitative ratio or one differing therefrom.

Pharmacologically intolerable salts, which can be obtained, for example, as process products during the preparation of the compounds of formula I according to this invention on an industrial scale, are converted into pharmacologically tolerable salts by processes known to the person skilled in the art.

According to expert's knowledge the compounds of formula I according to this invention as well as their salts may contain, e.g. when isolated in crystalline form, varying amounts of solvents. Included within the scope of the invention are therefore all solvates and in particular all hydrates of the compounds of formula I according to this invention as well as all solvates and in particular all hydrates of the salts of the compounds according to this invention.

In the context of this invention, the term hyperproliferation and analogous terms are used to describe aberrant/dysregulated cellular growth, a hallmark of diseases like cancer. This hyperproliferation might be caused by single or multiple cellular/molecular alterations in respective cells and can be, in context of a whole organism, of benign or malignant behaviour. The phrase inhibition of cell proliferation and analogous terms is used to denote an ability of the compound to retard the growth of and/or kill a cell contacted with that compound as compared to cells not contacted with that compound. Most preferable this inhibition of cell proliferation is 100%, meaning that proliferation of all cells is stopped and/or cells undergo programmed cell death. In some preffered embodiments the contacted cell is a neoplastic cell. A neoplastic cell is defined as a cell with aberrant cell proliferation. A benign neoplasia is described by hyperproliferation of cells, incapable of forming an aggressive, metastasizing tumor in-vivo. In contrast, a malignant neoplasia is described by cells with different cellular and biochemical abnormalities, e.g. capable of forming tumor metastasis. The aquired functional abnormalities of malignant neoplastic cells (also defined as "hallmarks of cancer") are replicative potential ("hyperproliferation"), self-sufficiency in growth signals, insensitivity to anti-growth signals, evasion from apoptosis, sustained angiogenesis and tissue invasion and metastasis.

The term inducer of apoptosis and analogous terms are used to identify a compound which excecutes programmed cell death in cells contacted with that compound. Apoptosis is defined by complex biochemical events within the contacted cell, such as the activation of cystein specific proteinases ("caspases") and the fragmentation of chromatin. Induction of apoptosis in cells contacted with the compound might not necessarily coupled with inhibition of cell proliferation. Preferably, the inhibition of cell proliferation and/or induction of apoptosis is specific to cells with aberrant cell growth (hyperproliferation). Thus, compared to cells with aberrant cell growth, normal proliferating or arrested cells are less sensitive or even insensitive to the proliferation inhibiting or apoptosis inducing activity of the compound. Finally, the term cytotoxic is used in a more general sense to identify compounds which kill cells by various mechanisms, including the induction of apoptosis/programmed cell death in a cell cycle dependent or cell-cycle independent manner.

The term cell cycle specific and analogous terms are used to identify a compound as inducing apoptosis only in continously proliferating cells actively passing a specific phase of the cell cycle, but not in resting, non-dividing cells. Continously proliferating cells are typical for diseases like cancer and characterized by cells in all phases of the cell division cycle, namely in the G ("gap") 1, S ("DNA synthesis"), G2 and M ("mitosis") phase.

In a second aspect (aspect 2), the present invention relates to those compounds of formula I, wherein Ra is —C(O)R1, or —C(O)SR2; and Rb is optionally substituted by Rba and/or Rbb and/or Rbc, and is aryl, in which aryl is phenyl, or naphthyl;

in which

R1 is selected from the group consisting of: hydrogen and 1-4C-alkyl, wherein said 1-4C-alkyl can be unsubstituted or optionally substituted by at least one substituent independently selected from R5;

R2 is selected from the group consisting of:
1-7C-alkyl, 3-7C-cycloalkyl, Ar, Har and Het, wherein each of said 1-7C-alkyl, 3-7C-cycloalkyl, Ar, Har and Het can be unsubstituted or optionally substituted by at least one substituent independently selected from R5;

R5, Rba, Rbb and Rbc may be the same or different and are independently selected from the group consisting of:
1-7C-alkyl, 3-7C-cycloalkyl, Ar, Har, Het,
halogen, trifluoromethyl, nitro, cyano, guanidino, amidino,
—C(O)R6, —C(O)OR7, —C(O)N(R8)R9, —S(O)$_2$R6,
—N(R10)C(O)R6, —N(R10)C(O)OR7, —N(R10)C(O)N(R8)R9, —N(R10)S(O)$_2$R6,
—N(R10)S(O)$_2$N(R8)R9,
—OC(O)R6, —OC(O)N(R8)R9,
—OR7, —N(R8)R(9), and —SR7, wherein each of said 1-7C-alkyl, 3-7C-cycloalkyl, Ar, Har and Het can be unsubstituted or optionally substituted by at least one substituent independently selected from R11;

R6, R7 and R8 may be the same or different and are independently selected from the group consisting of: hydrogen, 1-7C-alkyl, 3-7C-cycloalkyl, Ar, Har and Het, wherein each of said 1-7C-alkyl, 3-7C-cycloalkyl, Ar, Har and Het can be unsubstituted or optionally substituted by at least one substituent independently selected from R12;

each R9 is independently selected from the group consisting of: hydrogen, 1-7C-alkyl, and 3-7C-cycloalkyl, wherein each of said 1-7C-alkyl and 3-7C-cycloalkyl can be unsubstituted or optionally substituted by at least one substituent independently selected from R12;

each R10 is independently selected from the group consisting of: hydrogen, 1-7C-alkyl, and 3-7C-cycloalkyl;

R11 is selected from the group consisting of: R5 as defined above;

each R12 is independently selected from the group consisting of: R5 as defined above;

each Ar is independently selected from phenyl and naphthyl;

each Har is independently any fully aromatic or partially aromatic mono- or fused bicyglic ring or ring system made up of a first constituent being a 5- or 6-membered monocyclic unsaturated, aromatic heteroaryl ring A, which heteroaryl ring A comprises one to four heteroatoms independently selected from nitrogen, oxygen and sulfur, and, optionally, fused to said first constituent, a second constituent being a benzo group, any 3-7C-cycloalkane group as defined herein, any additional heteroaryl ring A as defined herein afore, or any heterocyclic ring B as defined herein below, whereby said Har ring or ring system is attached to the parent molecular group via a substitutable ring carbon or ring nitrogen atom;

each Het is independently any fully saturated or partially unsaturated mono- or fused bicyclic ring or ring system made up of a first constituent being a 3- or 7-membered monocyclic fully saturated or partially unsaturated, non-aromatic heterocyclic ring B, which heterocyclic ring B comprises one to three heteroatoms independently selected from nitrogen, oxygen and sulfur, and which heterocyclic ring B is optionally substituted by one or two oxo groups, and, optionally, fused to said first constituent, a second constituent being a benzo group, any 3-7C-cycloalkane group as defined herein, or any additional heterocyclic ring B as defined herein afore, whereby said Het ring or ring system is attached to the parent molecular group via a substitutable ring carbon or ring nitrogen atom;

and the salts, solvates or the solvates of the salts thereof.

An embodiment of aspect 2 (embodiment 2a) according to this invention includes those compounds of formula I, in which, in an independent embodimental alternative,
Ra is —C(O)R1, in which
R1 is methyl, ethyl, propyl, or butyl;

or in which, in another independent embodimental alternative,
Ra is —C(O)R1, in which
R1 is 1-4C-alkyl substituted by R5, in which
R5 is any one of the groups as defined in aspect 2 above;

or in which, in another independent embodimental alternative,
Ra is —C(O)SR2, in which
R2 is 1-7C-alkyl;

and in which, in an independent embodimental alternative,
Rb is unsubstituted phenyl;

or in which, in another independent embodimental alternative,
Rb is substituted by Rba and/or Rbb, and is phenyl, in which
Rba is attached in the meta position with respect to the binding position in which said phenyl ring is bonded to the adjacent carbonyl group, and is halogen, trifluoromethyl, 1-4C-alkyl, 1-4C-alkoxy, phenoxy, 3-7C-cycloalkoxy, 3-7C-cycloalkyl-1-4C-alkoxy, 1-4C-alkoxy-2-4C-alkoxy, or phenyl-1-4C-alkoxy,
Rbb is attached in the meta or para position with respect to the binding position in which said phenyl ring is bonded to the adjacent carbonyl group, and is trifluoromethyl, 1-4C-alkyl, 1-4C-alkoxy, 3-7C-cycloalkoxy, 3-7C-cycloalkyl-1-4C-alkoxy, 1-4C-alkoxy-2-4C-alkoxy, or phenyl-1-4C-alkoxy, such as e.g. 3-chloro-phenyl, 3-fluoro-phenyl, 3-bromo-phenyl, 4-methyl-phenyl, 3,5-di-trifluoromethyl-phenyl, 4-methoxy-phenyl, 3-methoxy-phenyl, 3,5-dimethoxy-phenyl, 3,4-dimethoxy-phenyl, or 3-phenoxy-phenyl;

or in which, in another independent embodimental alternative,
Rb is unsubstituted naphthyl;

and the salts, solvates and the solvates of the salts thereof.

Compounds according to embodiment 2a more worthy to be mentioned are those compounds of formula I, in which, in an independent embodimental alternative,
Ra is —C(O)R1, in which
R1 is methyl or propyl;

or in which, in another independent embodimental alternative,
Ra is —C(O)R1, in which
R1 is methyl substituted by R5, ethyl substituted by R5, or propyl substituted by R5, in which either, in a independent subembodiment,
R5 is any one of the group consisting of: carbamoyl, 1-4C-alkoxy, 1-4C-alkoxycarbonyl, and 1-4C-alkylcarbonyl, such as e.g. carbamoyl, methoxy, methoxycarbonyl, and acetyl, or, in another independent subembodiment,
R5 is Har, in which
Har is any one of the meanings as defined in aspect 2 above, such as e.g. indolyl, or thiophenyl;

or in which, in another independent embodimental alternative,
Ra is —C(O)SR2, in which
R2 is 1-7C-alkyl, such as e.g. ethyl;

and in which, in an independent embodimental alternative,
Rb is unsubstituted phenyl;

or in which, in another independent embodimental alternative,
Rb is substituted by Rba and/or Rbb, and is phenyl, in which
Rba is attached in the meta position with respect to the binding position in which said phenyl ring is bonded to the adjacent carbonyl group, and is halogen, trifluoromethyl, 1-4C-alkyl, 1-4C-alkoxy, phenoxy, 3-7C-cycloalkoxy, 3-7C-cycloalkyl-1-4C-alkoxy, 1-4C-alkoxy-2-4C-alkoxy, or phenyl-1-4C-alkoxy,
Rbb is attached in the meta or para position with respect to the binding position in which said phenyl ring is bonded to the adjacent carbonyl group, and is trifluoromethyl, 1-4C-alkyl, 1-4C-alkoxy, 3-7C-cycloalkoxy, 3-7C-cycloalkyl-1-4C-alkoxy, 1-4C-alkoxy-2-4C-alkoxy, or phenyl-1-4C-alkoxy, such as e.g. either any one of: 3-chloro-phenyl, 3-methoxy-phenyl, 3,5-dimethoxy-phenyl, 3,4-dimethoxy-phenyl and 3-phenoxy-phenyl, or any one of: 3-methoxy-phenyl and 3,5-dimethoxy-phenyl;

or in which, in another independent embodimental alternative,
Rb is unsubstituted naphthyl;

and the salts, solvates and the solvates of the salts thereof.

A more detailed embodiment of aspect 2 (embodiment 2b) according to this invention includes those compounds of formula I, wherein
Ra is —C(O)R1, in which
R1 is 1-4C-alkyl substituted by R5, in which
R5 is any one of the groups as defined aspect 2 above;

and in which, in an independent embodimental alternative,
Rb is unsubstituted phenyl;

or in which, in another independent embodimental alternative,
Rb is substituted by Rba and/or Rbb, and is phenyl, in which
Rba is attached in the meta position with respect to the binding position in which said phenyl ring is bonded to the adjacent carbonyl group, and is halogen, trifluoromethyl, 1-4C-alkyl, 1-4C-alkoxy, phenoxy, 3-7C-cycloalkoxy, 3-7C-cycloalkyl-1-4C-alkoxy, 1-4C-alkoxy-2-4C-alkoxy, or phenyl-1-4C-alkoxy, Rbb is attached in the meta or para position with respect to the binding position in which said phenyl ring is bonded to the adjacent carbonyl group, and is trifluoromethyl, 1-4C-alkyl, 1-4C-alkoxy, 3-7C-cycloalkoxy, 3-7C-cycloalkyl-1-4C-alkoxy, 1—C-alkoxy-2-4C-alkoxy, or phenyl-1-4C-alkoxy, such as e.g. 3-chloro-phenyl, 3-fluoro-phenyl, 3-bromo-phenyl, 4-methyl-phenyl, 3,5-di-tifluoromethyl-phenyl, 4-methoxy-phenyl, 3-methoxy-phenyl, 3,5-dimethoxy-phenyl, 3,4-dimethoxy-phenyl, or 3-phenoxy-phenyl;

or in which, in another independent embodimental alternative,

Rb is unsubstituted naphthyl;

and the salts, solvates and the solvates of the salts thereof.

Compounds according to embodiment 2b more worthy to be mentioned are those compounds of formula I, Ra is —C(O)R1, in which R1 is 1-4C-alkyl substituted by R5, in which R5 is 1-4C-alkoxycarbonyl, 1-4C-alkylcarbonyl, carbamoyl, guanidino, amidino, carboxyl, mono- or di-1-4C-alkylaminocarbonyl, mono- or di-1-4C-alkylamino, ureido, 1-4C-alkoxy, hydroxyl, 1-4C-alkoxy-2-4C-alkoxy, or phenyl-1-4C-alkoxy;

and in which, in an independent embodimental alternative,

Rb is unsubstituted phenyl;

or in which, in another independent embodimental alternative,

Rb is substituted by Rba and/or Rbb, and is phenyl, in which

Rba is attached in the meta position with respect to the binding position in which said phenyl ring is bonded to the adjacent carbonyl group, and is halogen, trifluoromethyl, 1-4C-alkyl, 1-4C-alkoxy, phenoxy, 3-7C-cycloalkoxy, 3-7C-cycloalkyl-1-4C-alkoxy, 1-4C-alkoxy-2-4C-alkoxy, or phenyl-1-4C-alkoxy, Rbb is attached in the meta or para position with respect to the binding position in which said phenyl ring is bonded to the adjacent carbonyl group, and is trifluoromethyl, 1 AC-alkyl, 1-4C-alkoxy, 3-7C-cycloalkoxy, 3-7C-cycloalkyl-1-4C-alkoxy, 1-4C-alkoxy-2-4C-alkoxy, or phenyl-1-4C-alkoxy, such as e.g. 3-chloro-phenyl, 3-fluoro-phenyl, 3-bromo-phenyl, 4-methyl-phenyl, 3,5-di-trifluoromethyl-phenyl, 4-methoxy-phenyl, 3-methoxy-phenyl, 3,5-dimethoxy-phenyl, 3,4-dimethoxy-phenyl, or 3-phenoxy-phenyl;

or in which, in another independent embodimental alternative,

Rb is unsubstituted naphthyl;

and the salts, solvates and the solvates of the salts thereof.

Yet compounds according to embodiment 2b more worthy to be mentioned are those compounds of formula I, in which Ra is —C(O)R1, in which R1 is 1-4C-alkyl substituted by R5, in which R5 is 1-4C-alkoxycarbonyl, 1-4C-alkylcarbonyl, carbamoyl, 1-4C-alkoxy, 3-7C-cycloalkoxy, 3-7C-cycloalkyl-1-4C-alkoxy, or 1-4C-alkoxy-2-4C-alkoxy;

in an interesting independent embodiment thereof

R1 is 1-4C-alkyl, such as e.g. ethyl, substituted by R5, in which

R5 is carbamoyl, 1-4C-alkoxy, 1-4C-alkoxycarbonyl, or 1-4C-alkylcarbonyl;

in a more interesting independent embodiment thereof

R1 is 1-4C-alkyl, especially ethyl, substituted by R5, in which

R5 is carbamoyl, methoxy, methoxycarbonyl, or acetyl;

and in which, in an independent embodimental alternative,

Rb is unsubstituted phenyl;

or in which, in another independent embodimental alternative,

Rb is substituted by Rba and/or Rbb, and is phenyl, in which

Rba is attached in the meta position with respect to the binding position in which said phenyl ring is bonded to the adjacent carbonyl group, and is halogen, trifluoromethyl, 1-4C-alkyl, 1-4C-alkoxy, phenoxy, 3-7C-cycloalkoxy, 3-7C-cycloalkyl-1-4C-alkoxy, 1-4C-alkoxy-2-4C-alkoxy, or phenyl-1-4C-alkoxy, Rbb is attached in the meta or para position with respect to the binding position in which said phenyl ring is bonded to the adjacent carbonyl group, and is trifluoromethyl, 14C-alkyl, 1-4C-alkoxy, 3-7C-cycloalkoxy, 3-7C-cycloalkyl-1-4C-alkoxy, 1-4C-alkoxy-2-4C-alkoxy, or phenyl-1-4C-alkoxy, such as e.g. 3-chloro-phenyl, 3-fluoro-phenyl, 3-bromo-phenyl, 4-methyl-phenyl, 3,5-di-trifluoromethyl-phenyl, 4-methoxy-phenyl, 3-methoxy-phenyl, 3,5-dimethoxy-phenyl, 3,4-dimethoxy-phenyl, or 3-phenoxy-phenyl;

or in which, in another independent embodimental alternative,

Rb is unsubstituted naphthyl;

and the salts, solvates and the solvates of the salts thereof.

Still yet compounds according to embodiment 2b more worthy to be mentioned are those compounds of formula I, in which Ra is —C(O)R1, in which R1 is 1-4C-alkyl substituted by R5, in which either R5 is phenyl, or R51-substituted phenyl, in which R51 is 1-4C-alkoxy, or R5 is Har, R52-substituted Har, or Het, in which, in a first alternative thereof, Har is attached to the parent molecular group via any ring carbon or ring nitrogen atom, and is an unsaturated (aromatic) 5-membered ring comprising one to four heteroatoms independently selected from nitrogen, oxygen and sulfur which is optionally fused to a benzene ring, or, in a second alternative thereof, Har is attached to the parent molecular group via any ring carbon atom, and is an unsaturated (aromatic) 6-membered ring comprising one or two nitrogen atoms independently selected from nitrogen, oxygen and sulfur which is optionally fused to a benzene ring, R52 is 1-4C-alkyl, or, in a third alternative thereof, Het is attached to the parent molecular group via any ring nitrogen atom, and is a saturated 3- to 7-membered monocyclic ring comprising one or two heteroatoms independently selected from nitrogen, —N(R53)-, oxygen and sulfur, and which is optionally substituted by one or two oxo groups, or a benzo-fused derivative thereof, in which
R53 is 1-4C-alkyl, or 1-4C-alkylcarbonyl, or, in a fourth alternative thereof,
Het is attached to the parent molecular group via any ring carbon atom, and is a saturated 3- to 7-membered monocyclic ring comprising one or two heteroatoms independently selected from nitrogen, —N(R53)-, oxygen and sulfur, which is optionally substituted by one or two oxo groups, and which is optionally fused to a benzene ring, in which
R53 is 1-4C-alkyl, or 1-4C-alkylcarbonyl;

in an interesting independent embodiment thereof
R1 is 1-4C-alkyl substituted by R5, in which
R5 is Har, or Het, in which, in said first alternative,
Har is indolyl, thiophenyl, N-methyl-imidazolyl, methyl-hiazolyl, or imidazolyl (such as e.g. indol-2-yl, indol-3-yl, thiophen-2-yl, 4-methyl-thiazol-5-yl, 1—N-methyl-imidazol-5-yl, 1-N-methyl-imidazol4-yl, 1-NH-imidazol-4-yl, or imidazol-1-yl), or, in said second alternative,
Har is pyridyl, or pyrazinyl (such as e.g. pyridin-2-yl, pyridin-3-yl, or pyridin-4-yl, or pyrazin-2-yl), or, in said third alternative,
Het is piperidinyl, morpholinyl, N-methyl-piperazinyl, or pyrrolidinyl (such as e.g. piperidin-1-yl, morpholino, 4-N-methyl-piperazin-1-yl, or pyrrolidino-1-yl), or, in said fourth alternative,
Het is 1,3-benzodioxolyl (such as e.g. 1,3-benzodioxol-5-yl);

in another interesting independent embodiment thereof
R1 is 1-4C-alkyl substituted by R5, in which
R5 is Har;

in a further interesting independent embodiment thereof
R1 is 1-4C-alkyl substituted by R5, in which
R5 is Har, in which either
Har is indolyl, thiophenyl, N-methyl-imidazolyl, methyl-thiazolyl, or imidazolyl (such as e.g. indol-2-yl, indol-3-yl, thiophen-2-yl, 4-methyl-thiazol-5-yl, 1-N-methyl-imidazol-5-yl, 1-N-methyl-imidazol-4-yl, 1-NH-imidazol-4-yl, or imidazol-1-yl), or
Har is pyridyl, or pyrazinyl (such as e.g. pyridin-2-yl, pyridin-3-yl, or pyridin-4-yl, or pyrazin-2-yl);

in a more interesting independent embodiment thereof
R1 is 1-4C-alkyl, especially ethyl or propyl, substituted by R5, in which
R5 is Har, in which
Har is indolyl (such as e.g. indol-2-yl), thiophenyl (such as e.g. thiophen-2-yl), or methyl-thiazolyl (such as e.g. 4-methyl-thiazol-5-yl);

and in which, in an independent embodimental alternative,
Rb is unsubstituted phenyl;

or in which, in another independent embodimental alternative,
Rb is substituted by Rba and/or Rbb, and is phenyl, in which
Rba is attached in the meta position with respect to the binding position in which said phenyl ring is bonded to the adjacent carbonyl group, and is halogen, trifluoromethyl, 1-4C-alkyl, 1-4C-alkoxy, phenoxy, 3-7C-cycloalkoxy, 3-7C-cycloalkyl-1-4C-alkoxy, 1-4C-alkoxy-2-4C-alkoxy, or phenyl-1-4C-alkoxy,
Rbb is attached in the meta or para position with respect to the binding position in which said phenyl ring is bonded to the adjacent carbonyl group, and is trifluoromethyl, 1-4C-alkyl, 1-4C-alkoxy, 3-7C-cycloalkoxy, 3-7C-cycloalkyl-1-4C-alkoxy, 1-4C-alkoxy-2-4C-alkoxy, or phenyl-1-4C-alkoxy, such as e.g. 3-chloro-phenyl, 3-fluoro-phenyl, 3-bromo-phenyl, 4-methyl-phenyl, 3,5-di-trifluoromethyl-phenyl, 4-methoxy-phenyl, 3-methoxy-phenyl, 3,5-dimethoxy-phenyl, 3,4-dimethoxy-phenyl, or 3-phenoxy-phenyl;

or in which, in another independent embodimental alternative,
Rb is unsubstituted naphthyl;

and the salts, solvates and the solvates of the salts thereof.
Compounds according to embodiment 2b further more worthy to be mentioned are those compounds of formula I, in which
Ra is —C(O)R1, in which
R1 is 1-4C-alkyl substituted by R5, in which
R5 is carbamoyl, 1-4C-alkoxy, 1-4C-alkoxycarbonyl, or 1-4C-alkylcarbonyl;

and in which, in an independent embodimental alternative,
Rb is unsubstituted phenyl;

or in which, in another independent embodimental alternative,
Rb is substituted by Rba and/or Rbb, and is phenyl, in which
Rba is attached in the meta position with respect to the binding position in which said phenyl ring is bonded to the adjacent carbonyl group, and is chlorine, bromine, fluorine, trifluoromethyl, 1-2C-alkyl, 1-2C-alkoxy, or phenoxy,
Rbb is attached in the meta or para position with respect to the binding position in which said phenyl ring is bonded to the adjacent carbonyl group, and is trifluoromethyl, 1-2C-alkyl, or 1-2C-alkoxy, suchs, as e.g. 3-chloro-phenyl, 4-methyl-phenyl, 3-methoxy-phenyl, 3,5-dimethoxy-phenyl, 3,4-dimethoxy-phenyl, or 3-phenoxy-phenyl;

or in which, in another independent embodimental alternative,
Rb is unsubstituted naphthyl;

and the salts, solvates and the solvates of the salts thereof.
Yet compounds according to embodiment 2b further more worthy to be mentioned are those compounds of formula I, in which
Ra is —C(O)R1, in which
R1 is 1-4C-alkyl substituted by R5, in which
R5 is 1-4C-alkoxycarbonyl, 1-4C-alkylcarbonyl, carbamoyl, guanidino, 1-4C-alkoxy, or 1-4C-alkoxy-2-4C-alkoxy, and in which, in an independent embodimental alternative,
Rb is unsubstituted phenyl;

or in which, in another independent embodimental alternative,

Rb is substituted by Rba and/or Rbb, and is phenyl, in which

Rba is attached in the meta position with respect to the binding position in which said phenyl ring is bonded to the adjacent carbonyl group, and is chlorine, bromine, fluorine, trifluoromethyl, 1-2C-alkyl, 1-2C-alkoxy, or phenoxy, Rbb is attached in the meta or para position with respect to the binding position in which said phenyl ring is bonded to the adjacent carbonyl group, and is trifluoromethyl, 1-2C-alkyl, or 1-2C-alkoxy, such as e.g. 3-chloro-phenyl, 4-methyl-phenyl, 3-methoxy-phenyl, 3,5-dimethoxy-phenyl, 3,4-dimethoxy-phenyl, or 3-phenoxy-phenyl;

or in which, in another independent embodimental alternative,

Rb is unsubstituted naphthyl;

and the salts, solvates and the solvates of the salts thereof.

Still yet compounds according to embodiment 2b furthermore worthy to be mentioned are those compounds of formula I, in which R1 is 1-4C-alkyl substituted by R5, in which R5 is Har, in which either Har is indolyl, thiophenyl, N-methyl-imidazolyl, methyl4hiazolyl, or imidazolyl (such as e.g. indol-2-yl, indol-3-yl, thiophen-2-yl, 4-methyl-thiazol-5-yl, 1—N-methyl-imidazol-5-yl, 1-N-methyl-imidazol4-yl, 1-NH-imidazol-4-yl, or imidazol-1-yl), or Har is pyridyl, or pyrazinyl (such as e.g. pyridin-2-yl, pyridin-3-yl, or pyridin4-yl, or pyrazin-2-yl);

and in which, in an independent embodimental alternative,

Rb is unsubstituted phenyl;

or in which, in another independent embodimental alternative,

Rb is substituted by Rba and/or Rbb, and is phenyl, in which

Rba is attached in the meta position with respect to the binding position in which said phenyl ring is bonded to the adjacent carbonyl group, and is chlorine, bromine, fluorine, trifluoromethyl, 1-2C-alkyl, 1-2C-alkoxy, or phenoxy, Rbb is attached in the meta or para position with respect to the binding position in which said phenyl ring is bonded to the adjacent carbonyl group, and is trifluoromethyl, 1-2C-alkyl, or 1-2C-alkoxy, such as e.g. 3-chloro-phenyl, 4-methyl-phenyl, 3-methoxy-phenyl, 3,5-dimethoxy-phenyl, 3,4-dimethoxy-phenyl, or 3-phenoxy-phenyl;

or in which, in another independent embodimental alternative,

Rb is unsubstituted naphthyl;

and the salts, solvates and the solvates of the salts thereof.

Another more detailed embodiment of aspect 2 (embodiment 2c) according to this invention includes those compounds of formula I, wherein Ra is —C(O)R1, in which R1 is methyl, ethyl, propyl or butyl;

and in which, in an independent embodimental alternative,

Rb is unsubstituted phenyl;

or in which, in another independent embodimental alternative,

Rb is substituted by Rba and/or Rbb, and is phenyl, in which

Rba is attached in the meta position with respect to the binding position in which said phenyl ring is bonded to the adjacent carbonyl group, and is halogen, trifluoromethyl, 1-4C-alkyl, 1-C-alkoxy, phenoxy, 3-7C-cycloalkoxy, 3-7C-cycloalkyl-1-4C-alkoxy, 1-4C-alkoxy-2-4C-alkoxy, or phenyl-1-4C-alkoxy, Rbb is attached in the meta or para position with respect to the binding position in which said phenyl ring is bonded to the adjacent carbonyl group, and is trifluoromethyl, 1-4C-alkyl, 1-C-alkoxy, 3-7C-cycloalkoxy, 3-7C-cycloalkyl-1-4C-alkoxy, 1-4C-alkoxy-2-4C-alkoxy, or phenyl-1-4C-alkoxy, such as e.g. 3-chloro-phenyl, 3-fluoro-phenyl, 3-bromo-phenyl, 4-methyl-phenyl, 3,5-di-trifluoromethyl-phenyl, 4-methoxy-phenyl, 3-methoxy-phenyl, 3,5-dimethoxy-phenyl, 3,4-dimethoxy-phenyl, or 3-phenoxy-phenyl;

or in which, in another independent embodimental alternative,

Rb is unsubstituted naphthyl;

and the salts, solvates and the solvates of the salts thereof.

Compounds according to embodiment 2c more worthy to be mentioned are those compounds of formula I, wherein Ra is —C(O)R1, in which R1 is methyl, ethyl, propyl or butyl;

and in which, in an independent embodimental alternative,

Rb is unsubstituted phenyl;

or in which, in another independent embodimental alternative,

Rb is substituted by Rba and/or Rbb, and is phenyl, in which

Rba is attached in the meta position with respect to the binding position in which said phenyl ring is bonded to the adjacent carbonyl group, and is chlorine, bromine, fluorine, trifluoromethyl, 1-2C-alkyl, 1-2C-alkoxy, or phenoxy, Rbb is attached in the meta or para position with respect to the binding position in which said phenyl ring is bonded to the adjacent carbonyl group, and is trifluoromethyl, 1-2C-alkyl, or 1-2C-alkoxy, such as e.g. 3-chloro-phenyl, 4-methyl-phenyl, 3-methoxy-phenyl, 3,5-dimethoxy-phenyl, 3,4-dimethoxy-phenyl, or 3-phenoxy-phenyl;

or in which, in another independent embodimental alternative,

Rb is unsubstituted naphthyl;

and the salts, solvates and the solvates of the salts thereof.

Yet another more detailed embodiment of aspect 2 (embodiment 2d) according to this invention includes those compounds of formula I, wherein
Ra is —C(O)SR2, in which
R2 is 1-7C-alkyl;

and in which, in an independent embodimental alternative,
Rb is unsubstituted phenyl;

or in which, in another independent embodimental alternative,
Rb is substituted by Rba and/or Rbb, and is phenyl, in which
Rba is attached in the meta position with respect to the binding position in which said phenyl ring is bonded to the adjacent carbonyl group, and is halogen, trifluoromethyl, 1-4C-alkyl, 1-4C-alkoxy, phenoxy, 3-7C-cycloalkoxy, 3-7C-cycloalkyl-1-4C-alkoxy, 1-4C-alkoxy-2-4C-alkoxy, or phenyl-1-4C-alkoxy,
Rbb is attached in the meta or para position with respect to the binding position in which said phenyl ring is bonded to the adjacent carbonyl group, and is trifluoromethyl, 1-4C-alkyl, 1-4C-alkoxy, 3-7C-cycloalkoxy, 3-7C-cycloalkyl-1-4C-alkoxy, 1-4C-alkoxy-2-4C-alkoxy, or phenyl-1-4C-alkoxy, such as e.g. 3-chloro-phenyl, 3-fluoro-phenyl, 3-bromo-phenyl, 4-methyl-phenyl, 3,5-di-trifluoromethyl-phenyl, 4-methoxy-phenyl, 3-methoxy-phenyl, 3,5-dimethoxy-phenyl, 3,4-dimethoxy-phenyl, or 3-phenoxy-phenyl;

or in which, in another independent embodimental alternative,
Rb is unsubstituted naphthyl;

and the salts, solvates and the solvates of the salts thereof.

Compounds according to embodiment 2d more worthy to be mentioned are those compounds of formula I, wherein
Ra is —C(O)SR2, in which
R2 is 1-7C-alkyl;

and in which, in an independent embodimental alternative,
Rb is unsubstituted phenyl;

or in which, in another independent embodimental alternative,
Rb is substituted by Rba and/or Rbb, and is phenyl, in which
Rba is attached in the meta position with respect to the binding position in which said phenyl ring is bonded to the adjacent carbonyl group, and is chlorine, bromine, fluorine, trifluoromethyl, 1-2C-alkyl, 1-2C-alkoxy, or phenoxy,
Rbb is attached in the meta or para position with respect to the binding position in which said phenyl ring is bonded to the adjacent carbonyl group, and is trifluoromethyl, 1-2C-alkyl, or 1-2C-alkoxy, such as e.g. 3-chloro-phenyl, 4-methyl-phenyl, 3-methoxy-phenyl, 3,5-dimethoxy-phenyl, 3,4-dimethoxy-phenyl, or 3-phenoxy-phenyl;

or in which, in another independent embodimental alternative,
Rb is unsubstituted naphthyl;

and the salts, solvates and the solvates of the salts thereof.

In a third aspect (aspect 3), which is an embodiment of aspect 2, the present invention relates to those compounds of formula I, in which, in an independent embodimental alternative,
Ra is —C(O)R1, in which
R1 is 1-4C-alkyl;

or in which, in another independent embodimental alternative,
Ra is —C(O)R1, in which
R1 is 1-4C-alkyl substituted by two hydroxyl radicals;

or in which, in another independent embodimental alternative,
Ra is —C(O)R1, in which
R1 is 1-4C-alkyl substituted by R5, in which
R5 is selected from the group consisting of:
  3-7C-cycloalkyl,
  halogen, trifluoromethyl, cyano, guanidino, hydroxyl,
  Har, phenyl, morpholino,
  —C(O)R6, —C(O)OR7, —C(O)N(R8)R9,
  —N(R10)C(O)R6, —OC(O)R6,
  completely or predominantly fluorine-substituted 1-4C-alkoxy,
  1-4C-alkoxy, 3-7C-cycloalkoxy, 3-7C-cycloalkyl-1-4C-alkoxy, hydroxy-2-4C-alkoxy, 1-4C-alkoxy-2-4C-alkoxy, phenyl-1-4C-alkoxy, pyridyl-1-4C-alkoxy, and (1-4C-alkoxy-2-4C-alkoxy)-2-4C-alkoxy, wherein said Har may be optionally substituted by one or two substituents independently selected from R11,
R6, R7 and R8 may be the same or different and are independently selected from the group consisting of:
  hydrogen and 1-4C-alkyl,
R9 is selected from the group consisting of:
  hydrogen and 1-4C-alkyl,
R10 is selected from the group consisting of:
  hydrogen and 1-4C-alkyl,
R11 is selected from the group consisting of:
  1-4C-alkyl, halogen and 1-4C-alkoxy either
Har is bonded to the parent molecular group via a ring carbon or a ring nitrogen atom, and is a 5-membered monocyclic unsaturated, aromatic heteroaryl ring comprising one to four heteroatoms independently selected from nitrogen, oxygen and sulphur, or
Har is bonded to the parent molecular group via a ring carbon atom, and is a 6-membered monocyclic unsaturated, aromatic heteroaryl ring comprising one or two nitrogen atoms, or
Har is bonded to the parent molecular group via a ring carbon or a ring nitrogen atom, and is a 9- or 10-membered fused bicyclic unsaturated, aromatic heteroaryl ring comprising one to three heteroatoms independently selected from nitrogen, oxygen and sulphur, or in which, in yet another independent embodimental alternative,
Ra is —C(O)SR2, in which
R2 is 1-7C-alkyl;

and in which, in an independent embodimental alternative,
Rb is unsubstituted phenyl;

or in which, in another independent embodimental alternative,
Rb is substituted by Rba and/or Rbb, and is phenyl, in which
Rba is halogen, trifluoromethyl, 1-4C-alkyl, or 1-4C-alkoxy, Rbb is halogen, trifluoromethyl, 1-4C-alkyl, 1-4C-alkoxy, phenoxy, nitro, hydroxyl, or 1-4C-alkylcarbonyl;

or in which, in yet another independent embodimental alternative,
Rb is unsubstituted naphthyl;

and the salts, solvates and the solvates of the salts thereof.

Compounds according to aspect 3 more worthy to be mentioned are those compounds of formula I, in which, in an independent embodimental alternative,
Ra is —C(O)R1, in which
R1 is 1-4C-alkyl;

or in which, in another independent embodimental alternative,
Ra is —C(O)R1, in which
R1 is 1-4C-alkyl substituted by R5, in which
R5 is selected from the group consisting of:
  hydroxyl, guanidino,
  pyridinyl, indolyl, thiophenyl, thiazolyl, triazol-1-yl, imidazol-1-yl, pyrazol-1-yl, morpholino,
  —C(O)R6, —C(O)OR7, —C(O)N(R8)R9, —N(R10)C(O)R6, —OC(O)R6,
  1-4C-alkoxy, hydroxy-2-4C-alkoxy, 1-4C-alkoxy-2-4C-alkoxy, pyridyl-1-4C-alkoxy, and (1-4C-alkoxy-2-4C-alkoxy)-2-4C-alkoxy,
R6 is 1-4C-alkyl,
R7 and R8 may be the same or different and are independently selected from the group consisting of:
  hydrogen and 1-4C-alkyl,
R9 is selected from the group consisting of:
  hydrogen and 1-4C-alkyl,
R10 is selected from the group consisting of:
  hydrogen and 1-4C-alkyl, or in which, in yet another independent embodimental alternative,
Ra is —C(O)SR2, in which
R2 is 1-4C-alkyl;

and in which, in an independent embodimental alternative,
Rb is unsubstituted phenyl;

or in which, in another independent embodimental alternative,
Rb is substituted by Rba and/or Rbb, and is phenyl, in which
Rba is attached in the meta position with respect to the binding position in which said phenyl ring is bonded to the adjacent carbonyl group, and is halogen, trifluoromethyl, 1-4C-alkyl, or 1-4C-alkoxy,
Rbb is attached in the meta or para position with respect to the binding position in which said phenyl ring is bonded to the adjacent carbonyl group, and is halogen, trifluoromethyl, 1-4C-alkyl, 1-4C-alkoxy, or phenoxy, or 1-4C-alkylcarbonyl,
such as e.g. 3-chloro-phenyl, 3-fluoro-phenyl, 3-bromo-phenyl, 4-methyl-phenyl, 3,5-di-trifluoromethyl-phenyl, 4-methoxy-phenyl, 3-methoxy-phenyl, 3,5-dimethoxy-phenyl, 3,4-dimethoxy-phenyl, 3-phenoxy-phenyl, or 4-acetyl-phenyl;

or in which, in another independent embodimental alternative,
Rb is unsubstituted naphthyl;

and the salts, solvates and the solvates of the salts thereof.

Compounds according to aspect 3 in particular worthy to be mentioned are those compounds of formula I, in which, in an independent embodimental alternative,
Ra is —C(O)R1, in which
R1 is 1-4C-alkyl;

or in which, in another independent embodimental alternative,
Ra is —C(O)R1, in which
R1 is 1-4C-alkyl, such as e.g. methyl, ethyl or propyl, which is substituted by R5, in which
R5 is selected from the group consisting of:
  hydroxyl,
  pyridinyl, morpholino,
  —C(O)OR7, —OC(O)R6,
  1-2C-alkoxy, 1-2C-alkoxy-2-3C-alkoxy, and (1-2C-alkoxy-2-3C-alkoxy)-2-3C-alkoxy,
R6 is 1-2C-alkyl,
R7 is selected from the group consisting of:
  hydrogen and 1-2C-alkyl, or in which, in yet another independent embodimental alternative,
Ra is —C(O)SR2, in which
R2 is 1-4C-alkyl;

and in which, in an independent embodimental alternative,
Rb is unsubstituted phenyl;

or in which, in another independent embodimental alternative,
Rb is substituted by Rba and/or Rbb, and is phenyl, in which
Rba is attached in the meta position with respect to the binding position in which said phenyl ring is bonded to the adjacent carbonyl group, and is chlorine, bromine, fluorine, trifluoromethyl, 1-2C-alkyl, or 1-2C-alkoxy,
Rbb is attached in the meta or para position with respect to the binding position in which said phenyl ring is bonded to the adjacent carbonyl group, and is trifluoromethyl, 1-2C-alkyl, 1-2C-alkoxy, or phenoxy, such as e.g. 3-chloro-phenyl, 4-methyl-phenyl, 3-methoxy-phenyl, 3,5-dimethoxy-phenyl, 3,4-dimethoxy-phenyl, or 3-phenoxy-phenyl;

and the salts, solvates and the solvates of the salts thereof.

Compounds according to aspect 3 in more particular worthy to be mentioned are those compounds of formula I, in which, in an independent embodimental alternative,
Ra is —C(O)R1, in which
R1 is 1-4C-alkyl;

or in which, in another independent embodimental alternative,
Ra is —C(O)R1, in which
R1 is 1-4C-alkyl, such as e.g. methyl, ethyl or propyl, which is substituted by R5, in which
R5 is selected from the group consisting of:
  hydroxyl,
  pyridinyl,
  —C(O)OR7,
  methoxy, ethoxy, 2-methoxy-ethoxy, and 2-(2-methoxy-ethoxy)-ethoxy,
R6 is methyl or ethyl,
R7 is selected from the group consisting of:
  hydrogen, methyl and ethyl, or in which, in yet another independent embodimental alternative,
Ra is —C(O)SR2, in which
R2 is 1-4C-alkyl;

and
in which, in an independent embodimental alternative,
Rb is unsubstituted phenyl;

or in which, in another independent embodimental alternative,
Rb is substituted by Rba and/or Rbb, and is phenyl, in which
Rba is attached in the meta position with respect to the binding position in which said phenyl ring is bonded to the adjacent carbonyl group, and is 1-2C-alkoxy,
Rbb is attached in the meta or para position with respect to the binding position in which said phenyl ring is bonded to the adjacent carbonyl group, and is 1-2C-alkoxy, such as e.g. 3-methoxy-phenyl, 3,5-dimethoxy-phenyl, or 3,4-dimethoxy-phenyl; and the salts, solvates and the solvates of the salts thereof.

In a fourth aspect (aspect 4), which is an embodiment of aspect 2, the present invention relates to those compounds of formula I,
in which
Ra is —C(O)R1, in which
either
R1 is 1-4C-alkyl,
or
R1 is 1-4C-alkyl which is substituted by one substituent selected from R5,
or
R1 is 2-4C-alkyl which is substituted by two hydroxyl groups on different carbon atoms,
or
R1 is 2,2-dimethyl-[1,3]dioxolan4-yl, or 1-2C-alkyl which is substituted by 2,2-dimethyl-[1,3]dioxolan4-yl;
or in which
Ra is —C(O)SR2, in which
either
R2 is 1-7C-alkyl,
or
R2 is 1-7C-alkyl which is substituted by one substituent selected from R5,
or
R2 is 3-4C-alkyl which is substituted by two hydroxyl groups on different carbon atoms,
or
R2 is 1-2C-alkyl which is substituted by 2,2-dimethyl-[1,3]dioxolanfyl;
and in which
either
Rb is substituted by Rba and/or Rbb, and is phenyl,
or
Rb is unsubstituted phenyl,
or
Rb is unsubstituted naphthyl;
in which
each R5 is independently selected from the group consisting of:
1-4C-alkoxy, 1-4C-alkoxy-2-4C-alkoxy, (1-4C-alkoxy-2-4C-alkoxy)-2-4C-alkoxy, hydroxyl, 1-4C-alkylcarbonyloxy, phenoxy, phenyl-1-4C-alkoxy, 1-4C-alkoxycarbonyl, carboxyl, amino, mono- or di-1-4C-alkylamino, mono- or di-1-4C-alkylaminocarbonyl, carbamoyl, ureido, guanidino, 1-4C-alkylcarbonylamino, Het, Har and phenyl,
wherein each of said Har or phenyl radicals alone or part of another group may be unsubstituted or optionally substituted by one or two substituents independently selected from halogen, 1-4C-alkoxy, nitro, trifluoromethyl, 1-4C-alkyl, 1-4C-alkoxycarbonyl and carboxyl, in which
Har is either
a 5-membered monocyclic heteroaryl radical comprising one, two or three heteroatoms independently selected from nitrogen, oxygen and sulphur,
such as e.g. any one selected from furanyl, thiophenyl, pyrrolyl, oxazolyl, isoxazolyl, thiazolyl, isothiazolyl, imidazolyl, pyrazolyl, triazolyl, thiadiazolyl and oxadiazolyl,
or
a 6-membered monocyclic heteroaryl radical comprising one or two nitrogen atoms, such as e.g. any one selected from pyridinyl, pyrazinyl, pyridazinyl and pyrimidinyl,
or
a 9-membered fused bicyclic heteroaryl radical comprising one, two or three heteroatoms independently selected from nitrogen, oxygen and sulphur,
such as e.g. any one selected from indolyl, benzothiophenyl, benzofuranyl, benzoxazoly, benzisoxazolyl, benzothiazolyl, benzoisothiazolyl, benzimidazolyl, indazolyl, benzotriazolyl, benzothiadiazolyl and benzoxadiazolyl,
or
a 10-membered fused bicyclic heteroaryl radical comprising one, two or three heteroatoms independently selected from nitrogen, oxygen and sulphur,
such as e.g. any one selected from quinolinyl, isoquinolinyl, quinoxalinyl, quinazolinyl and cinnolinyl, whereby said Har radical is attached to the parent molecular group via a ring carbon atom or ring nitrogen atom,
Het is morpholino, piperidino, pyrrolidino, 4N-H-piperazino, 4N-(1-4C-alkyl)-piperazino, thiomorpholino, S-oxo-thiomorpholino or S,S-dioxo-thiomorpholino;
Rba is halogen, trifluoromethyl, 1-4C-alkyl, hydroxyl, nitro, phenoxy or 1-4C-alkoxy,
Rbb is halogen, trifluoromethyl, 1-4C-alkyl or 1-4C-alkoxy;

and the salts, solvates or the solvates of the salts thereof.
Compounds according to aspect 4 more worthy to be mentioned are those compounds of formula I,
in which
Ra is —C(O)R1, in which
either
R1 is 1-4C-alkyl,
or
R1 is 1-4C-alkyl which is mono-substituted by R5, in which
R5 is 1-4C-alkoxy, 1-4C-alkoxy-2-4C-alkoxy, (1-4C-alkoxy-2-4C-alkoxy)-2-4C-alkoxy, hydroxyl, phenyl-1-4C-alkoxy, phenoxy, pyridyl, pyrimidinyl, pyrazinyl, indolyl, benzofuranyl, benzothiophenyl, thiophenyl, furanyl, thiazolyl, oxazolyl, 1N-(1-4C-alkyl)-imidazolyl, 1N-(1-4C-alkyl)-pyra phenyl, 1-4C-alkoxycarbonyl, carboxyl, amino, morpholino, piperidino, pyrrolidino, 4N-(1-4C-alkyl)-piperazino, mono- or di-1-4C-alkylamino, mono- or di-1-4C-alkylaminocarbonyl, carbamoyl, ureido, guanidino, imidazolo, triazolo, pyrazolo, 1-4C-alkylcarbonyl, 1-4C-alkylcarbonyloxy or 1-4C-alkylcarbonylamino, wherein each of said pyridyl, pyrimidinyl, pyrazinyl, indolyl, benzofuranyl, benzothiophenyl, thiophenyl, furanyl, thiazolyl, oxazolyl, 1N-(1-4C-alkyl)-imidazolyl, 1N-(1-4C-alkyl)-pyrazolyl, imidazolo, pyrazolo or phenyl radicals alone or part of another group may be unsubstituted or optionally substituted by one or two substituents independently selected from halogen, 1-4C-alkoxy, nitro and 1-4C-alkyl, or R1 is 3-4C-alkyl which is substituted by two hydroxyl groups on different carbon atoms, or R1 is 1-2C-alkyl which is substituted by 2,2-dimethyl-[1,3]dioxolan4-yl;

or in which

Ra is —C(O)SR2, in which either

R2 is 1-6C-alkyl, or

R2 is 1-4C-alkyl which is mono-substituted by R5, in which

R5 is pyridyl, pyrimidinyl, pyrazinyl, indolyl, benzofuranyl, benzothiophenyl, thiazolyl, oxazolyl, 1N-(1-4C-alkyl)-imidazolyl, 1N-(1-4C-alkyl)-pyrazolyl, phenyl, 1-4C-alkoxycarbonyl, carboxyl, mono- or di-1-4C-alkylaminocarbonyl or carbamoyl, wherein each of said pyridyl, pyrimidinyl, pyrazinyl, indolyl, benzofuranyl, benzothiophenyl, thiazolyl, oxazolyl, 1N-(1-4C-alkyl)-imidazolyl, 1N-(1-4C-alkyl)-pyrazolyl or phenyl radicals can be unsubstituted or optionally substituted by one or two substituents independently selected from halogen, 1-4C-alkoxy, nitro and 1-4C-alkyl, or R2 is 2-4C-alkyl which is mono-substituted by R5, in which R5 is 1-4C-alkoxy, 1-4C-alkoxy-2-4C-alkoxy, (1-4C-alkoxy-2-4C-alkoxy)-2-4C-alkoxy, hydroxyl, phenyl-1-4C-alkoxy, phenoxy, amino, morpholino, piperidino, pyrrolidino, 4N-(1-4C-alkyl)-piperazino, mono- or di-1-4C-alkylamino, ureido, guanidino, imidazolo, triazolo, pyrazolo, 1-4C-alkylcarbonyloxy or 1-4C-alkylcarbonylamino, wherein each of said imidazolo, pyrazolo or phenyl radicals alone or part of another group can be unsubstituted or optionally substituted by one or two substituents independently selected from halogen, 1-4C-alkoxy, nitro and 1-4C-alkyl;

and in which either

Rb is unsubstituted phenyl, or

Rb is unsubstituted naphthyl, or

Rb is substituted by Rba and/or Rbb, and is phenyl, in which

Rba is chlorine, fluorine, bromine, trifluoromethyl, methyl, ethyl, methoxy or ethoxy, Rbb is chlorine, fluorine, bromine, trifluoromethyl, methyl, ethyl, methoxy or ethoxy, such as e.g. 3-chloro-phenyl, 4-chlorophenyl, 3-fluoro-phenyl, 3-bromo-phenyl, 2-methyl-phenyl, 3-methyl-phenyl, 4-methyl-phenyl, 3,5-di-trifluoromethyl-phenyl, 4-methoxy-phenyl, 3-methoxy-phenyl, 3,5-dimethoxy-phenyl or 3,4-dimethoxy-phenyl;

and the salts, solvates or the solvates of the salts thereof.

Compounds according to aspect 4 in particular worthy to be mentioned are those compounds of formula I, in which Ra is —C(O)R1, in which either R1 is methyl, ethyl, propyl or butyl, or R1 is methyl which is mono-substituted by R5, ethyl which is mono-substituted by R5, or propyl which is mono-substituted by R5, in which R5 is methoxy, ethoxy, 2-methoxyethoxy, 2-(2-methoxyethoxy)-ethoxy, hydroxyl, pyridyl, pyrimidinyl, pyrazinyl, indolyl, thiophenyl, furanyl, thiazolyl, oxazolyl, 1N-methyl-imidazolyl, 1N-methyl-pyrazolyl, phenyl, methoxycarbonyl, ethoxycarbonyl, carboxyl, dimethylaminocarbonyl, morpholino, piperidino, pyrrolidino, 4N-(methyl)-piperazino, carbamoyl, ureido, guanidino, acetyl, imidazolo, triazolo, pyrazolo, ethylcarbonyloxy or methylcarbonyloxy, or R1 is propyl or butyl, each of which is substituted by two hydroxyl groups on different carbon atoms, or R1 is methyl or ethyl, each of which is substituted by 2,2-dimethyl-[1,3]dioxolanyl-4-yl;

or in which

Ra is —C(O)SR2, in which either

R2 is methyl, ethyl, propyl, butyl or pentyl, or

R2 is methyl which is mono-substituted by R5, ethyl which is mono-substituted by R5, or propyl which is mono-substituted by R5, in which R5 is pyridyl, or R2 is ethyl which is mono-substituted by R5, or propyl which is mono-substituted by R5, in which R5 is hydroxyl, methoxy or ethoxy;

and in which either

Rb is unsubstituted phenyl, or

Rb is substituted by Rba and/or Rbb, and is phenyl, in which

Rba is chlorine, methyl, methoxy or ethoxy,

Rbb is chlorine, methyl, methoxy or ethoxy, such as e.g. 3-chloro-phenyl, 4chloro-phenyl, 2-methyl-phenyl, 3-methyl-phenyl, 4-methyl-phenyl, 3-methoxy-phenyl, 4-methoxy-phenyl or 3,5-dimethoxy-phenyl;

and the salts, solvates and the solvates of the salts thereof.

Compounds according to aspect 4 in more particular worthy to be mentioned are those compounds of formula I, in which Ra is —C(O)R1, in which either R1 is methyl, ethyl or propyl, or
R1 is (R5)-methyl, 2-(R5)-ethyl, or 3-(R5)-propyl, in which
R5 is methoxy, ethoxy, 2-methoxyethoxy, 2-(2-methoxy-ethoxy)-ethoxy, hydroxyl, pyridyl, pyrimidinyl, pyrazinyl, imidazolo, pyrazolo or methylcarbonyloxy, or
R1 is 2,3-dihydroxy-propyl;

or in which
Ra is —C(O)SR2, in which either
R2 is methyl, ethyl or propyl, or
R2 is (R5)-methyl, 2-(R5)-ethyl, or 3-(R5)-propyl, in which
R5 is pyridyl, or
R2 is 2-(R5)-ethyl, or 3-(R5)-propyl, in which
R5 is hydroxyl;

and in which either
Rb is unsubstituted phenyl, or
Rb is substituted by Rba and/or Rbb, and is phenyl, in which
Rba is attached in the meta position with respect to the binding position in which said phenyl ring is bonded to the adjacent carbonyl group, and is methoxy or ethoxy,
Rbb is attached in the meta or para position with respect to the binding position in which said phenyl ring is bonded to the adjacent carbonyl group, and is methoxy or ethoxy, such as e.g. 3-methoxy-phenyl, 3,4-dimethoxyphenyl or 3,5-dimethoxy-phenyl;

and the salts, solvates and the solvates of the salts thereof.

Compounds according to aspect 4 to be emphasized are those compounds of formula I, in which
Ra is —C(O)R1, in which either
R1 is (R5)-methyl, or 2-(R5)-ethyl, in which
R5 is methoxy, 2-methoxyethoxy, hydroxyl or pyridyl, or
R1 is 2,3-dihydroxy-propyl;

or in which
Ra is —C(O)SR2, in which either
R2 is ethyl, or
R2 is (R5)-methyl, or 2-(R5)-ethyl, in which
R5 is pyridyl, or
R2 is 2-(R5)-ethyl, in which
R5 is hydroxyl;

and in which
Rb is 3-methoxy-phenyl or 3,5-dimethoxy-phenyl;

and the salts, solvates and the solvates of the salts thereof.

In a fifth aspect (aspect 5), the present invention relates to certain purposively selected compounds of formula I, which are those compounds of formula I, in which, in a first independent embodimental alternative,
Ra is —C(O)R1, in which
R1 is 1-7C-alkyl;

or in which, in a second independent embodimental alternative,
Ra is —C(O)R1, in which
R1 is 1-7C-alkyl, such as e.g. 1-4C-alkyl, substituted by R5, in which
R5 is any one of the groups as defined in aspect 1 above;

or in which, in a third independent embodimental alternative,
Ra is —C(O)OR2, in which
R2 is 1-7C-alkyl;

or in which, in a fourth independent embodimental alternative,
Ra, is —C(O)O R2, in which
R2 is 1-7C-alkyl, such as e.g. 2-4C-alkyl, substituted by R5, in which
R5 is any one of the groups as defined in aspect 1 above;

or in which, in a fifth independent embodimental alternative,
Ra is —C(O)SR2, in which
R2 is 1-7C-alkyl;

and in which, in another first independent embodimental alternative,
Rb is unsubstituted phenyl;

or in which, in another second independent embodimental alternative,
Rb is substituted by Rba and/or Rbb, and is phenyl, in which
Rba is attached in the meta position with respect to the binding position in which said phenyl ring is bonded to the adjacent carbonyl group, and is halogen, trifluoromethyl, 1-4C-alkyl, 1-4C-alkoxy, phenoxy, 3-7C-cycloalkoxy, 3-7C-cycloalkyl-1-4C-alkoxy, 1-4C-alkoxy-2-4C-alkoxy, or phenyl-1-4C-alkoxy,
Rbb is attached in the meta or para position with respect to the binding position in which said phenyl ring is bonded to the adjacent carbonyl group, and is trifluoromethyl, 1-4C-alkyl, 1-4C-alkoxy, 3-7C-cycloalkoxy, 3-7C-cycloalkyl-1-4C-alkoxy, 1-4C-alkoxy-2-4C-alkoxy, or phenyl-1-4C-alkoxy;

or in which, in another third independent embodimental alternative,
Rb is unsubstituted naphthyl;

and the salts, solvates and the solvates of the salts thereof.

In a subaspect of aspect 5 of this invention, the present invention relates to those compounds of formula I, in which, in a first independent embodimental alternative,
Ra is —C(O)R1, in which
R1 is 1-7C-alkyl, such as e.g. methyl, propyl, or hexyl;

or in which, in a second independent embodimental alternative,
Ra is —C(O)R1, in which
R1 is 1-7C-alkyl, such as e.g. ethyl or propyl, substituted by R5, in which either, in a independent subembodiment,
R5 is any one of the group consisting of: carbamoyl, 1-4C-alkoxy, 1-4C-alkoxycarbonyl, and 1-4C-alkylcarbonyl, such as e.g. carbamoyl, methoxy, methoxycarbonyl, and acetyl, or, in another independent subembodiment,
R5 is Har, in which
Har is any one of the meanings as defined in aspect 1 above, such as e.g. indolyl, or thiophenyl;

or in which, in a third independent embodimental alternative,
Ra is —C(O)OR2, in which
R2 is 1-7C-alkyl, such as e.g. methyl, ethyl, or pentyl;

or in which, in a fourth independent embodimental alternative,
Ra is —C(O)OR2, in which
R2 is 2-7C-alkyl, such as e.g. ethyl, substituted by R5, in which either, in a independent subembodiment,
R5 is 1-4C-alkoxy, such as e.g. methoxy, or, in another independent subembodiment,
R5 is Har, in which
Har is any one of the meanings as defined in aspect 1 above, such as e.g. 4-methyl-thiazol-5-yl;

or in which, in a fifth independent embodimental alternative,
Ra is —C(O)SR2, in which
R2 is 1-7C-alkyl, such as e.g. ethyl;

and in which, in another first independent embodimental alternative,
Rb is unsubstituted phenyl;

or in which, in another second independent embodimental alternative,
Rb is substituted by Rba and/or Rbb, and is phenyl, in which
Rba is attached in the meta position with respect to the binding position in which said phenyl ring is bonded to the adjacent carbonyl group, and is halogen, trifluoromethyl, 1-4C-alkyl, 1-4C-alkoxy, phenoxy, 3-7C-cycloalkoxy, 3-7C-cycloalkyl-1-4C-alkoxy, 1-4C-alkoxy-2-4C-alkoxy, or phenyl-1-4C-alkoxy,
Rbb is attached in the meta or para position with respect to the binding position in which said phenyl ring is bonded to the adjacent carbonyl group, and is trifluoromethyl, 1-4C-alkyl, 1-4C-alkoxy, 3-7C-cycloalkoxy, 3-7C-cycloalkyl-1-4C-alkoxy, 1-4C-alkoxy-2-4C-alkoxy, or phenyl-1-4C-alkoxy;

or in which, in another third independent embodimental alternative,
Rb is unsubstituted naphthyl;

and the salts, solvates and the solvates of the salts thereof.

A special-aspect of the compounds of aspect 5 according to this invention refers tobthose compounds according to aspect 5, in which
Ra is —C(O)R1, in which
R1 is methyl, ethyl, propyl or butyl, such as e.g. methyl or propyl.

A special aspect of the compounds of aspect 5 according to this invention refers to those compounds according to aspect 5, in which
Ra is —C(O)R1, in which
R1 is 1-7C-alkyl, such as e.g. methyl, propyl, or hexyl.

A special aspect of the compounds of aspect 5 according to this invention refers to those compounds according to aspect 5, in which
Ra is —C(O)OR2, in which
R2 is 1-7C-alkyl, such as e.g. methyl, ethyl, or pentyl.

A special aspect of the compounds of aspect 5 according to this invention refers to those compounds according to aspect 5, in which
Rb is monosubstituted by Rba, and is phenyl, in which
Rba is attached in the meta position with respect to the binding position in which said phenyl ring is bonded to the adjacent carbonyl group.

A special aspect of the compounds of aspect 5 according to this invention refers to those compounds according to aspect 5, in which
Rb is monosubstituted by Rbb, and is phenyl, in which
Rbb is attached in the para position with respect to the binding position in which said phenyl ring is bonded to the adjacent carbonyl group.

A special aspect of the compounds of aspect 5 according to this invention refers to those compounds according to aspect 5, in which
Rb is bisubstituted by Rba and Rbb, and is phenyl, in which
Rba is attached in the meta position with respect to the binding position in which said phenyl ring is bonded to the adjacent carbonyl group,
Rbb is attached in the para position with respect to the binding position in which said phenyl ring is bonded to the adjacent carbonyl group.

A special aspect of the compounds of aspect 5 according to this invention refers to those compounds according to aspect 5, in which
Rb is bisubstituted by Rba and Rbb, and is phenyl, in which
Rba is attached in the meta position with respect to the binding position in which said phenyl ring is bonded to the adjacent carbonyl group,
Rbb is attached in the meta position with respectto the binding position in which said phenyl ring is bonded to the adjacent carbonyl group.

A special aspect of the compounds of aspect 5 according to this invention refers to those compounds according to aspect 5, in which
Rb is substituted by Rba and/or Rbb, and is phenyl, in which
Rba is attached in the meta position with respect to the binding position in which said phenyl ring is bonded to the adjacent carbonyl group, and is 1-C-alkoxy, phenoxy, 3-7C-cycloalkoxy, 3-7C-cycloalkyl-1-4C-alkoxy, 1-4C-alkoxy-2-4C-alkoxy, or phenyl-1-4C-alkoxy,
Rbb is attached in the meta or para position with respect to the binding position in which said phenyl ring is bonded to the adjacent carbonyl group, and is 1-4C-alkoxy, 3-7C-cycloalkoxy, 3-7C-cycloalkyl-1-4C-alkoxy, 1-4C-alkoxy-2-4C-alkoxy, or phenyl-1-4C-alkoxy.

A special aspect of the compounds of aspect 5 according to this invention refers to those compounds according to aspect 5, in which
Rb is substituted by Rba and/or Rbb, and is phenyl, in which
Rba is attached in the meta position with respect-to the binding position in which said phenyl ring is bonded to the adjacent carbonyl group, and is 1-2C-alkoxy, phenoxy, 3-5C-cycloalkoxy, 3-5C-cycloalkyl-1-2C-alkoxy, 1-2C-alkoxy-ethoxy, or phenyl-1-2C-alkoxy,
Rbb is attached in the meta or para position with respect to the binding position in which said phenyl ring is bonded to the adjacent carbonyl group, and is 1-2C-alkoxy, 3-5C-cycloalkoxy, 3-5C-cycloalkyl-1-2C-alkoxy, 1-2C-alkoxy-ethoxy, or phenyl-1-2C-alkoxy.

A special aspect of the compounds of aspect 5 according to this invention refers to those compounds according to aspect 5, in which
Rb is substituted by Rba and/or Rbb, and is phenyl, in which
Rba is halogen, trifluoromethyl, 1-4C-alkyl, 1-4C-alkoxy, or phenoxy,
Rbb is trifluoromethyl, 1-4C-alkyl, or 1-4C-alkoxy.

A special aspect of the compounds of aspect 5 according to this invention refers to those compounds according to aspect 5, in which
Rb is substituted by Rba and/or Rbb, and is phenyl, in which
Rba is chlorine, bromine, fluorine, trifluoromethyl, methyl, methoxy, or phenoxy,
Rbb is trifluoromethyl, methyl, or methoxy.

A special aspect of the compounds of aspect 5 according to this invention refers to those compounds according to aspect 5, in which
Rb is unsubstituted phenyl.

A special aspect of the compounds of aspect 5 according to this invention refers to those compounds according to aspect 5, in which
Rb is 3-chloro-phenyl, 3-methoxy-phenyl, 3,5-dimethoxy-phenyl, 3,4-dimethoxy-phenyl, 3-phenoxy-phenyl, or 3,5-di-trifluoromethyl-phenyl.

A special aspect of the compounds of aspect 5 according to this invention refers to those compounds according to aspect 5, in which
Rb is 3-methoxy-phenyl.

A special aspect of the compounds of aspect 5 according to this invention refers to those compounds according to aspect 5, in which
Rb is 3,5-dimethoxy-phenyl.

A special aspect of the compounds of aspect 5 according to this invention refers to those compounds according to aspect 5, in which
Rb is unsubstituted naphthyl.

Each and every possible combination of the abovementioned special aspects of the compounds of aspect 5 represents a respective further independent special aspect of the compounds according to aspect 5 of this invention.

In a sixth aspect (aspect 6), the present invention relates to the compounds of formula I mentioned in aspect 1 above.

In a seventh aspect (aspect 7) the present invention relates to the use of compounds of formula I, in which, in an independent embodimental alternative,
Ra is —C(O)OR2, in which
R2 is 1-7C-alkyl, such as e.g. methyl, ethyl, propyl, butyl, pentyl or hexyl;

or in which, in another independent embodimental alternative,
Ra is —C(O)OR2, in which
R2 is phenyl, or phenyl mono-substituted by 1-4C-alkoxy;

or in which, in another independent embodimental alternative,
Ra is —C(O)OR2, in which
R2 is 1-4C-alkyl substituted by two hydroxyl radicals;

or in which, in another independent embodimental alternative,
Ra is —C(O)OR2, in which
R2 is 1-4C-alkyl-substituted by R5;

wherein
R5 and Rb are as defined in any compound according to aspect 3 above;

and the salts, solvates and the solvates of the salts thereof;

for the manufacture of pharmaceutical compositions for the treatment, prevention or amelioration of (hyper)proliferative diseases of benign or malignant behaviour, such as e.g. cancer, and/or disorders responsive to the induction of apoptosis in a mammal.

Compounds of aspect 7 more worthy to be mentioned are those compounds of formula I in which, in an independent embodimental alternative,
Ra is —C(O)OR2, in which
R2 is 1-7C-alkyl, such as e.g. methyl, ethyl, propyl, butyl, pentyl or hexyl;

or in which, in another independent embodimental alternative,
Ra is —C(O)OR2, in which
R2 is phenyl, or phenyl mono-substtuted by 1-4C-alkoxy;

or in which, in another independent embodimental alternative,
Ra is —C(O)OR2, in which
R2 is 1-4C-alkyl substituted by two hydroxyl radicals;

or in which, in another independent embodimental alternative,
Ra is —C(O)OR2, in which
R2 is 1-4C-alkyl substituted by R5, in which
R5 is selected from the group consisting of:
  hydroxyl,
  pyridinyl, methylthiazolyl, phenyl, morpholino,
  1-4C-alkoxy, and 1-4C-alkoxy-2-4C-alkoxy;

and in which, in an independent embodimental alternative,
Rb is unsubstituted phenyl;

or in which, in another independent embodimental alternative,
Rb is substituted by Rba and/or Rbb, and is phenyl, in which
Rba is halogen, trifluoromethyl, 1-4C-alkyl, or 1-4C-alkoxy,
Rbb is halogen, trifluoromethyl, 1-4C-alkyl, 1-4C-alkoxy, phenoxy, nitro, hydroxyl, or 1-4C-alkylcarbonyl, or in which, in another independent embodimental alternative,
Rb is unsubstituted naphthyl;

and the salts, solvates and the solvates of the salts thereof.

Compounds of aspect 7 in particular worthy to be mentioned are those compounds of formula I in which, in an independent embodimental alternative,
Ra is —C(O)OR2, in which
R2 is 1-7C-alkyl, such as e.g. methyl, ethyl, propyl, butyl, pentyl or hexyl;

or in which, in another independent embodimental alternative,
Ra is —C(O)OR2, in which
R2 is phenyl, or 4-methoxy-phenyl;

or in which, in another independent embodimental alternative,
Ra is —C(O)OR2, in which
R2 is 1-4C-alkyl substituted by two hydroxyl radicals;

or in which, in another independent embodimental alternative,
Ra is —C(O)OR2, in which
R2 is 1-C-alkyl substituted by R5, in which
R5 is selected from the group consisting of:
  hydroxyl,
  pyridinyl, methylthiazolyl, phenyl, morpholino,
  1-2C-alkoxy, and 1-2C-alkoxy-2-3C-alkoxy;

and in which, in an independent embodimental alternative,
Rb is unsubstituted phenyl;

or in which, in another independent embodimental alternative,
Rb is substituted by Rba and/or Rbb, and is phenyl, in which
Rba is attached in the meta position with respect to the binding position in which said phenyl ring is bonded to the adjacent carbonyl group, and is halogen, trifluoromethyl, 1-4C-alkyl, or 1-4C-alkoxy,
Rbb is attached in the meta or para position with respect to the binding position in which said phenyl ring is bonded to the adjacent carbonyl group, and is halogen, trifluoromethyl, 1-4C-alkyl, 1-4C-alkoxy, phenoxy, hydroxyl, or 1-4C-alkylcarbonyl,
such as e.g. 3-chloro-phenyl, 3-fluoro-phenyl, 3-bromo-phenyl, 4-methyl-phenyl, 3,5-di-trifluoromethyl-phenyl, 4-methoxy-phenyl, 3-methoxy-phenyl, 3,5-dimethoxy-phenyl, 3,4-dimethoxy-phenyl, 3-phenoxy-phenyl, or 4-acetyl-phenyl;

or in which, in another independent embodimental alternative,
Rb is unsubstituted naphthyl;

and the salts, solvates and the solvates of the salts thereof.

In an eighth aspect (aspect 8) the present invention relates to compounds of formula I,
in which
Ra is —C(O)OR2, in which
R2 has one of the meanings as defined in aspect 2, and
Rb has one of the meanings as defined in aspect 2.

In a ninth aspect (aspect 9), which is an embodiment of aspect 8, the present invention relates to the compounds of formula I mentioned in aspect 7.

In a tenth aspect (aspect 10), which is an embodiment of aspect 8, the present invention relates to compounds of formula I,
in which
Ra is —C(O)OR2, in which
either
R2 is 1-7C-alkyl, 3-7C-cycloalkyl, phenyl, pyridyl, or phenyl mono-substituted by 1-4C-alkoxy or 1-4C-alkoxycarbonyl,
or
R2 is 1-7C-alkyl which is substituted by one substituent selected from R5,
or
R2 is 3-4C-alkyl which is substituted by two hydroxyl groups on different carbon atoms,
or
R2 is 1-2C-alkyl which is substituted by 2,2-dimethyl-[1,3]dioxolan-4-yl;
and in which
either
Rb is substituted by Rba and/or Rbb, and is phenyl,
or
Rb is unsubstituted phenyl,
or
Rb is unsubstituted naphthyl;
in which
each R5 is independently selected from the group consisting of:
1-4C-alkoxy, 1-4C-alkoxy-2-4C-alkoxy, (1-4C-alkoxy-2-4C-alkoxy)-2-4C-alkoxy, hydroxyl, 1-4C-alkylcarbonyloxy, phenoxy, phenyl-1-4C-alkoxy, 1-4C-alkoxycarbonyl, carboxyl, amino, mono- or di-1-4C-alkylamino, mono- or di-1-4C-alkylaminocarbonyl, carbamoyl, ureido, guanidino, 1-4C-alkylcarbonylamino, Het, Har and phenyl,
wherein each of said Har or phenyl radicals alone or part of another group may be unsubstituted or optionally substituted by one or two substituents independently selected from halogen, 1-4C-alkoxy, nitro, trifluoromethyl, 1-4C-alkyl, 1-4C-alkoxycarbonyl and carboxyl,
in which
Har is either
a 5-membered monocyclic heteroaryl radical comprising one, two or three heteroatoms independently selected from nitrogen, oxygen and sulphur,
such as e.g. any one selected from furanyl, thiophenyl, pyrrolyl, oxazolyl, isoxazolyl, thiazolyl, isothiazolyl, imidazolyl, pyrazolyl, triazolyl, thiadiazolyl and oxadiazolyl,
or
a 6-membered monocyclic heteroaryl radical comprising one or two nitrogen atoms, such as e.g. any one selected from pyridinyl, pyrazinyl, pyridazinyl and pyrimidinyl,
or
a 9-membered fused bicyclic heteroaryl radical comprising one, two or three heteroatoms independently selected from nitrogen, oxygen and sulphur,
such as e.g. any one selected from indolyl, benzothiophenyl, benzofuranyl, benzoxazoly, benzisoxazolyl, benzothiazolyl, benzoisothiazolyl, benzimidazolyl, indazolyl, benzotriazolyl, benzothiadiazolyl and benzoxadiazolyl,
or
a 10-membered fused bicyclic heteroaryl radical comprising one, two or three heteroatoms independently selected from nitrogen, oxygen and sulphur,
such as e.g. any one selected from quinolinyl, isoquinolinyl, quinoxalinyl, quinazolinyl and cinnolinyl,
whereby said Har radical is attached to the parent molecular group via a ring carbon atom or ring nitrogen atom,
Het is morpholino, piperidino, pyrrolidino, 4N-H-piperazino, 4N-(1-4C-alkyl)-piperazino, thiomorpholino, S-oxo-thiomorpholino or S,S-dioxo-thiomorpholino;
Rba is halogen, trifluoromethyl, 1-4C-alkyl, hydroxyl, nitro, phenoxy or 1-4C-alkoxy,
Rbb is halogen, trifluoromethyl, 1-4C-alkyl or 1-4C-alkoxy;

and the salts, solvates or the solvates of the salts thereof.

Compounds of aspect 10 more worthy to be mentioned are those compounds of formula I,
in which
Ra is —C(O)OR2, in which
either
R2 is 1-6C-alkyl,
or
R2 is phenyl, pyridyl, or phenyl mono-substituted by 1-4C-alkoxy or 1-4C-alkoxycarbonyl,
or
R2 is 1-4C-alkyl which is mono-substituted by R5, in which
R5 is pyridyl, pyrimidinyl, pyrazinyl, indolyl, benzofuranyl, benzothiophenyl, thiazolyl, oxazolyl, 1N-(1-4C-alkyl)- imidazolyl, 1N-(A-4C-alkyl)-pyrazolyl, phenyl, 1-4C-alkoxycarbonyl, carboxyl, mono- or di-1-4C-alkylaminocarbonyl or carbamoyl,
  wherein each of said pyridyl, pyrimidinyl, pyrazinyl, indolyl, benzofuranyl, benzothiophenyl, thiazolyl, oxazolyl, 1N-(1-4C-alkyl)-imidazolyl, 1N-(1-4C-alkyl)-pyrazolyl or phenyl radicals can be unsubstituted or optionally substituted by one or two subsbtuents independently selected from halogen, 1-4C-alkoxy, nitro and 1-4Calkyl, or R2 is 2-4C-alkyl which is mono-substituted by R5, in which
R5 is 1-4C-alkoxy, 1-4C-alkoxy-2-4C-alkoxy, (1-4C-alkoxy-2-4C-alkoxy)-2-4C-alkoxy, hydroxyl, phenyl-1-4C-alkoxy, phenoxy, amino, morpholino, piperidino, pyrrolidino, 4N-(1-4C-alkyl)-piperazino, mono- or di-1-4C-alkylamino, ureido, guanidino, imidazolo, triazolo, pyrazolo, 1-4C-alkylcarbonyloxy or 1-4C-alkylcarbonylamino,
  wherein each of said imidazolo, pyrazolo or phenyl radicals alone or part of another group can be unsubstituted or optionally substituted by one or two substituents independently selected from halogen, 1-4C-alkoxy, nitro and 1-4C-alkyl, or R2 is 3-4C-alkyl which is substituted by two hydroxyl groups on different carbon atoms, or R2 is 1-2C-alkyl which is substituted by 2,2-dimethyl-[1,3]dioxolan4-yl;

and in which either

Rb is unsubstituted phenyl, or

Rb is unsubstituted naphthyl, or

Rb is substituted by Rba and/or Rbb, and is phenyl, in which
Rba is chlorine, fluorine, bromine, trifluoromethyl, methyl, ethyl, methoxy or ethoxy,
Rbb is chlorine, fluorine, bromine, trifluoromethyl, methyl, ethyl, methoxy or ethoxy,
such as e.g. 3-chloro-phenyl, 4-chlorophenyl, 3-fluoro-phenyl, 3-bromo-phenyl, 2-methyl-phenyl, 3-methyl-phenyl, 4-methyl-phenyl, 3,5-di-trifluoromethyl-phenyl, 4-methoxy-phenyl, 3-methoxy-phenyl, 3,5-dimethoxy-phenyl or 3,4-dimethoxy-phenyl;

and the salts, solvates or the solvates of the salts thereof.
  Compounds of aspect 10 in particular worthy to be mentioned are those compounds of formula I, in which
Ra is —C(O)OR2, in which either R2 is methyl, ethyl, propyl or butyl, or R2 is phenyl, pyridyl, (1-2C-alkoxycarbonyl)-phenyl, or (1-2C-alkoxy)-phenyl, or R2 is methyl which is mono-substituted by R5, ethyl which is mono-substituted by R5, or propyl which is mono-substituted by R5, in which
R5 is pyridyl, pyrimidinyl, pyrazinyl, 1N-methyl-imidazolyl, 1N-methyl-pyrazolyl, (methyl)-thiazolyl, phenyl, (1-2C-alkoxy)-phenyl, methoxycarbonyl, ethoxycarbonyl, carboxyl, di-methylaminocarbonyl or carbamoyl, or R2 is ethyl which is mono-substituted by R5, or propyl which is mono-substituted by R5, in which
R5 is methoxy, ethoxy, 2-methoxyethoxy, 2-(2-methoxyethoxy)-ethoxy, hydroxyl, benzyloxy, phenoxy, morpholino, piperidino, pyrrolidino, 4N-(methyl)-piperazino, dimethylamino, imidazolo, triazolo, pyrazolo, methylcarbonyloxy, ethylcarbonyloxy, methylcarbonylamino or ethylcarbonylamino, or R2 is propyl or butyl, each of which is substituted by two hydroxyl groups on different carbon atoms, or R2 is methyl or ethyl, each of which is substituted by 2,2-dimethyl-[1,3]dioxolan-4-yl;

and in which either

Rb is unsubstituted phenyl, or

Rb is substituted by Rba and/or Rbb, and is phenyl, in which
Rba is chlorine, methyl, methoxy or ethoxy,
Rbb is chlorine, methyl, methoxy or ethoxy,
such as e.g. 3-chloro-phenyl, 4-chloro-phenyl, 2-methyl-phenyl, 3-methyl-phenyl, 4-methyl-phenyl, 3-methoxy-phenyl, 4-methoxy-phenyl or 3,5-dimethoxy-phenyl;

and the salts, solvates and the solvates of the salts thereof.
  Compounds of aspect 10 in more particular worthy to be mentioned are those compounds of formula I, in which
Ra is —C(O)OR2, in which either R2 is methyl, ethyl or propyl, or R2 is (R5)-methyl, 2-(R5)-ethyl, or 3-(R5)-propyl, in which
R5 is pyridyl, pyrazinyl or pyrimidinyl, or R2 is 2-(R5)-ethyl, or 3-(R5)-propyl, in which
R5 is methoxy, ethoxy, 2-methoxyethoxy, 2-(2-methoxyethoxy)-ethoxy, hydroxyl, imidazolo, pyrazolo or methylcarbonyloxy, or R2 is 2,3-dihydroxy-propyl;

and in which either

Rb is unsubstituted phenyl, or

Rb is substituted by Rba and/or Rbb, and is phenyl, in which
Rba is attached in the meta position with respect to the binding position in which said phenyl ring is bonded to the adjacent carbonyl group, and is methoxy or ethoxy,
Rbb is attached in the meta or para position with respect to the binding position in which said phenyl ring is bonded to the adjacent carbonyl group, and is methoxy or ethoxy,
such as e.g. 3-methoxy-phenyl, 3,4-dimethoxyphenyl or 3,5-dimethoxy-phenyl;

and the salts, solvates and the solvates of the salts thereof.

Compounds of aspect 10 to be emphasized are those compounds of formula I, in which
Ra is —C(O)OR2, in which either
R2 is ethyl, or
R2 is (R5)-methyl, or 2-(R5)-ethyl, in which
R5 is pyridyl, or
R2 is 2-(R5)-ethyl, in which
R5 is methoxy, 2-methoxyethoxy or hydroxyl, or
R2 is 2,3-dihydroxy-propyl;

and in which
Rb is 3-methoxy-phenyl or 3,5-dimethoxy-phenyl;

and the salts, solvates and the solvates of the salts thereof.

In an eleventh aspect (aspect 11) the present invention relates to the compounds of formula I mentioned in aspect 10 for the manufacture of pharmaceutical compositions for the treatment, prevention or amelioration of (hyper)proliferative diseases of benign or malignant behaviour, such as e.g. cancer, and/or disorders responsive to the induction of apoptosis in a mammal.

Compounds of formula I according to aspect 1 worthy to be noted in the meaning of this invention are those compounds, wherein one or where possible more of the following restrictions (these restrictions constitute a group which will be referred to in the following under "restriction group a") apply:

a.) Ra is —C(O)R1, —C(O)OR2, —C(O)SR2, —C(O)N(R3)R4, or —S(O)$_2$R1;
b.) Rb is optionally substituted by Rba, Rbb and/or Rbc, and is aryl, in which aryl is naphthyl or phenyl;
c.) R1, R2 and R3 may be the same or different and are independently selected from the group consisting of: 1-7C-alkyl, Ar, and Har, wherein each of said 1-7C-alkyl, Ar and Har can be unsubstituted or optionally substituted by at least one substituent independently selected from R5;
d.) R4 is hydrogen;
e.) each R5, Rba, Rbb and Rbc may be the same or different and are independently selected from the group consisting of:
1-7C-alkyl, 3-7C-cycloalkyl, Ar, Har, Het,
halogen, trifluoromethyl, cyano, nitro, guanidino, amidino,
—C(O)R6, —C(O)OR7, —C(O)N(R8)R9, —S(O)$_2$R6,
—N(R10)C(O)R6, —N(R10)C(O)N(R8)R9,
—OC(O)R6,
—OR7, and —N(R8)R(9), wherein each of said 1-7C-alkyl, Ar, Har and Het can be unsubstituted or optionally substituted by at least one substituent independently selected from R11;
f.) R6, R7 and R8 may be the same or different and are independently selected from the group consisting of: hydrogen, 1-7C-alkyl, and Ar, wherein each of said 1-7C-alkyl and Ar can be unsubstituted or optionally substituted by at least one substituent independently selected from R12;
g.) each R9 is independently selected from the group consisting of: hydrogen and 1-7C-alkyl;
h.) each R10 is hydrogen;
i.) R11 is selected from the group consisting of: R5 as defined afore for restriction e.) of this restriction group a.);
j.) R12 is selected from the group consisting of: R5 as defined afore for restriction e.) of this restriction group a.);
k.) each Ar is phenyl;
l.) each Har is independently any fully aromatic mono- or fused bicyclic ring or ring system made up of
a first constituent being a 5- or 6-membered monocyclic unsaturated, aromatic heteroaryl ring A, which heteroaryl ring A comprises one to four heteroatoms independently selected from nitrogen, oxygen and sulfur,
and, optionally, fused to said first constituent,
a second constituent being a benzo group, or any additional heteroaryl ring A as defined herein in restriction l. ),
whereby said Har ring or ring system is attached to the parent molecular group via a substitutable ring carbon or ring nitrogen atom;
m.) each Het is independently any fully saturated or partially unsaturated mono- or fused bicyclic ring or ring system made up of
a first constituent being a 3- or 7-membered monocyclic fully saturated or partially unsaturated, non-aromatic heterocyclic ring B,
which heterocyclic ring B comprises one to three heteroatoms independently selected from nitrogen, oxygen and sulfur,
and which heterocyclic ring B is optionally substituted by one or two oxo groups,
and, optionally, fused to said first constituent,
a second constituent being a benzo group,
whereby said Het ring or ring system is attached to the parent molecular group via a substitutable ring carbon or ring nitrogen atom;

and the salts, solvates or the solvates of the salts thereof.

Compounds of formula I according to aspect 1 further worthy to be noted in the meaning of this invention are those compounds, wherein one or, particularly, where possible more of the following restrictions (these restrictions constitute a group which will be referred to in the following under "restriction group b") apply:

a.) Ra is —C(O)R1;
b.) Ra is —C(O)OR2;
c.) Ra is —C(O)SR2;
d.) Rb is substituted by Rba and/or Rbb and/or Rbc, and is phenyl;
e.) Rb is unsubstituted phenyl;
f.) Rb is unsubstituted naphthyl;
g.) R1 and R2 may be the same or different and are independently selected from the group consisting of: 1-7C-alkyl, and 1-7C-alkyl substituted by at least one substituent selected from R5;
h.) R5, Rba, Rbb and Rbc may be the same or different and are independently selected from the group consisting of:
1-7C-alkyl, 3-7C-cycloalkyl, Ar, Har, Het,
halogen, trifluoromethyl, cyano, nitro, guanidino, amidino,
—C(O)R6, —C(O)OR7, —C(O)N(R8)R9, —S(O)$_2$R6,
—N(R10)C(O)R6, —N(R10)C(O)N(R8)R9,
—OC(O)R6,
—OR7, and —N(R8)R(9), wherein each of said 1-7C-alkyl, Ar, Har and Het can be unsubstituted or optionally substituted by at least one substituent independently selected from R11;
i.) R6, R7 and R8 may be the same or different and are independently selected from the group consisting of: hydrogen, 1-7C-alkyl, and Ar, wherein each of said 1-7C- alkyl and Ar can be unsubstituted or optionally substituted by at least one substituent independently selected from R12;
j.) each R9 is independently selected from the group consisting of: hydrogen and 1-7C-alkyl;
k.) each R10 is hydrogen;
l.) R11 is selected from the group consisting of: R5 as defined afore for restriction h.) of this restriction group b.);
m.) R12 is selected from the group consisting of: R5 as defined afore for restriction h.) of this restriction group b.);
n.) each Ar is phenyl;
o.) each Har is independently any fully aromatic mono- or fused bicyclic ring or ring system made up of
  a first constituent being a 5- or 6-membered monocyclic unsaturated, aromatic heteroaryl ring A, which heteroaryl ring A comprises one to four heteroatoms independently selected from nitrogen, oxygen and sulfur,
  and, optionally, fused to said first constituent,
  a second constituent being a benzo group, or any additional heteroaryl ring A as defined in this restriction o.),
  whereby said Har ring or ring system is attached to the parent molecular group via a substitutable ring carbon or ring nitrogen atom;
p.) each Het is independently any fully saturated or partially unsaturated mono- or fused bicyclic ring or ring system made up of
  a first constituent being a 3- or 7-membered monocyclic fully saturated or partially unsaturated, non-aromatic heterocyclic ring B,
    which heterocyclic ring B comprises one to three heteroatoms independently selected from nitrogen, oxygen and sulfur,
    and which, heterocyclic ring B is optionally substituted by one or two oxo groups,
  and, optionally, fused to said first constituent,
  a second constituent being a benzo group,
  whereby said Het ring or ring system is attached to the parent molecular group via a substitutable ring carbon or ring nitrogen atom;

and the salts, solvates or the solvates of the salts thereof.

In the compounds of formula I according to the present invention, the significances mentioned in the following details\subdetails and/or variants/subvariants are of concern individually or in any possible single or multiple sub-combination of any of said details, subdetails, variants and subvariants:

A first detail (detail a) of the compounds of formula I according to this invention includes those compounds of formula I, in which
Ra is —C(O)R1.

A subdetail (detail a1) of the compounds according to detail a of this invention include those compounds of formula I, in which
Ra is —C(O)R1, in which
R1 is hydrogen, 1-7C-alkyl, 3-7C-cycloalkyl, or
  1-7C-alkyl substituted by any one of R5 as defined in aspect 1 above, or,
  in an embodimental alternative,
  1-7C-alkyl substituted by any one of R5 as defined in restriction e (according to restriction group a) or in restriction h (according to restriction group b) above.

Yet a subdetail (detail a1') of the compounds according to detail a of this invention include those compounds of formula I, in which
Ra is —C(O)R1, in which
R1 is hydrogen, or 1-4C-alkyl, or
  1-4C-alkyl substituted by any one of R5 as defined in aspect 1 above, or,
  in an embodimental alternative,
  1-4C-alkyl substituted by any one of R5 as defined in restriction e (according to restriction group a) or in restriction h (according to restriction group b) above.

Compounds of this detail a1 or a1' may include those compounds according to detail a1, in which
Ra is —C(O)R1, in which
R1 is 1-4C-alkyl substituted by R5, in which
R5 is 1-4C-alkoxycarbonyl, 1-4C-alkylcarbonyl, carbamoyl, guanidine, amidino, carboxyl, mono- or di-1-4C-alkylaminocarbonyl, mono- or di-1-4C-alkylamino, ureido, 1-4C-alkoxy, hydroxyl, 1-4C-alkoxy-2-4C-alkoxy, or phenyl-1-4C-alkoxy.

Compounds of this detail a1 or a1' may further include those compounds according to detail a1, in which
Ra is —C(O)R1, in which
R1 is 1-4C-alkyl substituted by R5, in which
either
R5 is phenyl, or R51-substituted phenyl, in which
R51 is 1-4C-alkoxy, or
R5 is Har, R52-substituted Har, or Het, in which, in a first alternative thereof,
Har is attached to the parent molecular group via any ring carbon or ring nitrogen atom, and is an unsaturated (aromatic) 5-membered ring comprising one to four heteroatoms independently selected from nitrogen, oxygen and sulfur which is optionally fused to a benzene ring, or, in a second alternative thereof,
Har is attached to the parent molecular group via any ring carbon atom, and is an unsaturated (aromatic) 6-membered ring comprising one or two nitrogen atoms independently selected from nitrogen, oxygen and sulfur which is optionally fused to a benzene ring,
R52 is 1-4C-alkyl, or, in a third alternative thereof,
Het is attached to the parent molecular group via any ring nitrogen atom, and is a saturated 3- to 7-membered monocyclic ring comprising one or two heteroatoms independently selected from nitrogen, —N(R53)-, oxygen and sulfur, and which is optionally substituted by one or two oxo groups, or a benzo-fused derivative thereof, in which
R53 is 1-4C-alkyl, or 1-4C-alkylcarbonyl, or, in a fourth alternative thereof,
Het is attached to the parent molecular group via any ring carbon atom, and is a saturated 3- to 7-membered monocyclic ring comprising one or two heteroatoms independently selected from nitrogen, —N(R53)-, oxygen and sulfur, which is optionally substituted by one or two oxo groups, and which is optionally fused to a benzene ring, in which
R53 is 1-4C-alkyl, or 1-4C-alkylcarbonyl;

in an interesting independent embodiment thereof
R1 is 1-4C-alkyl substituted by R5, in which
R5 is Har, or Het, in which, in said first alternative,
Har is indolyl, thiophenyl, N-methyl-imidazolyl, methyl-thiazolyl, or imidazolyl (such as e.g. indol-2-yl, indol-3-yl, thiophen-2-yl, 4-methyl-thiazol-5-yl, 1-N-methyl-imidazol-5-yl, 1-N-methyl-imidazol-4-yl, 1-NH-imidazol4-yl, or imidazol-1-yl), or, in said second alternative,
Har is pyridyl, or pyrazinyl (such as e.g. pyridin-2-yl, pyridin-3-yl, or pyridin-4-yl, or pyrazin-2-yl), or, in said third alternative,
Het is piperidinyl, morpholinyl, N-methyl-piperazinyl, or pyrrolidinyl (such as e.g. piperidin-1-yl, morpholino, 4-N-methyl-piperazin-1-yl, or pyrrolidino-1-yl), or, in said fourth alternative,
Het is 1,3-benzodioxolyl (such as e.g. 1,3-benzodioxol-5-yl);

in another interesting independent embodiment thereof
R1 is 1-4C-alkyl substituted by R5, in which
R5 is Har;

in a further interesting independent embodiment thereof
R1 is 1-4C-alkyl substituted by R5, in which
R5 is Har, in which either
Har is indolyl, thiophenyl, N-methyl-imidazolyl, methyl-thiazolyl, or imidazolyl (such as e.g. indol-2-yl, indol-3-yl, thiophen-2-yl, 4-methyl-thiazol-5-yl, 1-N-methyl-imidazol-5-yl, 1-N-methyl-imidazol-4-yl, 1-NH-imidazol-4-yl, or imidazol-1-yl), or
Har is pyridyl, or pyrazinyl (such as e.g. pyridin-2-yl, pyridin-3-yl, or pyridin4-yl, or pyrazin-2-yl);

in a more interesting independent embodiment thereof
R1 is 1-4C-alkyl, especially ethyl or propyl, substituted by R5, in which
R5 is Har, in which
Har is indolyl (such as e.g. indol-2-yl), thiophenyl (such as e.g. thiophen-2-yl), or methyl-thiazolyl (such as e.g. 4-methyl-thiazol-5-yl).

A more precise subdetail (detail a11) of the compounds according to detail a of this invention include those compounds of formula I, in which
Ra is —C(O)R1, in which
R1 is 1-7C-alkyl, such as e.g. 1-4C-alkyl, substituted by R5, in which
R5 is 1-4C-alkoxycarbonyl, 1-4C-alkylcarbonyl, carbamoyl, 1-4C-alkoxy, 3-7C-cycloalkoxy, 3-7C-cycloalkyl-1-4C-alkoxy, or 1-4C-alkoxy-2-4c-alkoxy;

in an interesting idependent embodiment thereof
R1 is 1-4C-alkyl, such as e.g. ethyl, substituted by R5, in which;
R5 is carbamoyl, 1-4C-alkoxy, 1-4C-alkoxycarbonyl, or 1-4C-alkylcarbonyl;

in a more interesting independent embodiment thereof
R1 is 1-4C-alkyl, especially ethyl, substituted by R5, in which
R5 is carbamoyl, methoxy, methoxycarbonyl, or acetyl.

Yet a more precise subdetail (detail a11') of the compounds according to detail a of this invention include those compounds of formula I, in which
Ra is —C(O)R1, in which
R1 is 1-4C-alkyl substituted by R5, in which
R5 is 1-4C-alkoxycarbonyl, 1-4C-alkylcarbonyl, carbamoyl, 1-4C-alkoxy, 3-7C-cycloalkoxy, 3-7C-cycloalkyl-1-4C-alkoxy, or 1-4C-alkoxy-2-4C-alkoxy;

in an interesting independent embodiment thereof
R1 is 1-4C-alkyl, such as e.g. ethyl, substituted by R5, in which
R5 is carbamoyl, 1-4C-alkoxy, 1-4C-alkoxycarbonyl, or 1-4C-alkylcarbonyl;

in a more interesting independent embodiment thereof
R1 is 1-4C-alkyl, especially ethyl, substituted by R5, in which
R5 is carbamoyl, methoxy, methoxycarbonyl, or acetyl.

Another more precise subdetail (detail a12) of the compounds according to detail a of this invention include those compounds of formula I, in which
Ra is —C(O)R1, in which
R1 is 1-7C-alkyl substituted by R5, in which
R5 is optionally substituted by at least one substituent R11, and is Har, in which
Har has one of the meanings as defined in aspect 1 above,
each R11 is independently selected from the group consisting of: R5 as defined in aspect 1 above;

in an interesting independent embodiment thereof
Har is unsubstituted;

in another interesting independent embodiment thereof
Har is a 5-membered monocyclic unsaturated, aromatic heteroaryl ring comprising one to four heteroatoms independently selected from nitrogen, oxygen and sulfur which is optionally fused to a benzene ring, such as e.g. thiophenyl or indolyl;

in yet another interesting independent embodiment thereof
Har is unsubstituted, and a 5-membered monocyclic unsaturated, aromatic heteroaryl ring comprising one to four heteroatoms independently selected from nitrogen, oxygen and sulfur which is optionally fused to a benzene ring, such as e.g. thiophenyl or indolyl;

in a further interesting independent embodiment thereof
R1 is 1-4C-alkyl, especially ethyl or propyl, substituted by R5, in which
R5 is unsubstituted Har, in which
Har is indolyl, or thiophenyl, such as e.g. indol-2-yl, or thiophen-2-yl.

Yet another more precise subdetail (detail a12') of the compounds according to detail a of this invention include those compounds of formula I, in which
Ra is —C(O)R1, in which
R1 is substituted by R5, and is methyl, ethyl, propyl or butyl, in which
R5 is optionally substituted by at least one substituent R11, and is Har, in which
Har has one of the meanings as defined in aspect 1 above,
each R11 is independently selected from the group consisting of: R5 as defined in aspect 1 above;

in an interesting independent embodiment thereof
Har is unsubstituted;

in another interesting independent embodiment thereof

Har is a 5-membered monocyclic unsaturated, aromatic heteroaryl ring comprising one to four heteroatoms independently selected from nitrogen, oxygen and sulfur which is optionally fused to a benzene ring, such as e.g. thiophenyl or indolyl;

in yet another interesting independent embodiment thereof

Har is unsubstituted, and a 5-membered monocyclic unsaturated, aromatic heteroaryl ring comprising one to four heteroatoms independently selected from nitrogen, oxygen and sulfur which is optionally fused to a benzene ring, such as e.g. thiophenyl or indolyl;

in a further interesting independent embodiment thereof

R1 is 1-4C-alkyl, especially ethyl or propyl, substituted by R5, in which

R5 is unsubstituted Har, in which

Har is indolyl, or thiophenyl, such as e.g. indol-2-yl, or thiophen-2-yl.

Another more precise subdetail (detail a13) of the compounds according to detail a of this invention include those compounds of formula I, in which Ra is —C(O)R1, in which R1 is 1-7C-alkyl, 3-7C-cycloalkyl, or 3-7C-cycloalkyl-1-4C-alkyl;

in an interesting independent embodiment thereof

R1 is 1-7C-alkyl; or in a more interesting independent embodiment thereof

R1 is methyl, propyl, or hexyl.

Yet another more precise subdetail (detail a13') of the compounds according to detail a of this invention include those compounds of formula I, in which Ra is —C(O)R1, in which R1 is 1-4C-alkyl;

in an interesting independent embodiment thereof

R1 is methyl, ethyl, propyl or butyl; or in a more interesting independent embodiment thereof R1 is methyl or propyl.

A notable subdetail (detail a14) of the compounds according to detail a of this invention include those compounds of formula I, in which Ra is —C(O)R1, in which R1 is (R5)-methyl, 2-(R5)-ethyl, or 3-(R5)-propyl, in which R5 is pyridyl, pyrimidinyl, pyrazinyl, imidazolo or pyrazolo.

Another notable subdetail (detail a15) of the compounds according to detail a of this invention include those compounds of formula I, in which Ra is —C(O)R1, in which R1 is (R5)-methyl, 2-(R5)-ethyl, or 3-(R5)-propyl, in which R5 is methoxy, ethoxy, 2-methoxyethoxy, 2-(2-methoxyethoxy)ethoxy, hydroxyl or methylcarbonyloxy.

A more notable subdetail (detail a16) of the compounds according to detail a of this invention include those compounds of formula I, in which Ra is —C(O)R1, in which R1 is any one selected from methoxy-methyl, 2-methoxyethyl, (2-methoxyethoxy)-methyl, 2-(2-methoxyethoxy)-ethyl, hydroxy-methyl, 2-hydroxy-ethyl, (pyridin-2-yl)-methyl, (pyridin-3-yl)-methyl, (pyridin4-yl)-methyl, 2-(pyridin-2-yl)-ethyl, 2-(pyridin-3-yl)-ethyl and 2-(pyridin4-yl)ethyl.

Another more notable subdetail (detail a17) of the compounds according to detail a of this invention include those compounds of formula I, in which Ra is —C(O)R1, in which R1 is 2,3-dihydroxypropyl.

A second detail (detail b) of the compounds of formula I according to this invention includes those compounds of formula I, in which Ra is —C(O)OR2.

A subdetail (detail b1) of the compounds according to detail b of this invention include those compounds of formula I, in which Ra is —C(O)OR2, in which R2 is 1-7C-alkyl, or 3-7C-cycloalkyl, or 1-7C-alkyl substituted by any one of R5 as defined in aspect 1 above, or, in an embodimental alternative, 1-7C-alkyl substituted by any one of R5 as defined in restriction e (according to restriction group a) or in restriction h (according to restriction group b) above.

Compounds of this detail b1 may include those compounds according to detail b1, in which Ra is —C(O)OR2, in which R2 is 1-4C-alkyl substituted by R5, in which R5 is 1-4C-alkoxycarbonyl, 1-4C-alkylcarbonyl, carbamoyl, guanidino, amidino, carboxyl, mono- or di-1-4C-alkylaminocarbonyl, mono- or di-1-4C-alkylamino, ureido, 1-4C-alkoxy, hydroxyl, 1-4C -alkoxy-2-4C-alkoxy, or phenyl-1-4C-alkoxy.

Compounds of this detail b1 may further include those compounds according to detail b1, in which Ra is —C(O)OR2, in which R2 is 1-4C-alkyl substituted by R5, in which either R5 is phenyl, or R51-substituted phenyl, in which R51 is 1-4C-alkoxy, or R5 is Har, R52-substituted Har, or Het, in which, in a first alternative thereof, Har is attached to the parent molecular group via any ring carbon or ring nitrogen atom, and is an unsaturated (aromatic) 5-membered ring comprising one to four heteroatoms independently selected from nitrogen, oxygen and sulfur which is optionally fused to a benzene ring, or, in a second alternative thereof, Har is attached to the parent molecular group via any ring carbon atom, and is an unsaturated (aromatic) 6-membered ring comprising one or two nitrogen atoms independently selected from nitrogen, oxygen and sulfur which is optionally fused to a benzene ring, R52 is 1-4C-alkyl, or, in a third alternative thereof, Het is attached to the parent molecular group via any ring nitrogen atom, and is a saturated 3- to 7-membered monocyclic ring comprising one or two heteroatoms independently selected from nitrogen, —N(R53)-, oxygen and sulfur, and which is optionally substituted by one or two oxo groups, or a benzo-fused derivative thereof, in which R53 is 1-4C-alkyl, or 1-4C-alkylcarbonyl, or, in a fourth alternative thereof, Het is attached to the parent molecular group via any ring carbon atom, and is a saturated 3- to 7-membered monocyclic ring comprising one or two heteroatoms independently selected from nitrogen, —N(R53)—, oxygen and sulfur, which is optionally substituted by one or two oxo groups, and which is optionally fused to a benzene ring, in which R53 is 1-4C-alkyl, or 1-4C-alkylcarbonyl;

in an interesting independent embodiment thereof
R1 is 1-4C-alkyl substituted by R5, in which
R5 is Har, or Het, in which, in said first alternative,
Har is indolyl, thiophenyl, N-methyl-imidazolyl, methyl-thiazolyl, or imidazolyl (such as e.g. indol-2-yl, indol-3-yl, thiophen-2-yl, 4-methyl-thiazol-5-yl, 1-N-methyl-imidazol-5-yl, 1-N-methyl-imidazol-4-yl, 1-NH-imidazol4-yl, or imidazol-1-yl), or, in said second alternative,
Har is pyridyl, or pyrazinyl (such as e.g. pyridin-2-yl, pyridin-3-yl, or pyridin4-yl, or pyrazin-2-yl), or, in said third alternative,
Het is piperidinyl, morpholinyl, N-methyl-piperazinyl, or pyrrolidinyl (such as e.g. piperidin-1-yl, morpholino, 4-N-methyl-piperazin-1-yl, or pyrrolidino-1-yl), or, in said fourth alternative,
Het is 1,3-benzodioxolyl (such as e.g. 1,3-benzodioxol-5-yl);

in a more interesting independent embodiment thereof
R1 is ethyl substituted by R5, in which
R5 is Har, in which
Har is methyl-thiazolyl (such as e.g. 4-methyl-thiazol-5-yl).

A more precise subdetail (detail b11) of the compounds according to detail b of this invention include those compounds of formula I, in which
Ra is —C(O)OR2, in which
R2 is 1-7C-alkyl, such as e.g. 2-4C-alkyl, substituted by R5, in which R5 is 1-4C-alkoxycarbonyl, 1-4C-alkoxy, 3-7C-cycloalkoxy, 3-7C-cycloalkyl-1-4C-alkoxy, or 1-4C-alkoxy-2-4C-alkoxy;

in an interesting independent embodiment thereof
R1 is 1-4C-alkyl, especially ethyl, substituted by R5, in which
R5 is 1-4C-alkoxy;

in a more interesting independent embodiment thereof
R1 is ethyl substituted by R5, in which
R5 is methoxy.

Another more precise subdetail (detail b12) of the compounds according to detail b of this invention include those compounds of formula I, in which
Ra is —C(O)OR2, in which
R1 is 1-7C-alkyl substituted by R5, in which R5 is optionally substituted by at least one substituent R11, and is Har, in which
Har has one of the meanings as defined in aspect 1 above, each R11 is independently selected from the group consisting of: R5 as defined in aspect 1 above;

in an interesting independent embodiment thereof
Har is unsubstituted;

in another interesting independent embodiment thereof
Har is a 5-membered monocyclic unsaturated, aromatic heteroaryl ring comprising one to four heteroatoms independently selected from nitrogen, oxygen and sulfur which is optionally fused to a benzene ring, such as e.g. thiophenyl or indolyl;

in yet another interesting independent embodiment thereof
Har is unsubstituted, and a 5-membered monocyclic unsaturated, aromatic heteroaryl ring comprising one to four heteroatoms independently selected from nitrogen, oxygen and sulfur which is optionally fused to a benzene ring, such as e.g. thiazolyl;

in a further interesting independent embodiment thereof
R1 is 1-4C-alkyl, especially ethyl or propyl, substituted by R5, in which
R5 is Har, in which
Har is methyl-thiazolyl (such as e.g. 4-methyl-thiazol-5-yl).

Another more precise subdetail (detail b13) of the compounds according to detail b of this invention include those compounds of formula I, in which
Ra is —C(O)OR2, in which
R2 is 1-7C-alkyl, 3-7C-cycloalkyl, or 3-7C-cycloalkyl-1-4C-alkyl;

in an interesting independent embodiment thereof
R2 is 1-7C-alkyl;

in a more interesting independent embodiment thereof
R2 is methyl, ethyl, tertbutyl, or pentyl, particularly ethyl.

Yet another more precise subdetail (detail b13') of the compounds according to detail b of this invention include those compounds of formula I, in which
Ra is —C(O)OR2, in which
R2 is 1-7C-alkyl;

in an interesting independent embodiment thereof
R2 is methyl, ethyl, propyl, butyl, pentyl or hexyl;

in a more interesting independent embodiment thereof
R2 is methyl, ethyl, propyl or butyl;

in a particular interesting independent embodiment thereof
R2 is ethyl.

A notable subdetail (detail b14) of the compounds according to detail b of this invention include those compounds of formula I, in which
Ra is —C(O)OR2, in which
R2 is (R5)-methyl, 2-(R5)-ethyl, or 3-(R5)-propyl, in which
R5 is pyridyl, pyrimidinyl or pyrazinyl.

Another notable subdetail (detail b15) of the compounds according to detail b of this invention include those compounds of formula I, in which
Ra is —C(O)OR2, in which
R2 is 2-(R5)-ethyl, or 3-(R5)-propyl, in which R5 is methoxy, ethoxy, 2-methoxyethoxy, 2-(2-methoxy-ethoxy)ethoxy, hydroxyl or methylcarbonyloxy.

A more notable subdetail (detail b16) of the compounds according to detail b of this invention include those compounds of formula I, in which
Ra is —C(O)OR2, in which
R2 is any one selected from 2-methoxy-ethyl, 2-(2-methoxy-ethoxy)-ethyl, 2-hydroxy-ethyl, (pyridin-2-yl)-methyl, (pyridin-3-yl)-methyl, (pyridin4-yl)-methyl, 2-(pyridin-2-yl)-ethyl, 2-(pyridin-3-yl)-ethyl and 2-(pyridin4-yl)-ethyl.

Another more notable subdetail (detail b17) of the compounds according to detail b of this invention include those compounds of formula I, in which
Ra is —C(O)OR2, in which
R2 is 2,3-dihydroxypropyl.

Another more notable subdetail (detail b18) of the compounds according to detail b of this invention include those compounds of formula I, in which
Ra is —C(O)OR2, in which
R2 is ethyl.

A third detail (detail c) of the compounds of formula I according to this invention includes those compounds of formula I, in which
Ra is —C(O)SR2.

A notable subdetail (detail c1) of the compounds according to detail c of this invention include those compounds of formula I, in which
Ra is —C(O)SR2, in which
R2 is methyl, ethyl, propyl or butyl.

Another notable subdetail (detail c2) of the compounds according to detail c of this invention include those compounds of formula I, in which
Ra is —C(O)SR2, in which
R2 is (R5)-methyl, 2-(R5)-ethyl, or 3-(R5)-propyl, in which R5 is pyridyl, pyrimidinyl or pyrazinyl.

Another notable subdetail (detail c3) of the compounds according to detail c of this invention include those compounds of formula I, in which
Ra is —C(O)SR2, in which
R2 is 2-(R5)-ethyl, or 3-(R5)-propyl, in which
R5 is methoxy, ethoxy, 2-methoxyethoxy, 2-(2-methoxy-ethoxy)ethoxy, hydroxyl or methylcarbonyloxy.

A more notable subdetail (detail c4) of the compounds according to detail c of this invention include those compounds of formula I, in which
Ra is —C(O)SR2, in which
R2 is any one selected from methyl, ethyl and propyl.

Another more notable subdetail (detail c5) of the compounds according to detail c of this invention include those compounds of formula I, in which
Ra is —C(O)SR2, in which
R2 is any one selected from 2-methoxy-ethyl, 2-(2-methoxy-ethoxy)-ethyl, 2-hydroxy-ethyl, (pyridin-2-yl)-methyl, (pyridin-3-yl)-methyl, (pyridin4-yl)-methyl, 2-(pyridin-2-yl)-ethyl, 2-(pyridin-3-yl)-ethyl and 2-(pyridin4-yl)-ethyl.

A first variant (variant a) of the compounds of formula I according to this invention includes those compounds of formula I, in which
Rb is optionally substituted by Rba and/or Rbb and/or Rbc, and is aryl, in which
aryl is naphthyl or phenyl.

A subvariant (variant a1) of the compounds according to variant a of this invention includes those compounds of formula I, in which
Rb is optionally substituted by Rba and/or Rbb and/or Rbc, and is phenyl, in which
Rba, Rbb and Rbc have independently one of the meanings as defined in aspect 1 above, or, in an independent embodimental alternative,
Rba, Rbb and Rbc have independently one of the meanings as defined in restriction e (according to restriction group a) or in restriction h (according to restriction group b) above.

A further subvariant (variant a1l1) of the compounds according to variant a of this invention includes those compounds of formula I, in which
Rb is substituted by Rba and/or Rbb and/or Rbc, and is phenyl, in which
Rba is 1-4C-alkyl, 3-7C-cycloalkyl,
halogen, trifluoromethyl, nitro, cyano,
1-4C-alkylcarbonyl, 1-4C-alkoxycarbonyl, carboxyl, mono- or di-1-4C-alkylaminocarbonyl, carbamoyl, 1-4C-alkylcarbonylamino, 1-4C-alkylsulfonylamino, 3-7C-cycloalkylcarbonylamino, 3-7C-cycloalkylsulfonylamino,
hydroxyl, 1-4C-alkoxy, 3-7C-cycloalkoxy, phenoxy,
amino, mono- or di-1-4C-alkylamino,
3-7C-cycloalkyl-1-4C-alkyl, 1-4C-alkoxy-1-4C-alkyl, hydroxy-1-4C-alkyl, 3-7C-cycloalkyl-1-4C-alkoxy, 1-4C-alkoxy-2-4C-alkoxy, hydroxy-2-4C-alkoxy, phenyl-1-4C-alkoxy, or completely or predominantly fluorine-substituted 1-4C-alkoxy,
Rbb is halogen, 1-4C-alkyl, trifluoromethyl, nitro,
hydroxyl, 1-4C-alkoxy, 3-7C-cycloalkoxy, phenoxy,
3-7C-cycloalkyl-1-4C-alkoxy, 1-4C-alkoxy-2-4C-alkoxy, hydroxy-2-4C-alkoxy, phenyl-1-4C-alkoxy, or completely or predominantly fluorine-substituted 1-4C-alkoxy,
Rbc is 1-4C-alkoxy.

A further subvariant (variant a111) of the compounds according to variant a of this invention includes those compounds of formula I, in which
Rb is substituted by Rba and/or Rbb and/or Rbc, and is phenyl, in which
Rba is 1-4C-alkyl, 3-7C-cycloalkyl,
halogen, trifluoromethyl, cyano,
1-4C-alkylcarbonyl,
hydroxyl, 1-4C-alkoxy, 3-7C-cycloalkoxy, phenoxy,
di-1-4C-alkylamino, 3-7C-cycloalkyl-1-4C-alkyl, 1-4C-alkoxy-1-4C-alkyl, hydroxy-1-4C-alkyl, 3-7C-cycloalkyl-1-4C-alkoxy, 1-4C-alkoxy-2-4C-alkoxy, hydroxy-2-4C-alkoxy, phenyl-1-4C-alkoxy, or completely or predominantly fluorine-substituted 1-4C-alkoxy, Rbb is halogen, 1-4C-alkyl, trifluoromethyl, hydroxyl, 1-4C-alkoxy, 3-7C-cycloalkoxy, phenoxy, 3-7C-cycloalkyl-1-4C-alkoxy, 1-4C-alkoxy-2-4C-alkoxy, hydroxy-2-4C-alkoxy, phenyl-1-4C-alkoxy, or completely or predominantly fluorine-substituted 1-4C-alkoxy, Rbc is 1-4C-alkoxy.

A further subvariant (variant a112) of the compounds according to variant a of this invention includes those compounds of formula I, in which
Rb is substituted by Rba and/or Rbb, and is phenyl, in which
Rba is halogen, trifluoromethyl,
hydroxyl, 1-4C-alkoxy, 3-7C-cycloalkoxy, phenoxy, 3-7C-cycloalkyl-1-4C-alkoxy, 1-4C-alkoxy-2-4C-alkoxy, hydroxy-2-4C-alkoxy, phenyl-1-4C-alkoxy, or completely or predominantly fluorine-substituted 1-4C-alkoxy, Rbb is trifluoromethyl, hydroxyl, 1-4C-alkoxy, 3-7C-cycloalkoxy, phenoxy, 3-7C-cycloalkyl-1-4C-alkoxy, 1-4C-alkoxy-2-4C-alkoxy, hydroxy-2-4C-alkoxy, phenyl-1-4C-alkoxy, or completely or predominantly fluorine-substituted 1-4C-alkoxy.

A further subvariant (variant a113) of the compounds according to variant a of this invention includes those compounds of formula I, in which
Rb is substituted by Rba and/or Rbb, and is phenyl, in which
Rba is hydroxyl, 1-4C-alkoxy, 3-7C-cycloalkoxy, phenoxy, 3-7C-cycloalkyl-1-4C-alkoxy, 1-4C-alkoxy-2-4C-alkoxy, hydroxy-2-4C-alkoxy, phenyl-1-4C-alkoxy, or completely or predominantly fluorine-substituted 1-4C-alkoxy, Rbb is 1-4C-alkoxy, 3-7C-cycloalkoxy, 3-7C-cycloalkyl-1-4C-alkoxy, 1-4C-alkoxy-2-4C-alkoxy, phenyl-1-4C-alkoxy, or completely or predominantly fluorine-substituted 1-4C-alkoxy.

A further subvariant (variant a114) of the compounds according to variant a of this invention includes those compounds of formula I, in which
Rb is substituted by Rba and/or Rbb, and is phenyl, in which
Rba is 1-4C-alkoxy, 3-5C-cycloalkoxy, phenoxy, 3-5C-cycloalkylmethoxy, 1-4C-alkoxy-2-4C-alkoxy, or phenyl-1-4C-alkoxy, Rbb is 1-4C-alkoxy, 3-5C-cycloalkoxy, 3-5C-cycloalkylmethoxy, 1-4-C-alkoxy-2-4C-alkoxy, or phenyl-1-4C-alkoxy.

A further subvariant (variant a115) of the compounds according to variant a of this invention includes those compounds of formula I, in which
Rb is substituted by Rba and/or Rbb, and is phenyl, in which
Rba is halogen, 1-4C-alkyl, trifluoromethyl, 1-4C-alkoxy, phenoxy, or 1-4C-alkylcarbonyl, Rbb is halogen, 1-4C-alkyl, trifluoromethyl, 1-4C-alkoxy, phenoxy, or 1-4C-alkylcarbonyl.

A further subvariant (variant a116) of the compounds according to variant a of this invention includes those compounds of formula I, in which
Rb is substituted by Rba and/or Rbb, and is phenyl, in which
Rba is halogen, 1-4C-alkyl, trifluoromethyl, 1-4-C-alkoxy, phenoxy, or 1-4C-alkylcarbonyl, Rbb is halogen, 1-4C-alkyl, trifluoromethyl, or 1-4C-alkoxy.

A further subvariant (variant a117) of the compounds according to variant a of this invention includes those compounds of formula I, in which
Rb is substituted by Rba and/or Rbb, and is phenyl, in which
Rba is halogen, 1-2C-alkyl, trifluoromethyl, 1-2C-alkoxy, phenoxy, or 1-2C-alkylcarbonyl, Rbb is 1-2C-alkyl, trifluoromethyl, or 1-2C-alkoxy.

A further subvariant (variant a118) of the compounds according to variant a of this invention includes those compounds of formula I, in which
Rb is substituted by Rba and/or Rbb, and is phenyl, in which
Rba is chlorine, fluorine, bromine, 1-2C-alkyl, trifluoromethyl, 1-2C-alkoxy, or phenoxy, Rbb is 1-2C-alkyl, trifluoromethyl, or 1-2C-alkoxy.

A further subvariant (variant a119) of the compounds according to variant a of this invention includes those compounds of formula I, in which
Rb is substituted by Rba and/or Rbb, and is phenyl, in which
Rba is chlorine, fluorine, bromine, 1-2C-alkyl, trifluoromethyl, or 1-2C-alkoxy, Rbb is 1-2C-alkyl, trifluoromethyl, or 1-2C-alkoxy.

Another subvariant (variant a12) of the compounds according to variant a of this invention includes those compounds of formula I, in which
Rb is substituted by Rba and/or Rbb, and is phenyl, in which
Rba is attached in the meta position with respect to the binding position in which said phenyl ring is bonded to the adjacent carbonyl group, Rbb is attached in the para position with respect to the binding position in which said phenyl ring is bonded to the adjacent carbonyl group.

A further subvariant (variant a121) of the compounds according to variant a of this invention includes those compounds of formula I, in which
Rb is substituted by Rba and/or Rbb, and is phenyl, in which Rba is attached in the meta position with respect to the binding position in which said phenyl ring is bonded to the adjacent carbonyl group, and is halogen, 1-4C-alkyl, trifluoromethyl, 1-4C-alkoxy, or phenoxy, Rbb is attached in the para position with respect to the binding position in which said phenyl ring is bonded to the adjacent carbonyl group, and is 1-4C-alkyl, 1-4C-alkylcarbonyl, or 1-4C-alkoxy.

A further subvariant (variant a122) of the compounds according to variant a of this invention includes those compounds of formula I, in which Rb is substituted by Rba and/or Rbb, and is phenyl, in which Rba is attached in the meta position with respect to the binding position in which said phenyl ring is bonded to the adjacent carbonyl group, and is chlorine, bromine, fluorine, methyl, trifluoromethyl, methoxy, or phenoxy, Rbb is attached in the para position with respect to the binding position in which said phenyl ring is bonded to the adjacent carbonyl group, and is methyl, acetyl, or methoxy.

Another subvariant (variant a13) of the compounds according to variant a of this invention includes those compounds of formula I, in which Rb is substituted by Rba and/or Rbb, and is phenyl, in which Rba is attached in the meta position with respect to the binding position in which said phenyl ring is bonded to the adjacent carbonyl group, Rbb is attached in the meta position with respect to the binding position in which said phenyl ring is bonded to the adjacent carbonyl group.

A further subvariant (variant a131) of the compounds according to variant a of this invention includes those compounds of formula I, in which Rb is substituted by Rba and/or Rbb, and is phenyl, in which Rba is attached in the meta position with respect to the binding position in which said phenyl ring is bonded to the adjacent carbonyl group, and is halogen, 1-4C-alkyl, trifluoromethyl, 1-4C-alkoxy, or phenoxy, Rbb is attached in the meta position with respect to the binding position in which said phenyl ring is bonded to the adjacent carbonyl group, and is trifluoromethyl, or 1-4C-alkoxy.

A further subvariant (variant a132) of the compounds according to variant a of this invention includes those compounds of formula I, in which Rb is substituted by Rba and/or Rbb, and is phenyl, in which Rba is attached in the meta position with respect to the binding position in which said phenyl ring is bonded to the adjacent carbonyl group, and is chlorine, bromine, fluorine, methyl, trifluoromethyl, methoxy, or phenoxy, Rbb is attached in the meta position with respect to the binding position in which said phenyl ring is bonded to the adjacent carbonyl group, and is trifluoromethyl, or methoxy.

Another subvariant (variant a14) of the compounds according to variant a of this invention includes those compounds of formula I, Rb is substituted by Rba and/or Rbb, and is phenyl, in which Rba is attached in the meta position with respect to the binding position in which said phenyl ring is bonded to the adjacent carbonyl group, Rbb is attached in the meta or para position with respect to the binding position in which said phenyl ring is bonded to the adjacent carbonyl group.

A further subvariant (variant a141) of the compounds according to variant a of this invention includes those compounds of formula I, in which Rb is substituted by Rba and/or Rbb, and is phenyl, in which Rba is attached in the meta position with respect to the binding position in which said phenyl ring is bonded to the adjacent carbonyl group, and is halogen, trifluoromethyl, 1-4C-alkyl, 1-4C-alkoxy, phenoxy, 3-7C-cycloalkoxy, 3-7C-cycloalkyl-1-4C-alkoxy, 1-4C-alkoxy-2-4C-alkoxy, or phenyl-1-4C-alkoxy, Rbb is attached in the meta or para position with respect to the binding position in which said phenyl ring is bonded to the adjacent carbonyl group, and is trifluoromethyl, 1-4C-alkyl, 1-4C-alkoxy, 3-7C-cycloalkoxy, 3-7C-cycloalkyl-1-4C-alkoxy, 1-4C-alkoxy-2-4C-alkoxy, or phenyl-1-4C-alkoxy.

A further subvariant (variant a142) of the compounds according to variant a of this invention includes those compounds of formula I, in which Rb is monosubstituted by Rba, or bisubstituted by Rba and Rbb, and is phenyl, in which Rba is attached in the meta position with respect to the binding position in which said phenyl ring is bonded to the adjacent carbonyl group, and is halogen, trifluoromethyl, 1-4C-alkyl, 1-4C-alkoxy, phenoxy, 3-7C-cycloalkoxy, 3-7C-cycloalkyl-1-4C-alkoxy, 1-4C-alkoxy-2-4C-alkoxy, or phenyl-1-4C-alkoxy, Rbb is attached in the para or, particularly, meta position with respect to the binding position in which said phenyl ring is bonded to the adjacent carbonyl group, and is trifluoromethyl, 1-4C-alkyl, 1-4C-alkoxy, 3-7C-cycloalkoxy, 3-7C-cycloalkyl-1-4C-alkoxy, 1-4C-alkoxy-2-4C-alkoxy, or phenyl-1-4C-alkoxy.

A further subvariant (variant a143) of the compounds according to variant a of this invention includes those compounds of formula I, in which Rb is substituted by Rba and/or Rbb, and is phenyl, in which Rba is attached in the meta position with respect to the binding position in which said phenyl ring is bonded to the adjacent carbonyl group, and is chlorine, bromine, fluorine, trifluoromethyl, 1-2C-alkyl, 1-2C-alkoxy, or phenoxy, Rbb is attached in the meta or para position with respect to the binding position in which said phenyl ring is bonded to the adjacent carbonyl group, and is trifluoromethyl, 1-2C-alkyl, or 1-2C-alkoxy.

A further subvariant (variant a144) of the compounds according to variant a of this invention includes those compounds of formula I, in which
Rb is monosubstituted by Rba, or bisubstituted by Rba and Rbb, and is phenyl, in which
Rba is attached in the meta position with respect to the binding position in which said phenyl ring is bonded to the adjacent carbonyl group, and is chlorine, bromine, fluorine, trifluoromethyl, 1-2C-alkyl, 1-2C-alkoxy, or phenoxy,
Rbb is attached in the para or, particularly, meta position with respect to the binding position in which said phenyl ring is bonded to the adjacent carbonyl group, and is trifluoromethyl, 1-2C-alkyl, or 1-2C-alkoxy.

Another subvariant (variant a15) of the compounds according to variant a of this invention includes those compounds of formula I,
Rb is monosubstituted by Rba, and is phenyl, in which
Rba is attached in the meta position with respect to the binding position in which said phenyl ring is bonded to the adjacent carbonyl group.

Another subvariant (variant a151) of the compounds according to variant a of this invention includes those compounds of formula I,
Rb is bisubstituted by Rba and Rbb, and is phenyl, in which
Rba is attached in the meta position with respect to the binding position in which said phenyl ring is bonded to the adjacent carbonyl group,
Rba is attached in the para position with respect to the binding position in which said phenyl ring is bonded to the adjacent carbonyl group.

Another subvariant (variant a152) of the compounds according to variant a of this invention includes those compounds of formula I,
Rb is bisubstituted by Rba and Rbb, and is phenyl, in which
Rba is attached in the meta position with respect to the binding position in which said phenyl ring is bonded to the adjacent carbonyl group,
Rba is attached in the meta position with respect to the binding position in which said phenyl ring is bonded to the adjacent carbonyl group.

Another subvariant (variant a16) of the compounds according to variant a of this invention includes those compounds of formula I, in which
Rb is substituted by Rba and/or Rbb, and is phenyl, in which
Rba is chlorine, fluorine, bromine, methyl, trifluoromethyl, methoxy, phenoxy or methylcarbonyl,
Rbb is methyl, trifluoromethyl, or methoxy.

A further subvariant (variant a161) of the compounds according to variant a of this invention includes those compounds of formula I, in which
Rb is substituted by Rba and/or Rbb, and is phenyl, in which
Rba is chlorine, fluorine, bromine, methyl, trifluoromethyl, methoxy or phenoxy,
Rbb is methyl, trifluoromethyl, or methoxy.

A further subvariant (variant a162) of the compounds according to variant a of this invention includes those compounds of formula I, in which
Rb is substituted by Rba and/or Rbb, and is phenyl, in which
Rba is chlorine, fluorine, bromine, methyl, trifluoromethyl or methoxy,
Rbb is methyl, trifluoromethyl, or methoxy.

Another subvariant (variant a17) of the compounds according to variant a of this invention includes those compounds of formula I,
Rb is substituted by Rba and/or Rbb, and is phenyl, in which
Rba is chlorine, fluorine, bromine, trifluoromethyl, methyl, ethyl, methoxy or ethoxy,
Rba is chlorine, fluorine, bromine, trifluoromethyl, methyl, ethyl, methoxy or ethoxy.

A further subvariant (variant a171) of the compounds according to variant a of this invention includes those compounds of formula I,
Rb is substituted by Rba and/or Rbb, and is phenyl, in which
Rba is chlorine, fluorine, bromine, trifluoromethyl, methyl, ethyl, methoxy or ethoxy,
Rba, is chlorine, fluorine, trifluoromethyl, methyl or methoxy.

A further subvariant (variant a172) of the compounds according to variant a of this invention includes those compounds of formula I,
Rb is substituted by Rba and/or Rbb, and is phenyl, in which
Rba is chlorine, methyl, methoxy or ethoxy,
Rbb is chlorine, methyl or methoxy.

A further subvariant (variant a173) of the compounds according to variant a of this invention includes those compounds of formula I,
Rb is substituted by Rba and/or Rbb, and is phenyl, in which
Rba is chlorine, methyl or methoxy,
Rba is methoxy.

Another subvariant (variant a18) of the compounds according to variant a of this invention includes those compounds of formula I,
Rb is substituted by Rba and/or Rbb, and is phenyl, in which
Rba is attached in the meta position with respect to the binding position in which said phenyl ring is bonded to the adjacent carbonyl group, and is chlorine, fluorine, bromine, trifluoromethyl, methyl, ethyl, methoxy or ethoxy,
Rba is attached in the meta or para position with respect to the binding position in which said phenyl ring is bonded to the adjacent carbonyl group, and is chlorine, fluorine, bromine, trifluoromethyl, methyl, ethyl, methoxy or ethoxy.

A further subvariant (variant a181) of the compounds according to variant a of this invention includes those compounds of formula I,
Rb is substituted by Rba and/or Rbb, and is phenyl, in which
Rba is attached in the meta position with respect to the binding position in which said phenyl ring is bonded to the adjacent carbonyl group, and is chlorine, methyl or methoxy,
Rba is attached in the meta or para position with respect to the binding position in which said phenyl ring is bonded to the adjacent carbonyl group, and is chlorine, methyl or methoxy.

A more precise subvariant (variant a19) of the compounds according to variant a of this invention includes those compounds of formula I, in which
Rb is 3-chloro-phenyl, 4-chloro-phenyl, 3-fluoro-phenyl, 3-bromo-phenyl, 2-methyl-phenyl, 3-methyl-phenyl, 4-methyl-phenyl, 3,5-di-trifluoromethyl-phenyl, 4.methoxy-phenyl, 3-methoxy-phenyl, 3,5-dimethoxy-phenyl, 3,4-dimethoxy-phenyl, 3-phenoxy-phenyl, or 4-acetyl-phenyl.

A further more precise subvariant (variant a191) of the compounds according to variant a of this invention includes those compounds of formula I, in which
Rb is 3-chloro-phenyl, 4-methyl-phenyl, 3-methoxy-phenyl, 3,5-dimethoxy-phenyl, 3,4-dimethoxy-phenyl, or 3-phenoxy-phenyl.

Another further more precise subvariant (variant a192) of the compounds according to variant a of this invention includes those compounds of formula I, in which
Rb is 3-chloro-phenyl, 4-chloro-phenyl, 2-methyl-phenyl, 3-methyl-phenyl, 4-methyl-phenyl, 3-methoxy-phenyl, 4-methox-phenyl or 3,5-dimethoxy-phenyl.

A yet further more precise subvariant (variant a193) of the compounds according to variant a of this invention includes those compounds of formula I, in which
Rb is 3-methoxy-phenyl, or 3,5-dimethoxy-phenyl.

Another subvariant (variant a20) of the compounds according to variant a of this invention includes those compounds of formula I, in which
Rb is substituted by Rba and/or Rbb, and is phenyl, in which
Rba is attached in the meta position with respect to the binding position in which said phenyl ring is bonded to the adjacent carbonyl group, and is 1-2C-alkoxy,
Rbb is attached in the meta or para position with respect to the binding position in which said phenyl ring is bonded to the adjacent carbonyl group, and is 1-2C-alkoxy, such as e.g. 3-methoxy-phenyl, 3,5-dimethoxy-phenyl, or 3,4-dimethoxy-phenyl.

Another subvariant (variant a3) of the compounds according to variant a of this invention includes those compounds of formula I,
Rb is optionally substituted by Rba and/or Rbb and/or Rbc, and is naphthyl, in which
Rba, Rbb and Rbc have independently one of the meanings as defined in aspect 1 above, or, in an independent embodimental alternative, Rba, Rbb and Rbc have independently one of the meanings as defined in restriction e (according to restriction group a) or in restriction h (according to restriction group b) above.

Another subvariant (variant a4) of the compounds according to variant a of this invention includes those compounds of formula I, in which
Rb is unsubstituted phenyl.

Another subvariant (variant a5) of the compounds according to variant a of this invention includes those compounds of formula I,
Rb is unsubstituted naphthyl.

A special concern within the meaning of the present invention refers to those compounds of formula I according to this invention which are included by one or, when possible, by more of the following embodiments:

A special embodiment (embodiment 1) of the compounds of formula I according to this invention includes those compounds of formula I, in which
Ra is —C(O)R1.

Compounds of embodiment 1 may include those compounds of formula I, in which
Ra is —C(O)R1, in which
R1 is 1-7C-alkyl, such as e.g. methyl, propyl, or hexyl.

Yet compounds of embodiment 1 may include those compounds of formula I, in which
Ra is —C(O)R1, in which
R1 is 1-4C-alkyl, such as e.g. methyl or propyl.

Yet compounds of embodiment 1 may include those compounds of formula I, in which
Ra is —C(O)R1, in which
R1 is 2-4C-alkyl, such as e.g. ethyl or propyl.

A subembodiment (embodiment 1a) of the compounds of embodiment 1 according to this invention includes those compounds of formula I, in which
Ra is —C(O)R1, in which
R1 is methyl, ethyl or propyl.

Another subembodiment (embodiment 1 b) of the compounds of embodiment 1 according to this invention includes those compounds of formula I, in which
Ra is —C(O)R1, in which
R1 is methyl which is mono-substituted by R5, ethyl which is mono-substituted by R5, or propyl which is mono-substituted by R5, in which
R5 is methoxy, ethoxy, 2-methoxyethoxy, hydroxyl, pyridyl, pyrimidinyl, pyrazinyl, imidazolo or pyrazolo.

Compounds of embodiment 1b more worthy to be mentioned may include those compounds of formula I, in which
Ra is —C(O)R1, in which
R1 is (R5)-methyl, or 2-(R5)-ethyl, in which R5 is methoxy, ethoxy, 2-methoxyethoxy, hydroxyl, pyridyl or imidazolo.

Compounds of embodiment 1b in particular worthy to be mentioned may include those compounds of formula I, in which
Ra is —C(O)R1, in which
R1 is methoxy-methyl, 2-methoxy-ethyl, (2-methoxyethoxy)-methyl, 2-(2-methoxyethoxy)-ethyl, hydroxymethyl, 2-hydroxy-ethyl, (pyridin-2-yl)-methyl, (pyridin-3-yl)-methyl, (pyridin4-yl)-methyl, 2-(pyridin-2-yl)-ethyl, 2-(pyridin-3-yl)-ethyl or 2-(pyridin4-yl)-ethyl.

Another subembodiment (embodiment 1c) of the compounds of embodiment 1 according to this invention includes those compounds of formula I, in which
Ra is —C(O)R1, in which
R1 is 2,3-dihydroxypropyl.

Another special embodiment (embodiment 2) of the compounds of formula I according to this invention includes those compounds of formula I, in which
Ra is —C(O)OR2.

Compounds of embodiment 2 may include those compounds of formula I, in which
Ra is —C(O)OR2, in which
R2 is 1-7C-alkyl, such as e.g. methyl, ethyl, tertbutyl, or pentyl, particularly ethyl.

A subembodiment (embodiment 2a) of the compounds of embodiment 2 according to this invention includes those compounds of formula I, in which
Ra is —C(O)OR2, in which
R2 is methyl, ethyl or propyl.

Compounds of embodiment 2a more worthy to be mentioned may include those compounds of formula I, in which
Ra is —C(O)OR2, in which
R2 is ethyl.

Another subembodiment (embodiment 2b) of the compounds of embodiment 2 according to this invention includes those compounds of formula I, in which
Ra is —C(O)OR2, in which
either
R2 is methyl which is mono-substituted by R5, ethyl which is mono-substituted by R5, or propyl which is mono-substituted by R5, in which
R5 is pyridyl, pyrimidinyl or pyrazinyl.
or
R2 is ethyl which is mono-substituted by R5, or propyl which is mono-substituted by R5, in which
R5 is methoxy, ethoxy, 2-methoxyethoxy, hydroxyl, imidazolo or pyrazolo.

Compounds of embodiment 2b more worthy to be mentioned may include those compounds of formula I, in which
Ra is —C(O)OR2, in which
either
R2 is (R5)-methyl, or 2-(R5)-ethyl, in which
R5 is pyridyl,
or
R2 is 2-(R5)-ethyl, in which
R5 is methoxy, ethoxy, 2-methoxyethoxy, hydroxyl or imidazolo.

Compounds of embodiment 2b in particular worthy to be mentioned may include those compounds of formula I, in which
Ra is —C(O)OR2, in which
R2 is 2-methoxy-ethyl, 2-(2-methoxyethoxy)-ethyl, 2-hydroxy-ethyl, (pyridin-2-yl)-methyl, (pyridin-3-yl)-methyl, (pyridin4-yl)-methyl, 2-(pyridin-2-yl)-ethyl, 2-(pyridin-3-yl)-ethyl or 2-(pyridin-4-yl)-ethyl.

Another subembodiment (embodiment 2c) of the compounds of embodiment 2 according to this invention includes those compounds of formula I, in which
Ra is —C(O)OR2, in which
R2 is 2,3-dihydroxypropyl.

Another special embodiment (embodiment 3) of the compounds of formula I according to this invention includes those compounds of formula I, in which
Ra is —C(O)SR2.

Compounds of embodiment 3 may include those compounds of formula I, in which
Ra is —C(O)SR2, in which
R1 is 1-7C-alkyl, such as e.g. ethyl.

A subembodiment (embodiment 3a) of the compounds of embodiment 3 according to this invention includes those compounds of formula I, in which
Ra is —C(O)SR2, in which
R2 is methyl, ethyl or propyl.

Compounds of embodiment 3a more worthy to be mentioned may include those compounds of formula I, in which
Ra is —C(O)SR2, in which
R2 is ethyl.

Another subembodiment (embodiment 3b) of the compounds of embodiment 3 according to this invention includes those compounds of formula I, in which
Ra is —C(O)SR2, in which
either
R2 is methyl which is mono-substituted by R5, ethyl which is mono-substituted by R5, or propyl which is mono-substituted by R5, in which
R5 is pyridyl, pyrimidinyl or pyrazinyl.
or
R2 is ethyl which is mono-substituted by R5, or propyl which is mono-substituted by R5, in which
R5 is methoxy, ethoxy, 2-methoxyethoxy, hydroxyl, imidazolo or pyrazolo.

Compounds of embodiment 3b more worthy to be mentioned may include those compounds of formula I, in which
Ra is —C(O)SR2, in which
either
R2 is (R5)-methyl, or 2-(R5)-ethyl, in which
R5 is pyridyl,
or
R2 is 2-(R5)-ethyl, in which
R5 is methoxy, ethoxy, 2-methoxyethoxy, hydroxyl or imidazolo.

Compounds of embodiment 3b in particular worthy to be mentioned may include those compounds of formula I, in which
Ra is —C(O)SR2, in which
R2 is 2-methoxy-ethyl, 2-(2-methoxyethoxy)-ethyl, 2-hydroxy-ethyl, (pyridin-2-yl)-methyl, (pyridin-3-yl)-methyl, (pyridin4-yl)-methyl, 2-(pyridin-2-yl)-ethyl, 2-(pyridin-3-yl)-ethyl or 2-(pyridin-4-yl)-ethyl.

Another special embodiment (embodiment 4) of the compounds of formula I according to this invention includes those compounds of formula I, in which
Ra is —C(O)N(R3)R4.

Another special embodiment (embodiment 5) of the compounds of formula I according to this invention includes those compounds of formula I, in which
Ra is —S(O)$_2$R1.

Another special embodiment (embodiment 6) of the compounds of formula I according to this invention includes those compounds of formula I, in which
Ra is —S(O)$_2$N(R3)R4.

Among these aforementioned embodiments, the embodiments 1 and 2 and 3 are to be emphasized.

Another special embodiment (embodiment 7) of the compounds of formula I according to this invention includes those compounds of formula I, in which
Rb is optionally substituted by Rba and/or Rbb and/or Rbc, and is aryl, in which
aryl is naphthyl, or phenyl.

Particular compounds of embodiment 7 may include those compounds of formula I, in which
Rb is optionally substituted by Rba and/or Rbb and/or Rbc, and is phenyl.

Another special embodiment (embodiment 8) of the compounds of formula I according to this invention includes those compounds of formula I, in which
Rb is mono- or bi-substituted by Rba and/or Rbb, and is phenyl.

Particular compounds of embodiment 8 may include those compounds of formula I, in which
Rb is 3-chloro-phenyl, 3-methoxy-phenyl, 3,5-dimethoxy-phenyl, 3,4-dimethoxy-phenyl, or 3-phenoxy-phenyl.
Yet particular compounds of embodiment 8 may include those compounds of formula I, in which Rb is substituted by Rba and/or Rbb, and is phenyl, in which
Rba is chlorine, methyl or methoxy,
Rbb is chlorine, methyl or methoxy.
Further particular compounds of embodiment 8 may include those compounds of formula I, in which
Rbb is any one selected from 3-chloro-phenyl, 4-chloro-phenyl, 2-methyl-phenyl, 3-methyl-phenyl, 4-methyl-phenyl, 3-methoxy-phenyl, 4-methoxy-phenyl and 3,5-dimethoxy-phenyl.
More particular compounds of embodiment 8 may include those compounds of formula I, in which
Rb is 3-methoxy-phenyl, or 3,5-dimethoxy-phenyl.
Another special embodiment (embodiment 9) of the compounds of formula I according to this invention includes those compounds of formula I, in which
Rb is unsubstituted phenyl.
Another special embodiment (embodiment 10) of the compounds of formula I according to this invention includes those compounds of formula I, in which
Rb is unsubstituted naphthyl.
Particular compounds of embodiment 10 may include those compounds of formula I, in which
Rb is naphthalen-1-yl, or naphthalen-2-yl.
Another special embodiment (embodiment 11) of the compounds of formula I according to this invention includes those compounds of formula I, in which
Rb is substituted by Rba and/or Rbb, and is phenyl, in which
Rba is attached in the meta position with respect to the binding position in which said phenyl ring is bonded to the adjacent carbonyl group, and is halogen, trifluoromethyl, 1-4C-alkyl, or 1-4C-alkoxy,
Rbb is attached in the meta or para position with respect to the binding position in which said phenyl ring is bonded to the adjacent carbonyl group, and is halogen, trifluoromethyl, 1-4C-alkyl, 1-4C-alkoxy, phenoxy, hydroxyl, or 1-4C-alkylcarbonyl,
such as e.g. 3-chloro-phenyl, 3-fluoro-phenyl, 3-bromo-phenyl, 4-methyl-phenyl, 3,5-di-trifluoromethyl-phenyl 4-methoxy-phenyl, 3-methoxy-phenyl, 3,5-dimethoxy-phenyl, 3,4-dimethoxy-phenyl, 3-phenoxy-phenyl, or 4-acetyl-phenyl.
Among these aforementioned embodiments, the embodiments 8, 9 and 10 are to be emphasized, and the particular compounds of embodiment 8 are to be more emphasized.
A further special embodiment (embodiment 12) of the compounds of formula I according to this invention includes those compounds of formula I, in which
Ra is —C(O)R1, in which
R1 is not methyl.
A further special embodiment (embodiment 13) of the compounds of formula I according to this invention includes those compounds of formula I, in which
Ra is —C(O)R1, in which
R1 is not unsubstituted 1-4C-alkyl.
A further special embodiment (embodiment 14) of the compounds of formula I according to this invention includes those compounds of formula I, in which
Ra is —C(O)R1, in which
R1 is 1-4C-alkyl substituted by R5.

A group of compounds according to special embodiment 1 of the compounds of formula I according to this invention may include those compounds of formula I, in which
Ra is —C(O)R1,
in which R1 is a radical selected from the following List 1.
List 1 consists of the following radicals:

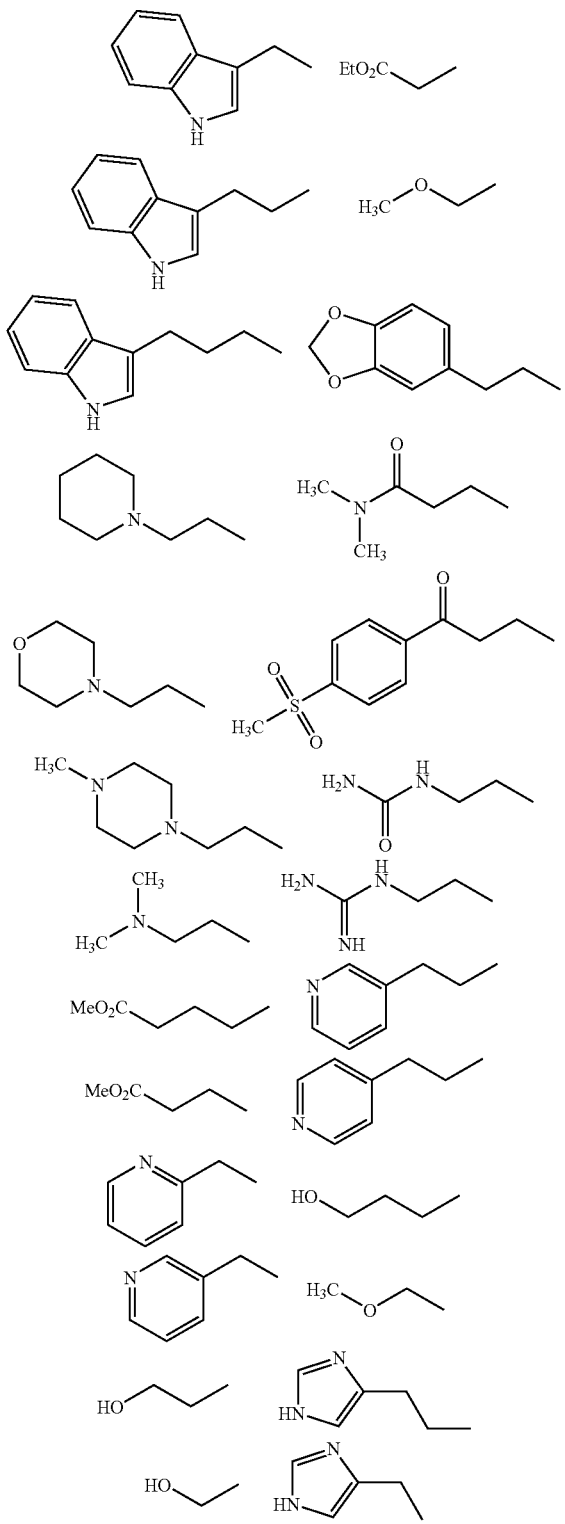

Another group of compounds of formula I according to this invention includes those compounds of formula I, in which
Ra is —C(O)R1, in which
R1 is a radical selected from the List 1,
Rb is 3-chloro-phenyl, 3-fluoro-phenyl, 3-bromo-phenyl, 4-methyl-phenyl, 3,5-di-trifluoromethyl-phenyl, 4-methoxy-phenyl, 3-methoxy-phenyl, 3,5-dimethoxy-phenyl, 3,4dimethoxy-phenyl, 3-phenoxy-phenyl, or 4-acetyl-phenyl.

Another group of compounds of formula I according to this invention includes those compounds of formula 1, in which
Ra is —C(O)R1, in which
R1 is a radical selected from the List 1, and
Rb is 3-methoxy-phenyl or 3,5-dimethoxy-phenyl.

A group of compounds according to special embodiment 2 of the compounds of formula I according to this invention may include those compounds of formula I, in which
Ra is —C(O)OR2, in which R2 is a radical selected from the following List 2.
List 2 consists of the following radicals:

Another group of compounds of formula I according to this invention includes those compounds of formula I, in which
Ra is —C(O)OR2, in which
R2 is a radical selected from the List 2,
Rb is 3-chloro-phenyl, 3-fluoro-phenyl, 3-bromo-phenyl, 4-methyl-phenyl, 3,5-di-trifluoromethyl-phenyl, 4-methoxy-phenyl, 3-methoxy-phenyl, 3,5-dimethoxy-phenyl, 3,4-dimethoxy-phenyl, 3-phenoxy-phenyl, or 4-acetyl-phenyl.

Another group of compounds of formula I according to this invention includes those compounds of formula I, in which
Ra is —C(O)OR2, in which
R2 is a radical selected from the List 2, and
Rb is 3-methoxy-phenyl or 3,5-dimethoxy-phenyl.

A group of compounds of formula I according to special embodiment 3 of the compounds according to this invention may include those compounds of formula I, in which
Ra is —C(O)SR2, in which R2 is a radical selected from the following List 3.
List 3 consists of the following radicals:

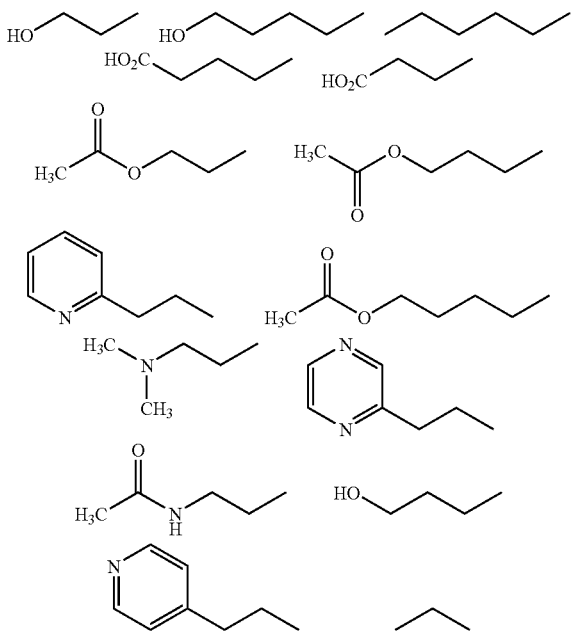

Another group of compounds of formula I according to this invention includes those compounds of formula I, in which
Ra is —C(O)SR2, in which
R2 is a radical selected from the List 3,
Rb is 3-chloro-phenyl, 3-fluoro-phenyl, 3-bromo-phenyl, 4-methyl-phenyl, 3,5-di-trifluoromethyl-phenyl, 4-methoxy-phenyl, 3-methoxy-phenyl, 3,5-dimethoxy-phenyl, 3,4-dimethoxy-phenyl, 3-phenoxy-phenyl, or 4-acetyl-phenyl.

Another group of compounds of formula I according to this invention includes those compounds of formula I, in which
Ra is —C(O)8R2, in which
R2 is a radical selected from the List 3, and
Rb is 3-methoxy-phenyl or 3,5-dimethoxy-phenyl.

Compounds of formula I according to the present invention can be prepared as described below or as shown in the following reaction schemes, or as disclosed in WO2004/024066 or, particularly, WO2004/024065, the disclosure of which is incorporated herein, or similarly or analogously thereto according to preparation procedures or synthesis strategies known to the person skilled in the art. Accordingly, compounds of formula I according to the present invention can be obtained as specified by way of example in the following examples, or similarly or analogously thereto.

Thus, as shown in reaction scheme below, a compound of formula III, in which Ra has the meanings given above, can be condensed with malonitrile in the presence of sulfur and a suitable base, such as for example an amine (e.g. diethyl amine or morpholine) to give corresponding compounds of formula II in a manner known to the person skilled in the art (e.g. according to a Gewald reaction) or as described in the following examples.

Compounds of formula III are known or can be obtained in an art-known manner.

Compounds of formula II can be reacted with compounds of formula Rb—C(O)—X, in which Rb has the meanings mentioned above and X is a suitable leaving group, preferably a chlorine atom, in an acylation reaction under conditions habitual per se to give the desired compounds of formula I, in which Ra and Rb have the meanings given above.

Alternatively, compounds of the formula I can also be prepared from the corresponding compounds of formula II and corresponding compounds of formula Rb—C(O)—X, in which X is hydroxyl, by reaction with amide bond linking reagents known to the person skilled in the art. Exemplary amide bond linking reagents known to the person skilled in the art which may be mentioned are, for example, the carbodiimides (e.g. dicyclohexylcarbodiimide or, preferably, 1-ethyl-3-(3-dimethylaminopropyl)carbodiimide hydrochloride), azodicarboxylic acid derivatives (e.g. diethyl azodicarboxylate), uronium salts [e.g. O-(benzotriazol-1-yl)-N,N,N',N'-tetramethyluronium tetrafluoroborate or O-(benzotriazol-1yl)-N,N,N',N'-tetramthyl-uronium-hexafluorophosphate] and N,N'-carbonyldiimidazole. In the scope of this invention preferred amide bond linking reagents are uronium salts and, particularly, carbodiimides, preferably, 1-ethyl-3-(3-dimethylaminopropyl)carbodiimide hydrochloride (EDC).

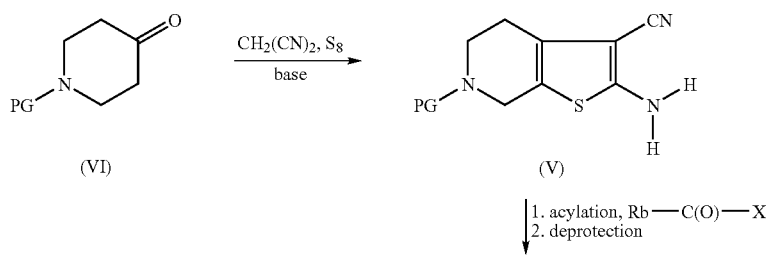

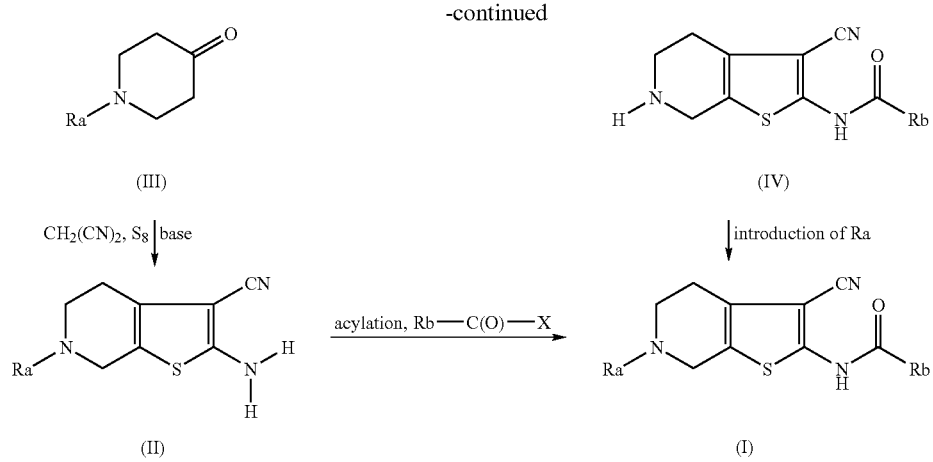

Acid derivatives of formula Rb—C(O)—X are known, commercially available or can be prepared as it is known for the skilled person, e.g. from the corresponding carboxylic acids.

In an alternative synthesis route, compounds of formula VI, in which PG is a suitable temporary protective group, such as for example tertbutoxycarbonyl (Boc) or one of those mentioned in "Protective Groups in Organic Synthesis" by T. Greene and P. Wuts (John Wiley & Sons, Inc. 1999, 3rd Ed.) or in "Protecting Groups (Theme Foundations Organic Chemistry Series N Group" by P. Kocienski (Theme Medical Publishers, 2000), can be condensed with malonitrile in the presence of sulfur and a suitable base as described above to give corresponding compounds of formula V.

Compounds of formula VI are known or can be obtained in an art-known manner.

Compounds of formula V can be acylated with compounds of formula Rb—C(O)—X analogously as mentioned above. Subsequental deprotection of the protective group PG in a manner customary per se for the skilled person gives compounds of formula IV, in which Rb has the meanings as mentioned above.

Compounds of formula IV can be converted into desired compounds of formula I by introduction of the group Ra via methods known to one of ordinary skill in the art.

More specifically, for example, compounds of the formula I, in which a) Ra is an acyl group, can be prepared from compounds of formula IV by acylation reaction;
b) Ra is a sulfonyl group, can be obtained from compounds of formula IV by sulfonylation reaction;
c) Ra is an ester group, can be obtained from compounds of formula IV by carbamate formation reaction;
d) Ra is an amide group, can be prepared from compounds of formula IV by urea formation reaction;
e) Ra is a thioester group, can be prepared from compounds of formula IV by thiocarbamate formation reaction;
f.) Ra is a sulfonamide group, can be prepared from compounds of formula IV by sulfamide formation reaction.

The methods mentioned under a) to f) are expediently carried out analogously to the methods known to the person skilled in the art or as described by way of example in the following examples.

The appropriate starting compounds used in the methods mentioned under a) to f) are art-known or can be obtained according to art-known procedures.

Thus, for example, when 3-(Har)-propionic acids in which Har has the meanings given above (e.g. pyridyl) are used as starting compounds in the method mentioned under a.), these compounds can be obtained via CC-coupling reactions, such as e.g. by Heck reaction or, starting from aldehydes of the formula Har-CHO, by Knoevenagel or Homer-Wadsworth-Emmons reaction, and hydration reaction.

It is to be understood for the skilled worker, that certain compounds of formula I according to this invention can be converted into further compounds of formula I by art-known synthesis strategies and reactions habitual per se to a person of ordinary skill in the art.

Therefore, optionally, compounds of formula ,can be converted into further compounds of formula I by methods known to one of ordinary skill in the art. More specifically, for example, from compounds of the formula I in which i) R5 is acyloxy, such as e.g. acetoxy, the corresponding free hydroxyl compounds can be obtained by removal of the acyl group, such as e.g. by saponification reaction;
ii) Het is a cyclic acetal or ketal, such as e.g. the 2,2-dimethyl-[1,3]dioxolan acetal, the corresponding free dihydroxy compounds can be obtained by cleavage of the acetal or ketal, such as e.g. by deacetalization reaction;
iii) R5 is an ester group, such as e.g. methoxycarbonyl, the corresponding free carboxyl compounds can be obtained by deesterification reaction, such as e.g. by saponification reaction.

The methods mentioned under i) to iii) can be expediently carried out analogously to the methods known to the person skilled in the art or as described by way of example in the following examples.

Optionally, compounds of the formula I can be converted into their salts, or, optionally, salts of the compounds of the formula I can be converted into the free compounds. Corresponding processes are habitual per se to the skilled person.

It is moreover known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in "Protective Groups in Organic Synthesis" by T. Greene and P. Wuts (John Wiley & Sons, Inc. 1999, 3rd Ed.) or in "Protecting Groups (Theme Foundations Organic Chemistry Series N Group" by P. Kocienski (Theme Medical Publishers, 2000).

The substances of formula I according to the invention are isolated and purified in a manner known per se, for example by distilling off the solvent under reduced pressure and recrystallizing the residue obtained from a suitable solvent or subjecting it to one of the customary purification methods, such as, for example, column chromatography on a suitable support material.

Salts are obtained by dissolving the free compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low-molecular-weight aliphatic alcohol, such as ethanol or isopropanol) which contains the desired acid or base, or to which the desired acid or base is then added. The salts are obtained by filtering, reprecipitating, precipitating with a nonsolvent for the addition salt or by evaporating the solvent. Salts obtained can be converted into the free compounds, which can in turn be converted into salts, by alkalization or by acidification. In this manner, pharmacologically unacceptable salts can be converted into pharmacologically acceptable salts.

Suitably, the conversions mentioned in this invention can be carried out analogously or similarly to methods which are familiar per se to the person skilled in the art.

The person skilled in the art knows on the basis of his/her knowledge and on the basis of those synthesis routes, which are shown and described within the description of this invention, how to find other possible synthesis routes for compounds of formula I. All these other possible synthesis routes are also part of this invention.

Having described the invention in detail, the scope of the present invention is not limited only to those described characteristics or embodiments. As will be apparent to persons skilled in the art, modifications, analogies, variations, derivations, homologisations and adaptations to the described invention can be made on the base of art-known knowledge and/or, particularly, on the base of the disclosure (e.g. the explicite, implidite or inherent disclosure) of the present invention without departing from the spirit and scope of this invention as defined by the scope of the appended claims.

The following examples serve to illustrate the invention further without restricting it. Likewise, further compounds of formula I, whose preparation is not explicitly described, can be prepared in an analogous or similar manner or in a manner familiar per se to the person skilled in the art using customary process techniques.

Any or all of the compounds of formula I according to the present invention which are mentioned in the following examples, particularly which are mentioned as final compounds, as well as their salts are a preferred subject of the present invention.

In the examples, MS stands for mass spectrum, calc. for calculated, fnd. for found, Boc for the tertbutoxycarbonyl group, EDC for 1-ethyl-3-(3-dimethylaminopropyl)carbodiimide hydrochloride and other abbreviations have their meanings customary per se to the skilled person.

EXAMPLES

Final Compounds:

1. N-(6-tert.-Butyloxycarbonyl-3-cyano-4,5,6,7-tetrahydro-thieno[2,3-c]pyridin-2-yl)-benzamide

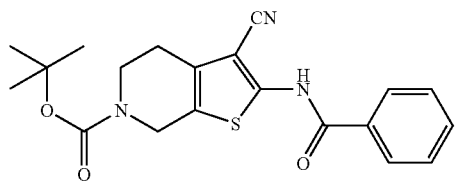

Prepared according to general procedure A starting from 2-amino-3-cyano-4,7-dihydro-thieno[2,3-c]pyridine-6(5H)-carboxylic acid 1,1-dimethylethyl ester (compound A2) and benzoyl chloride.

MS: calc.: $C_{20}H_{21}N_3O_3S$ (383.47) fnd.: 384.1 [M+H]

2. N-(6-tert.-Butyloxycarbonyl-3-cyano4,5,6,7-tetrahydro-thieno[2,3-c]pyridin-2-yl)-3,5-dimethoxy-benzamide

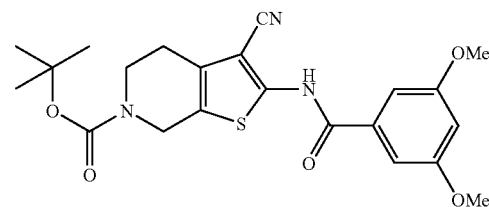

Prepared according to general procedure A starting from 2-amino-3-cyano-4,7-dihydro-thieno[2,3-c]pyridine-6(5H)-carboxylic acid 1,1-dimethylethyl ester (compound A2) and 3,5-dimethoxybenzoyl chloride.

MS: calc.: $C_{22}H_{25}N_3O_5S$ (443.53) fnd.: 344.1 [M+H-Boc], 466.0 [M+Na]

3. N-(6-tert.-Butyloxycarbonyl-3-cyano-4,5,6,7-tetrahvdro-thieno[2,3-c]pyridin-2-yl)-3-methoxybenzamide

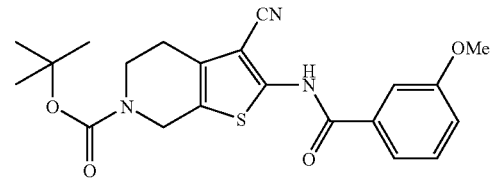

Prepared according to general procedure A starting from 2-amino-3-cyano-4,7-dihydro-thieno[2,3-c]pyridine-6(5H)-carboxylic acid 1,1-dimethylethyl ester (compound A2) and 3-methoxybenzoyl chloride.

MS: calc.: $C_{21}H_{23}N_3O_4S$ (413.50) fnd.: 413.9 [M+H]

4. N-(3-Cyano-7-ethylcarbonyl-4,5,6,7-tetrahydro-thieno[2,3-c]pyridin-2-yl)-3,5-dimethoxybenzamide

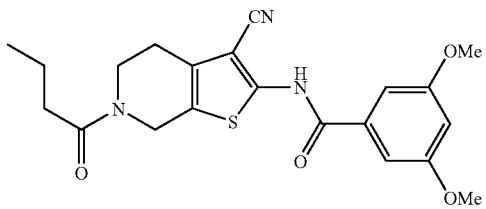

Prepared according to general procedure A starting from N-(3-cyano-4,5,6,7-tetrahydro-thieno[2,3-c]pyridin-2-yl)-3,5-dimethoxybenzamide (compound B1) and butyric acid chloride.

MS: calc.: $C_{21}H_{23}N_3O_4S$ (413.50) fnd.: 413.9 [M+H]

5. N-(3-Cyano-7-butyclcarbonyl-4,5,6,7-tetrahydro-thieno[2,3-c]pyridin-2-yl)-benzamide

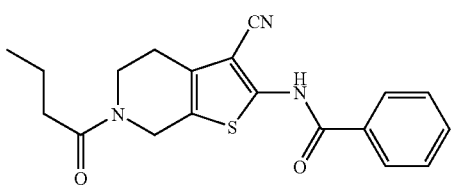

Prepared according to general procedure A starting from N-(3-cyano4,5,6,7-tetrahydro-hieno[2,3-c]pyridin-2-yl)-benzamide (compound B2) and propionic acid chloride.

MS: calc.: $C_{19}H_{19}N_3O_2S$ (353.45) fnd.: 354.0 [M+H]

6. N-(3-Cyano-7-heptylcarbonyl-4,5,6,7-tetrahydro-thien[2,3-c]pyridin-2-yl)-benzamide

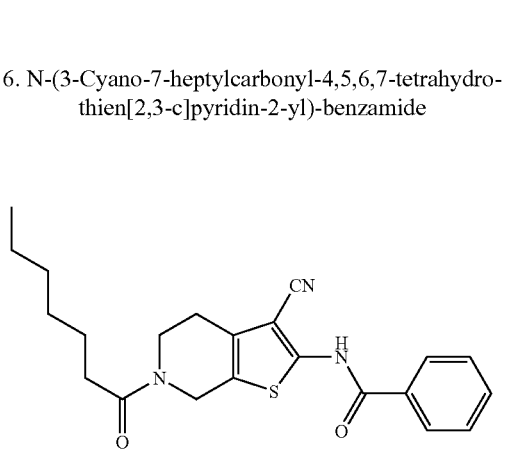

Prepared according to general procedure A starting from N-(3-cyano-4,5,6,7-tetrahydro-thieno[2,3-c]pyridin-2-yl)-benzamide (compound B2) and heptanoic acid chloride.

MS: calc.: $C_{22}H_{25}N_3O_2S$ (395.53) fnd.: 396.1 [M+H]

7. N-(3-Cyano-7-methoxyethylcarbonyl-4,5,6,7-tetrahydro-thien[2,3-c]pyridin-2-yl)-benzamide

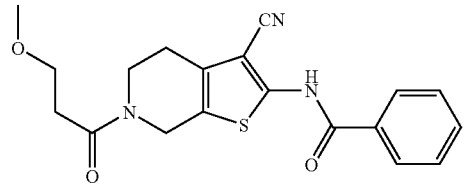

Prepared according to general procedure A starting from N-(3-cyano-4,5,6,7-tetrahydro-thieno[2,3-c]pyridin-2-yl)-benzamide (compound B2) and 3-methoxypropionic acid.

MS: calc.: $C_{19}H_{19}N_3O_3S$ (369.45) fnd.: 370.1 [M+H]

8. N-(3-Cyano-7-succinamic acid amidyl-4,5,6,7-tetrahydro-thieno[2,3-c]pyridin-2-yl)-benzamide

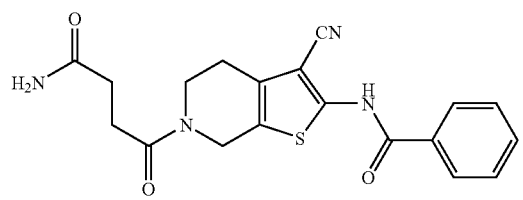

Prepared according to general procedure A starting from N-(3-cyano4,5,6,7-tetrahydro-thieno[2,3-c]pyridin-2-yl)-benzamide (compound B2) and succinamic acid.

MS: calc.: $C_{19}H_{18}N_4O_3S$ (382.44) fnd.: 382.9 [M+H]

9. N-(3-Cyano-7-(1-piperidine propionic acid amidyl)4,5,6,7-tetrahydro-thieno[2,3-c]pyridin-2-yl)-benzamide

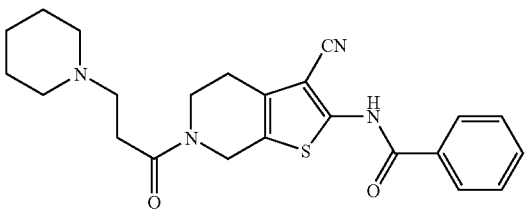

Prepared according to general procedure A starting from N-(3-cyano4,5,6,7-tetrahydro-thieno[2,3-c]pyridin-2-yl)-benzamide (compound B2) and 1-piperidinpropionic acid.

MS: calc.: $C_{23}H_{26}N_4O_2S$ (422.55) fnd.: 423.2 [M+H]

10. N-(3-Cyano-7-(3-ureido propionic acid amidyl)-4,5,6,7-tetrahydro-thieno[2,3-c]pyridin-2-yl)-benzamide

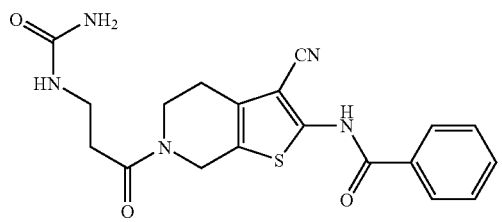

Prepared according to general procedure A starting from N-(3-cyano4,5,6,7-tetrahydro-thieno[2,3-c]pyridin-2-yl)-benzamide (compound B2) and 3-ureido propionic acid.

MS: calc.: $C_{19}H_{19}N_5O_3S$ (397.46) fnd.: 398.0 [M+H]

11. N-(3-Cyano-7-(3-indole propionic acid amidyl)-4,5,6,7-tetrahydro-thien[2,3-c]pryridin-2-yl)-benzamide

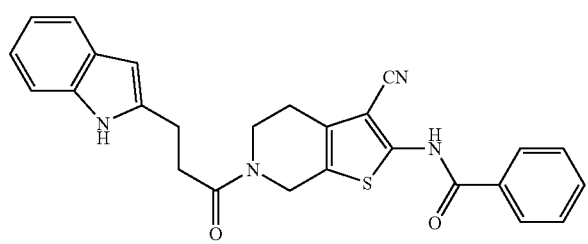

Prepared according to general procedure A starting from N-(3-cyano4,5,6,7-tetrahydro-thieno[2,3-c]pyridin-2-yl)-benzamide (compound B2) and 3-indole propionic acid.

MS: calc.: $C_{26}H_{22}N_4O_2S$ (454.55) fnd.: 455.1 [M+H]

12. N-(6-Ethoxycarbonyl-3-cyano-4,5,6,7-tetrahydro-thieno[2,3-c]pyridin-2-yl)-3-methoxybenzamide

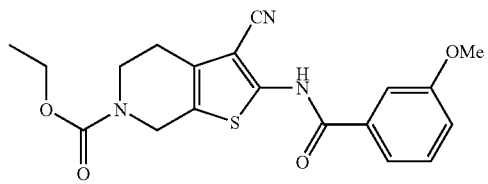

Prepared according to general procedure A starting from 2-amino-3-cyano4,7-dihydro-thieno[2,3-c]pyridine-6(5H)-carboxylic acid ethyl ester (compound A1) and 3-methoxybenzoyl chloride.

MS: calc.: $C_{19}H_{19}N_3O_4S$ (385.44) fnd.: 385.9 [M+H]

13. N-(6-Methoxyethoxycarbonyl-3-cyano-4,5,6,7-tetrahydro-thieno[2,3-c]pyridin-2-yl)-3-methoxybenzamide

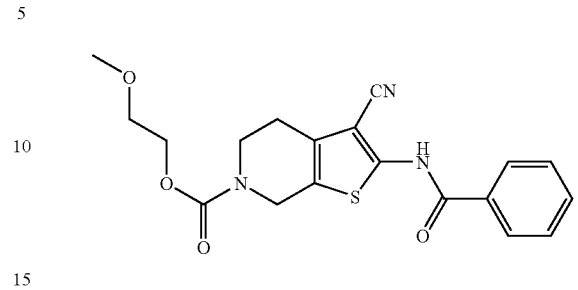

Prepared according to general procedure E starting from N-(3-cyano-4,5,6,7-tetrahydro-thieno[2,3-c]pyridin-2-yl)-benzamide (compound B2) and 2-methoxyethanol.

MS: calc.: $C_{19}H_{19}N_3O_4S$ (385.44) fnd.: 386.1 [M+H]

14. N-7-Pentyloxycarbonyl3-cyano-4,5,6,7-tetrahydro-thieno[2,3-c]pyridin-2-yl)-3-methoxybenzamide

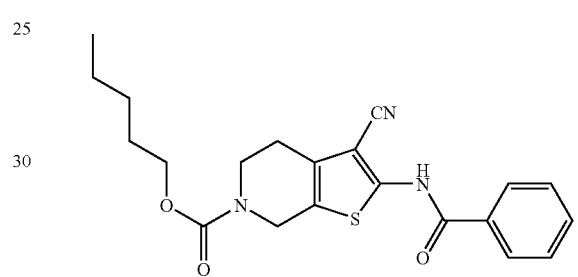

Prepared according to general procedure E starting from N-(3-cyano4,5,6,7-tetrahydro-thieno[2,3-c]pyridin-2-yl)-benzamide (compound B2) and 1-pentanol.

MS: calc.: $C_{21}H_{23}N_3O_3S$ (397.50) fnd.: 398.0 [M+H]

15. N-7-(4-Methoxyphenylbutanoxycarbonyl)-3-cyano-4,5,6,7-tetrahydro-thieno[2,3-c]pyridin-2-yl)-3-methoxybenzamide

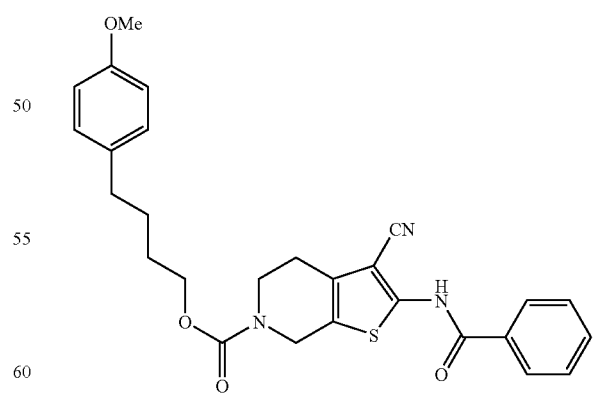

Prepared according to general procedure E starting from N-(3-cyano4,5,6,7-tetrahydro-thieno[2,3-c]pyridin-2-yl)-benzamide (compound B2) and 4-(4-methoxyphenyl)-butanole MS: calc.: $C_{27}H_{27}N_3O_4S$ (489.60) fnd.: 490.1 [M+H]

16. N-7-(3-Benzyloxy-1-propoxycarbonyl)-3-cyano4,5,6,7-tetrahydro-thieno[2,3-c]pyridin-2-yl)-3-methoxybenzamide

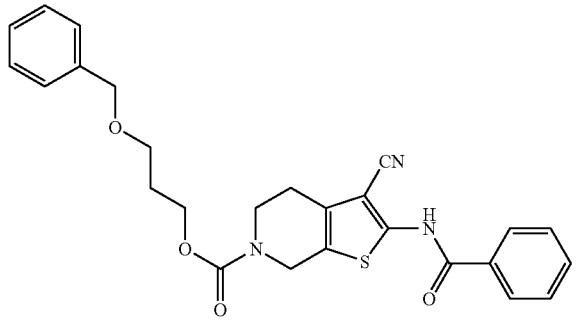

Prepared according to general procedure E starting from N-(3-cyano-4,5,6,7-tetrahydro-thieno[2,3-c]pyridin-2-yl)-benzamide (compound B2) and 3-benzyloxy-1-propanol.

MS: calc.: $C_{26}H_{25}N_3O_4S$ (475.57) fnd.: 476.1 [M+H]

17. N-7-(4-Methyl-5-thiazolylethoxycarbonyl)-3-cyano-4,5.6,7-tetrahydro-thieno[2,3-c]pyridin-2-yl)-3-methoxybenzamide

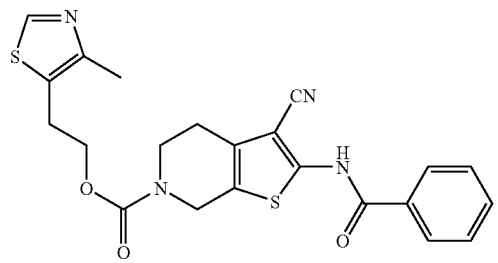

Prepared according to general procedure E starting from N-(3-cyano-4,5,6,7-tetrahydro-thieno[2,3-c]pyridin-2-yl)-benzamide (compound B2) and 4-methyl-5-thiazole-ethanol.

MS: calc.: $C_{22}H_{20}N_4O_3S_2$ (452.56) fnd.: 453.2 [M+H]

18. N-(6-Ethoxycarbonyl-3-cyano-4,5,6,7-tetrahydro-thieno[2,3-c]pyridin-2-yl)-benzamide

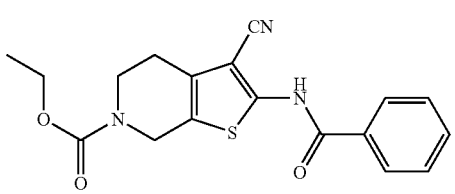

Prepared according to general procedure A starting from 2-amino-3-cyano-4,7-dihydro-thieno[2,3-c]pyridine-6(5H)-carboxylic acid ethyl ester (compound A1) and benzoyl chloride.

MS: calc.: $C_{18}H_{17}N_3O_3S$ (355.42) fnd.: 356.1 [M+H]

19. N-(6-Ethoxycarbonyl-3-cyano-4,5,6,7-tetrahydro-thieno[2,3-c]pyridin-2-yl)-3,5-dimethoxybenzamide

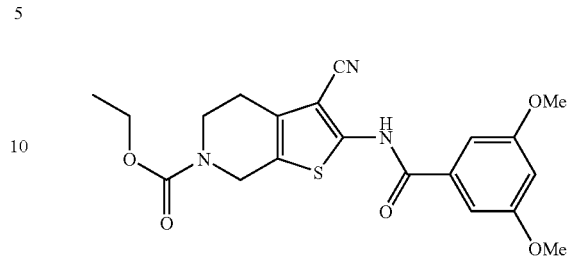

Prepared according to general procedure A starting from 2-amino-3-cyano-4,7-dihydro-thieno[2,3-c]pyridine-6(5H)-carboxylic acid ethyl ester (compound A1) and 3,5-dimethoxy benzoyl chloride.

MS: calc.: $C_{20}H_{21}N_3O_5S$ (415.47) fnd.: 356.1 [M+H]

20. N-(6-Acetyl-3-cyano-4,5,6,7-tetrahydro-thieno[2,3-c]pyridin-2-yl)-benzamide

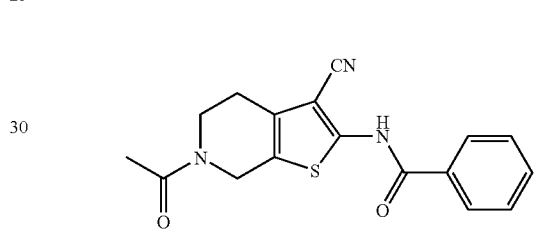

Prepared according to general procedure A starting from 6-acetyl-2-amino-3-cyano-4,5,6,7-tetrahydro-thieno[2,3-c]pyridine (compound A3) and benzoyl chloride.

MS: calc.: $C_{17}H_{15}N_3O_2S$ (325.39) fnd.: 326.0 [M+H]

21. 3-Cyano-2-[(1-phenyl-methanoyl)-amino]-4,7-dihydro-5H-thieno[2,3-c]pyridine-6-carboxylic acid 2-benzyloxy-ethyl ester

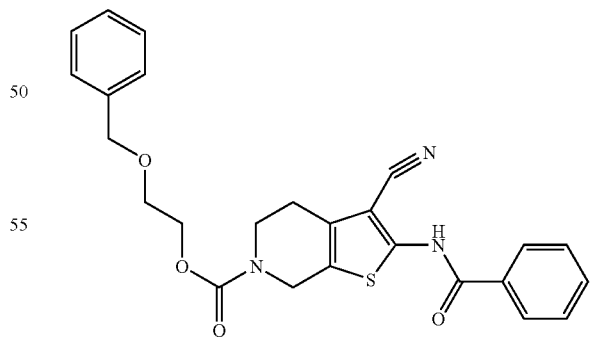

Prepared according to general procedure E starting from N-(3-cyano4,5,6,7-tetrahydro-thieno[2,3-c]pyridin-2-yl)-benzamide (compound B2) and 2-benzyloxyethanol.

MS: calc.: $C_{25}H_{23}N_3O_4S$ (461.54) fnd.: 462.1 [M+H]

The following compounds can be prepared according to general procedure A starting from N-(3-cyano-4,5,6,7-tetrahydro-thieno[2,3-c]pyridin-2-yl)-benzamide (compound B2) and the appropriate art-known carboxylic acid derivatives.

22. 4-{3-Cyano-2-[(1-phenyl-methanoyl)-amino]-4,7-dihydro-5H-thieno[2,3-c]pyridin-6-yl}-4-oxo-butyric acid methyl ester

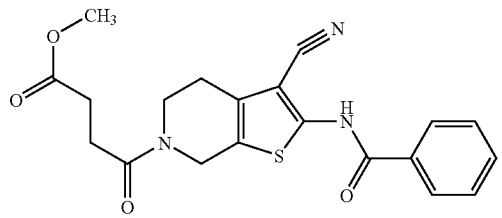

MS: calc.: $C_{20}H_{19}N_3O_4S$ (397.46) fnd.: 398 [M+H]

23. N-{3-Cyano-6-[3-(1,3-dioxo-1,3-dihydro-isoindol-2-yl)-propanoyl]-4,5,6,7-tetrahydro-thieno[2,3-c]pyridin-2-yl}-benzamide

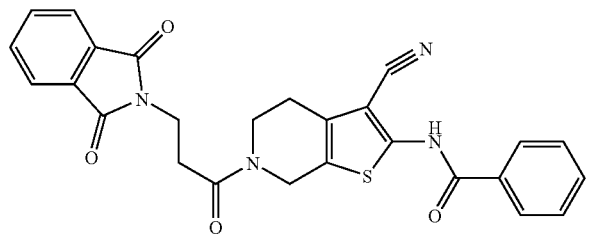

MS: calc.: $C_{26}H_{20}N_4O_4S$ (484.54) fnd.: 485.1 [M+H]

24. N-(6-Acetyl-3-cyano-4,5,6,7-tetrahydro-thieno[2,3-c]pyridin-2-yl)-3-methoxy-benzamide

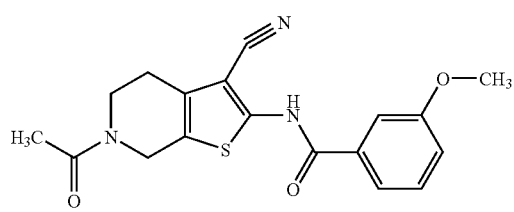

Prepared according to general procedure A starting from 6-acetyl-2-amino-3-cyano4,5,6,7-tetrahydro-thieno[2,3-c]pyridine (compound A3) and 3-methoxybenzoyl chloride.

MS: calc.: $C_{18}H_{17}N_3O_3S$ (355.42) fnd.: 356 [M+H]

25. N-(6-Butyryl-3-cyano-4,5,6,7-tetrahydro-thieno[2,3-c]pyridin-2-yl)-3-methoxy-benzamide

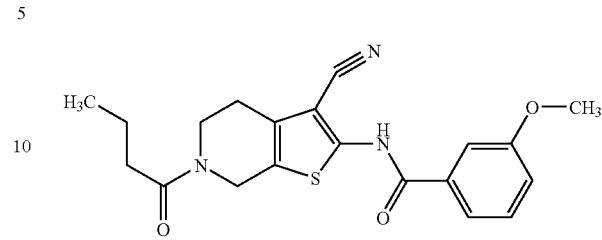

Prepared according to general procedure A starting from N-(3-cyano-4,5,6,7-tetrahydro-thieno[2,3-c]pyridin-2-yl)-3-methoxybenzamide (compound B3) and butyryl chloride.

MS: calc.: $C_{20}H_{21}N_3O_3S$ (383.47) fnd.: 384.1 [M+H]

26. N-(6-Acetyl-3-cyano-4,5,6,7-tetrahydro-thieno[2,3-c]pyridin-2-yl)-3,5-dimethoxy-benzamide

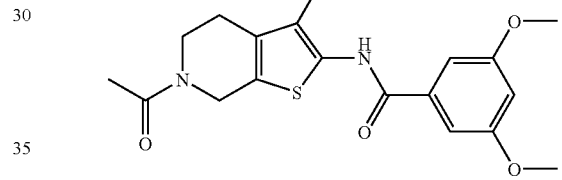

Prepared according to general procedure A starting from 6-Acetyl-2-amino-3-cyano-4,5,6,7-tetrahydro-thieno[2,3-c]pyridine (compound A3) and 3,5-dimethoxybenzoyl chloride.

MS: calc.: $C_{19}H_{19}N_3O_4S$ (385.44) fnd.: 386 [M+H]

The following compounds can be prepared according to general procedure A starting from N-(3-cyano-4,5,6,7-tetrahydro-thieno[2,3-c]pyridin-2-yl)-benzamide (compound B2) and the appropriate art-known carboxylic acid derivatives.

27. N-[3-Cyano-6-(4-oxo-pentanoyl)-4,5,6,7-tetrahydro-thieno[2,3-c]pyridin-2-yl]-benzamide

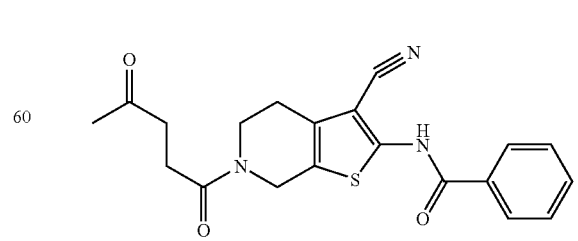

MS: calc.: $C_{20}H_{19}N_3O_3S$ (381.46) fnd.: 382.1 [M+H]

28. N-[3-Cyano6-(4-thiophen-2-yl-butanoyl)-4,5,6,7-tetrahydro-thieno[2,3-c]pryridin-2-yl]-benzamide

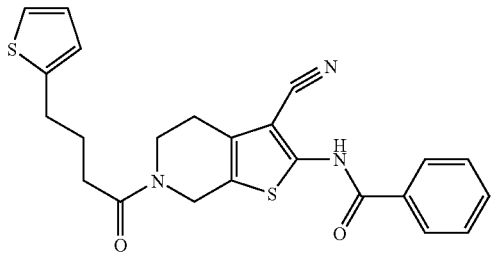

MS: calc.: $C_{23}H_{21}N_3O_2S_2$ (435.57) fnd.: 436.1 [M+H]

29. N-(3-Cyano-7-(ethylthiocarbonyl)-4,5,6,7-tetrahvdro-thieno[2,3-c]pyridin-2-yl)-benzamide

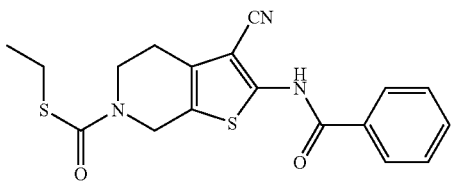

100 mg of N-(3-cyano4,5,6,7-tetrahydro-thieno[2,3-c]pyridin-2-yl)-benzamide (compound B2) and 57 mg of ethylchlorothioformiate are dissolved in 2 ml of pyridine. After stirring for 3 hours at room temperature, the solvent is removed and the remaining residue recristallized from ethanol to obtain the desired product.

MS: calc.: $C_{18}H_{17}N_{3O2}S_2$ (371.48) fnd.: 372.1 [M+H]

A. General Procedure for Amide Bond Formation a) 100 mmol of an amine and 120 mmol of an appropriate add chloride (which can be obtained in an art-known manner from the corresponding free acid, such as e.g. with the aid of oxalyl chloride) are dissolved either in a minimal amount of pyridine or toluene. In case of toluene as solvent, 125 mmol of a base (e.g. triethylamine) is added. The reaction mixture is stirred for some time at room temperature and, if necessary, is heated for some time either by conventional or microwave assisted heating. Then the solvent is either removed in vacuo or the reaction mixture partitioned between water and an appropriate solvent (e.g. ethyl acetate). In the second case, the aqueous layer is extracted several times with the organic solvent, the combined organic layers are dried (e.g. $MgSO_4$) and concentrated in vacuo. Purification of the crude product is achieved by flash chromatography and/or recristalizaton from an appropriate solvent (e.g. ethanol).

In some cases, the amide bond formation reaction is carried out using one of the following methods:

b) 20 mmol of a carboxylic acid and 20 mmol of EDC are dissolved or suspended in an appropriate solvent (e.g. dichloromethane) and 10 mmol of the amine and 0.1 mmol N,N-dimethylaminopyridine (DMAP) are added. After stirring for several hours at room temperature (If necessary, the reaction mixture is heated either by conventional heating or microwave assisted heating.), the reaction mixture is parttoned between water and an appropriate solvent (e.g. ethyl acetate or dichloromethane) and the aqueous layer is extracted several times with the same organic solvent. The combined organic layers are dried (e.g. $MgSO_4$) and concentrated in vacuo. Purification of the crude product is achieved by flash chromatography and/or recristalization from an appropriate solvent (e.g. ethanol).

A1 Alternative General Procedure for the Formation of Amide Bonds a) Starting from the Trifluoroacetate Salt:

To a solution of the appropriate acid (1.5 mmol) in dichloromethane (5 ml), carbonyidiimidazole (CDI, 1.78 mmol) is added. The reaction vessel is equipped with a bubbler, the mixture is stirred until the gas evolution is completed (30 min, approximately). Then, a mixture of the suspension of the appropriate starting trifluoroacetate salt in dichloromethane (10 ml) and triethylamine (0.2 g, 2 mmole) is added to the reaction mixture. Stirring is continued for 18 to 24 hours at room temperature, the reaction is monitored by TLC.

Work up A: if the reaction mixture is a solution, it is extracted by three portions of 5% sodium hydrogencarbonate (10 ml each) and once by water (10 ml), the organic layer is evaporated and the residue subjected to purification.

Work up B: if the reaction mixture is a suspension, the solid product is filtered off. If the amount of this solid product is not sufficient, the mother liquour is further worked up as procedure A.

Purification: The majority of the products can be recrystallized from acetonitrile, in some cases by simple trituration of the organic residue with acetonitrile. After filtration, the crystals are washed with diethyl ether.

b) Starting from the Free Amine using EDCI

A mixture of the appropriate starting base (1 mmol), the appropriate acid (1.5 mmol), ethyl-dimethylaminopropylcarbodiimide (EDCI, 0.29 g, 1.5 mmol), 4-dimethylaminopyridine (DMAP, 0.25 g, 0.2 mmol) and water-free dichloromethane (10 ml) are stirred at room temperature for 18 to 24 hours. The reaction mixture is monitored by TLC. The reaction mixture is worked up as in the reactions carried out with CDI.

c) Using Acid Chlorides

To a suspension of the appropriate starting trifluoroacetate salt (1 mmol) in dichloromethane (10 ml) triethylamine (0.4 g, 4 mmol) is added. The formed solution is added to a solution of the appropriate acid chloride (1.2 mmol) in dichloromethane (10 ml) dropwise at 0° C. with stirring and, then, stirring is continued for 24 h at room temperature. The mixture is evaporated and the residue dissolved in dichloromethane. This solution is extracted twice by water (15 ml) and once by saturated sodium chloride solution (15 ml). Purification is carried out as described in procedures a) and b).

The following compounds can be prepared using the appropriate building blocks (e.g. compound B2) and reagents, which are known to the person skilled in the art or which can be obtained as described exemplarily herein or analogously or similarly thereto, according to the abovementioned preparation A1.

30. N-[3-Cyano-6-(3-1H-indol-3-yl-propanoyl)-4,5,6,7-tetrahydro-thieno[2,3-c]pyridin-2-yl]-benzamide

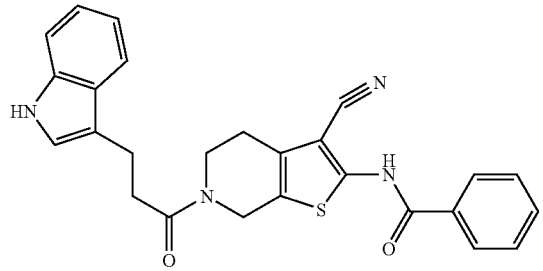

MS: calc.: C26 H22 N4 O2 S (454.55) fnd.: 455.2 [M+H]

31. 3-{3-Cyano-2-[(1-phenyl-methanoyl)-amino]-4,7-dihydro-5H-thieno[2,3-c]pyridin-6-yl}-3-oxo-propionic acid ethyl ester

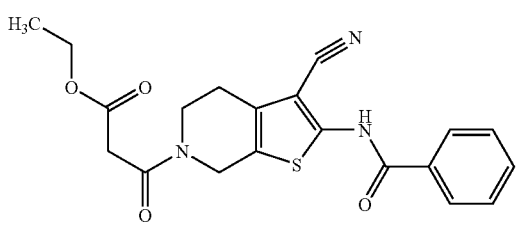

MS: calc.: C20 H19 N3 O4 S (397.46) fnd.: 398.1 [M+H]

32. N-[3-Cyano-6-(2-methoxy-ethanoyl)-4,6,7-tetrahydro-thieno[2,3-c]pyridin-2-yl]-benzamide

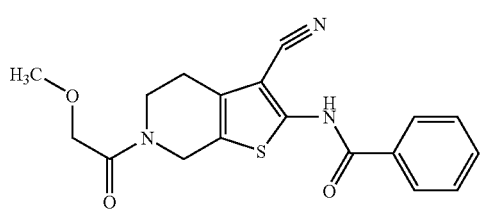

MS: calc.: C18 H17 N3 O3 S (355.42) fnd.: 356.1 [M+H]

33. N-[3-Cyano-6-(3thiazol-2-yl-propanoyl)-4,5,6,7-tetrahydro-thieno[2,3-c]pyridin-2-yl]-benzamide

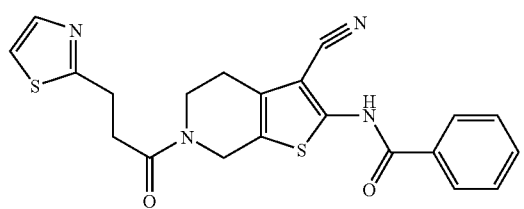

MS: calc.: C21 H18 N4 O2 S2 (422.53) fnd.: 423 [M+H]

34. N-[3-Cyano-6-(3-[1,2,4]triazol-4-yl-propanoyl)-4,5,6,7-tetrahvdro-thieno[2,3-c]pyridin-2-yl]-benzamide

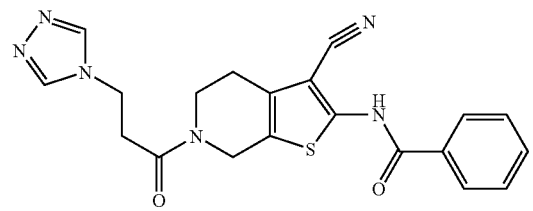

MS: calc.: C20H18N6O2S (406.47). Fnd.: 407.1. [M+H]

35. N-[3-Cyano-6-(2-pyridin-3-yl-ethanoyl)-4,5,6,7-tetrahydro-thieon[2,3-c]pyridin-2-yl]-benzamide

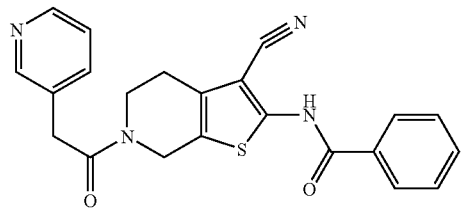

MS: calc.: C22H18N4O2S (402.48). Fnd.: 403.2. [M+H]

36. N-[3-Cyano-6-(2-1H-indol-3-yl-ethanoyl)-4,5,6,7-tetrahydro-thieno[2,3-c]pyridin-2-yl]-benzamide

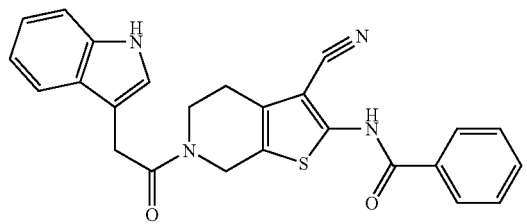

MS: calc.: C25H20N4O2S (440.53). Fnd.: 441.1 [M+H]

37. N-[3-Cyano-6-(4-1H-indol-3-yl-butanoyl)-4,5,6,7-tetrahydro-thieno[2,3-c]pyridin-2-yl]-benzamide

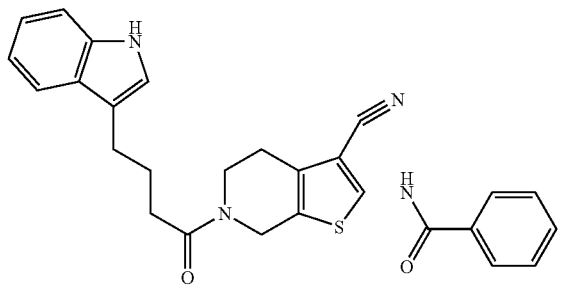

MS: calc.: C27H24N4O2S (468.58). Fnd.: 469.1 [M+H]

38. 5-{3-Cyano-2-[(1-phenyl-methanoyl)-amino]-4,7-dihydro-5H-thieno[2,3-c]pyridin-6-yl}-5-oxo-pentanoic acid methyl ester

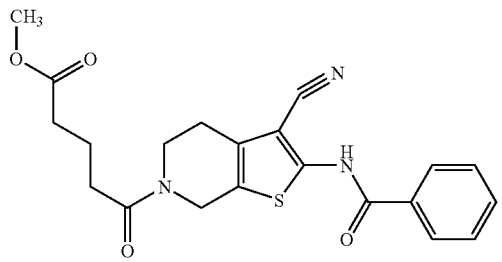

MS: calc.: C21H21N3O4S (411.48). Fnd.: 412 [M+H]

39. N-[3-Cyano6-(3-guanidino-propanoyl)-4,5,6,7-tetrahydro-thieno[2,3-c]pyridin-2-yl]-benzamide

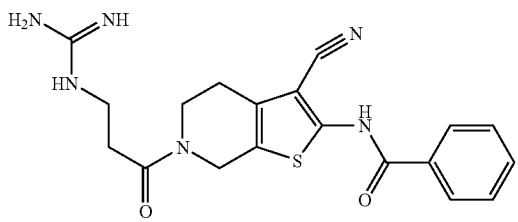

MS: calc.: C19H20N6O2S (396.47). Fnd.: 397.1 [M+H]

40. N-{3-Cyano-6-[2-(2-methoxy-ethoxy]-ethanoyl-4,5,6,7-tetrahydro-thieno[2,3-c]pyridin-2-yl}-benzamide

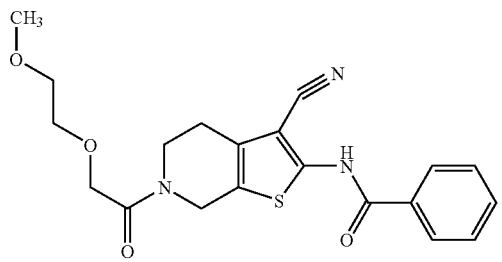

MS: calc.: C20H21N3O4S (399.47) Fnd.: 400.1 [M+H]

41. N-[3-Cyano-6-(3-pyridin-3-yl-propanoyl)-4,5,6,7-tetrahydro-thieno[2,3-c]pyridin-2-yl]-benzamide

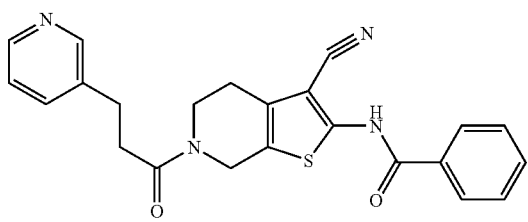

MS: calc.: C23H20N4O2S (416.51) Fnd.: 417.2 [M+H]

42. N-[3-Cyano-6-(2-pyridin-2-yl-ethanoyl)-4,5,7-tetrahydro-thieno[2,3-c]pyridin-2-yl]-benzamide

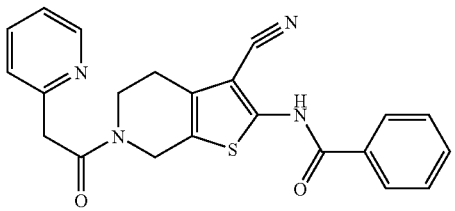

MS: calc.: C22H18N4O2 S (402.48) Fnd.: 403.1 [M+H]

43. N-{3-Cyano-6-[4-(4-methanesulfonyl-phenyl)-4-oxo-butanoyl]-4,5,6,7-tetrahydro-thieno[2,3-c]pyridin-2-yl}-benzamide

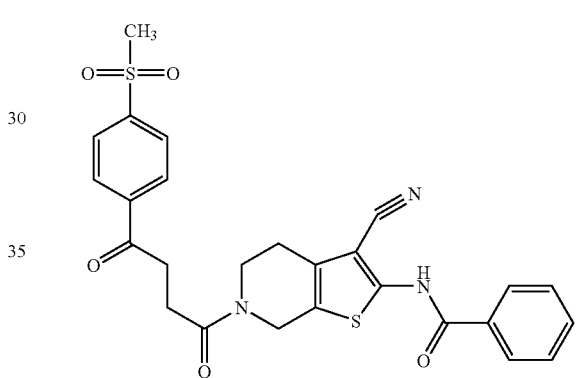

MS: calc.: C26H23N3O5S2 (521.62) Fnd.: 522 [M+H]

A3 Alternative General Procedure for Amide Bond Formation

In a sealable test tube, the corresponding add (1.5 mmol) is suspended in a mixture of DMF (0.15 mmol) and dichloromethane (7.5 mL). A solution of oxalyl chloride (3.0 mmol) in dichloromethane (7.5 mL) is then added and the mixture stirred for 1 h at room temperature. After that, the solvents and excess of oxalyl chloride are removed in vacuo, the residue is dissolved in toluene (7.5 mL) and added to the corresponding amine (1 mmol) in a vial suitable for microwave technology. Diisopropyl ethyl amine (1.5 mmol) is added, the vial capped and the mixture is heated for 30 min at 150° C. using microwave technology Purification is achieved either by filtration followed by washing (water) and crystallization (ethanol) or removal of solvents in vacuo and subsequent column chromatography on silica gel, using mixtures of dichloromethane, methanol and triethyl amine as eluents.

The following compounds can be prepared according to general procedure A3 or analogously to Example 44 starting from 2-amino-3-cyano-4,7-dihydro-5H-thieno[2,3-c]pyridine-6-carboxylic acid ethyl ester (compound A1) and the appropriate benzoic acid derivative.

44. 3-Cyano-2-{[1-(4-nitro-phenyl)-methanoyl]-amino}-4,7-dihydro-5H-thieno[2,3-c]pyridine-6-carboxylic acid ethyl ester

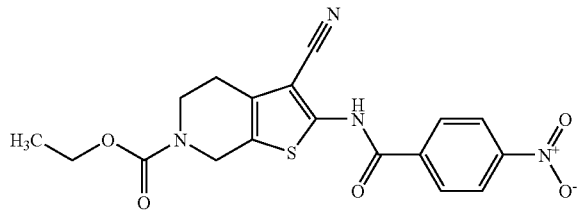

In a sealed test tube p-nitro benzoic acid (1.5 mmol) is suspended in a mixture of DMF (0.15 mmol) and dichloromethane (7.5 mL). A solution of oxalyl chloride (3.0 mmol) in dichloromethane (7.5 mL) is then added and the mixture stirred for 1 h at room temperature. After that, the solvents and excess of oxalyl chloride are removed in vacuo, the residue is dissolved in toulene (7.5 mL) and added to 2-amino-3-cyano-4,7-dihydro-5H-thieno[2,3-c]pyridine-6-carboxylic acid ethyl (1 mmol) in a vial suitable for microwave technology. Diisopropyl ethyl amine (1.5 mmol) is added, the vial is capped and the mixture heated for 30 min at 150° C. using microwave technology. Purification is achieved by filtration followed by washing (water) and crystallization (ethanol).

MS: calc.: C18H16N4O5S (400.42) Fnd.: 401.1 [M+H]

45. 3-Cyano-2{[1-(3-nitro-phenyl)-methanoyl]-amino}-4,7-dihydro-5H-thieno[2,3-c]pyridine-6-carboxylic acid ethyl ester

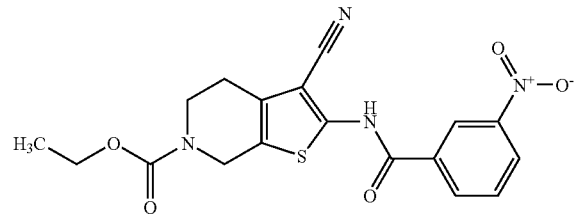

MS: calc.: C18H16N4O5S (400.42) Fnd.: 401.1 [M+H]

46. 3-Cyano-2-{[1-(2-nitro-phenyl)-methanoyl]-amino}-4,7-dihydro-5H-thieno[2,3-c]pyridine-6-carboxylic acid ethyl ester

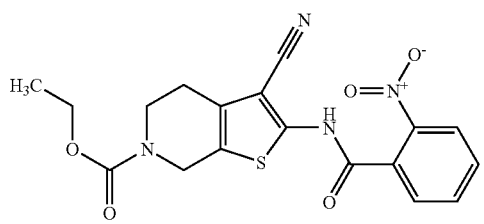

MS: calc.: C18 H16 N4 O5 S (400.42) Fnd.: 401.1 [M+H]

47. 2-{[1-(4-Chloro-phenyl)-methanoyl]-amino}-3-cyano-4,7-dihydro-5H-thieno[2,3-c]pyridin-6-carboxylic acid ethyl ester

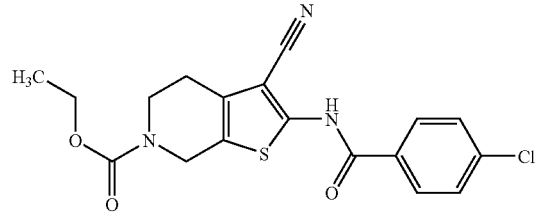

MS: calc.: C18 H16 Cl N3 O3 S (389.86) Fnd.: 390.1 [M+H]

48. 2-{[1-(3-Chloro-phenyl)-methanoyl]-amino}-3-cyano-4,7-dihydro-5H-thieno[2,3-c]pyridine-6-carboxylic acid ethyl ester

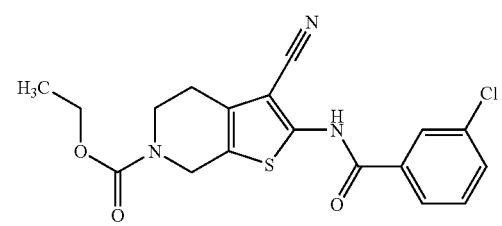

MS: calc.: C18H16ClN3O3S (389.86) Fnd.: 390.1 [M+H]

49. 3-Cyano-2-{[1-(4-methoxy-phenyl)-methanoyl]-amino}-4,7-dihydro-5H-thieno[2,3-c]pyridine-6-carboxylic acid ethyl ester

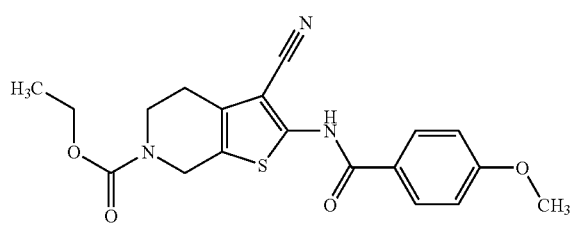

MS: calc.: C19H19N3O4S (385.44) Fnd.: 386.1 [M+H]

50. 3-Cyano-2-[(1-p-tolyl-methanoyl)-amino]-4,7-dihydro-5H-thieno[2,3-c]pyridine-6-carboxylic acid ethyl ester

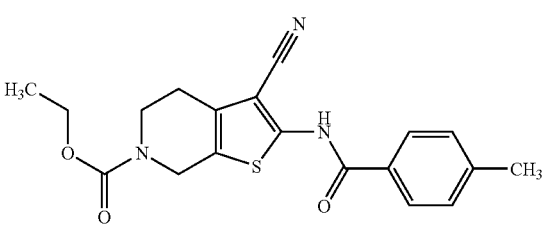

MS: calc.: C19H19N3O3S (369.45) Fnd.: 370.2 [M+H]

51. 3-Cyano-2-[(1-m-tolyl-methanoyl)-amino]-4,7-dihydro-5H-thieno[2,3-c]pyridine-6-carboxylic acid ethyl ester

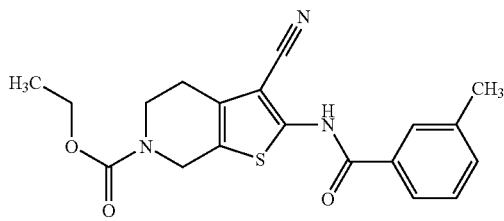

MS: calc.: C19H19N3O3S (369.45) Fnd.: 370.1 [M+H]

52. 3-Cyano-2-[(1-o-tolyl-methanoyl)-amino]-4,7-dihydro-5H-thieno[2,3-c]pyridine-6-carboxylic acid ethyl ester

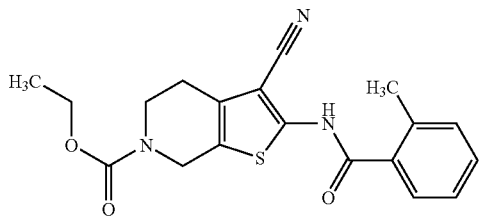

MS: calc.: C19H19N3O3S (369.45) Fnd.: 370.1 [M+H]

53. 3-Cyano-2-{[1-(3-hydroxy-phenyl)-methanoyl]-amino}-4,7-dihydro-5H-thieno[2,3-c]pyridine-6-carboxylic acid ethyl ester

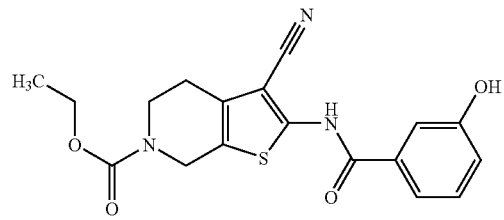

3-cyano-2-{[1-(3-methoxy-phenyl)-methanoyl]-amino}-4,7-dihydro-5H-thieno[2,3-c]pyridine-6-carboxylic acid ethyl ester (0.16 mmol) is dissolved in 2.4 ml dichloromethane. 1.22 ml BBr$_3$ (1M in dichloromethane) is added at −78° C. and the reaction mixture is stirred for 20 hours at room temperature. After aqueous workup and evaporation of the solvent, the curde product is recristallized from ethanol.

MS: calc.: C18H17N3O4S (371.42) Fnd.: 372.2 [M+H]

The following compounds can be prepared using the appropriate building blocks (e.g. compound B2) and reagents, which are known to the person skilled in the art or which can be obtained as described exemplarily herein or analogously or similarly thereto, according to the belowmentioned preparation E1.

54. 3-Cyano-2-[(1-phenyl-methanoyl)-amino]-4,7-dihydro-5H-thieno[2,3-c]pyridine-6-carboxylic acid methyl ester

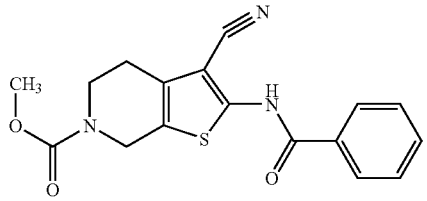

MS: calc.: C17H15N3O3S (341.39) Fnd.: 342.2 [M+H]

55. 3-Cyano-2-[(1-phenyl-methanoyl)-amino]-4,7-dihydro-5H-thieno[2,3-c]pyridine-6-carboxylic acid 2-(4-methyl-thiazol-5-yl)-ethyl ester

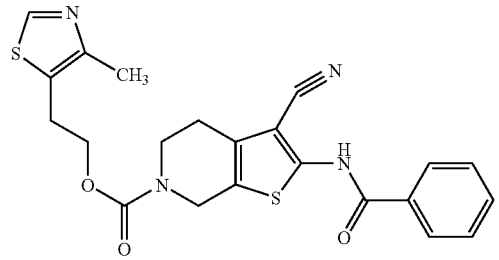

MS: calc.: C22H20N4O3S2 (452.56) Fnd.: 453.2 [M+H]

56. 3-Cyano-2-[(1-phenyl-methanoyl)-amino]-4,7-dihydro-5H-thieno[2,3-c]pyridine-6-carboxylic acid isobutyl ester

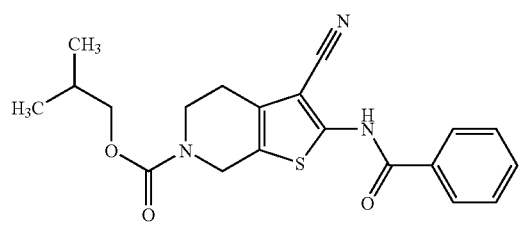

MS: calc.: C20H21N3O3S (383.47) Fnd.: 384.1 [M+H]

57. 3-Cyano-2-[(1-phenyl-methanoyl)-amino]-4,7-dihydro-5H-thieno[2,3-c]pyridine-6-carboxylic acid hexyl ester

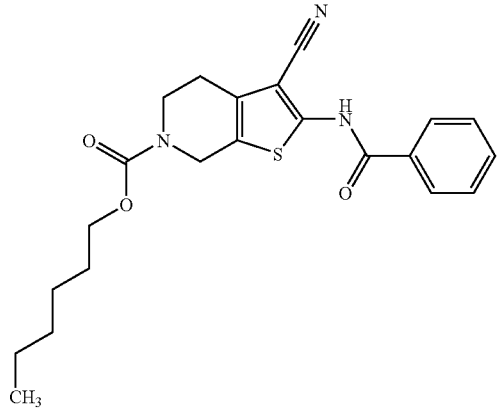

MS: calc.: C22H25N3O3S (411.53) Fnd.: 412.1 [M+H]

58. 3-Cyano-2-[(1-phenyl-methanoyl)-amino]-4,7-dihydro-5H-thieno[2,3-c]pyridine-6-carboxylic acid butyl ester

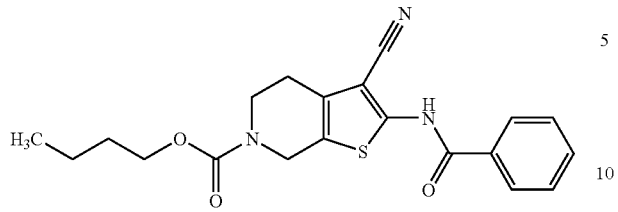

MS: calc.: C20H21N3O3S (383.47) Fnd.: 384.1 [M+H]

59. 3-Cyano-2-[(1-phenyl-methanoyl)-amino]-4,7-dihydro-5H-thieno[2,3-c]pyridine-6-carboxylic acid phenyl ester

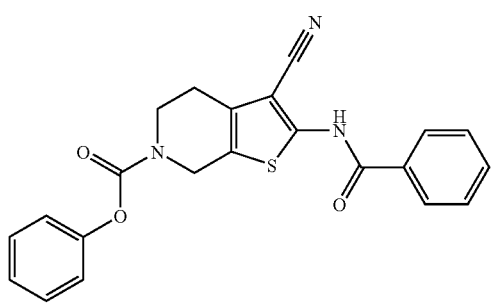

MS: calc.: C22H17N3O3S (403.46) Fnd.: 404.1 [M+H]

60. 3-Cyano-2-[(1-phenyl-methanoyl)-amino]-4,7-dihydro-5H-thieno[2,3-c]pyridine-6-carboxylic acid 4-methoxy-phenyl ester

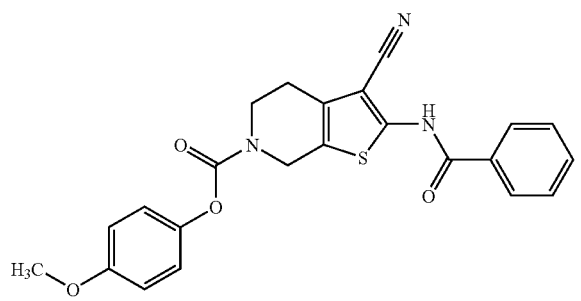

MS: calc.: C23H19N3O4S (433.49) Fnd.: 434.1 [M+H]

61. 3-Cyano-2-[(1-phenyl-methanoyl)-amino]-4,7-dihydro-5H-thieno[2,3-c]pyridine-6-carboxylic acid benzyl ester

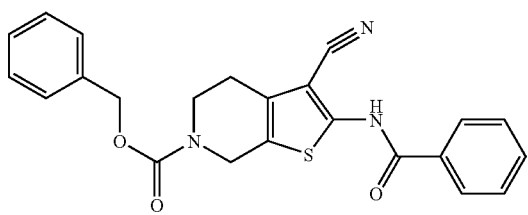

MS: calc.: C23H19N3O3S (417.49) Fnd.: 417.9 [M+H]

62. 3-Cyano-2-[(1-phenyl-methanoyl)-amino]-4,7-dihydro-5H-thieno[2,3-c]pyridine-6-carboxylic acid pyridin-2-ylmethyl ester

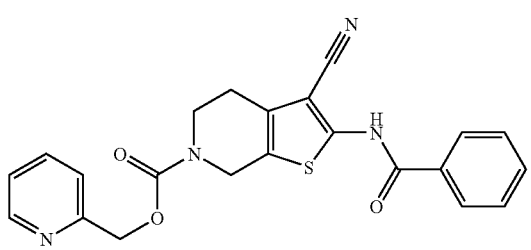

MS: calc.: C22H18N4O3S (418.48) Fnd.: 413.1 [M+H]

63. 3-Cyano-2-[(1-phenyl-methanoyl)-amino]-4,7-dihydro-5H-thieno[2,3-c]pyridine-6carboxylic acid pyridin-3-ylmethyl ester

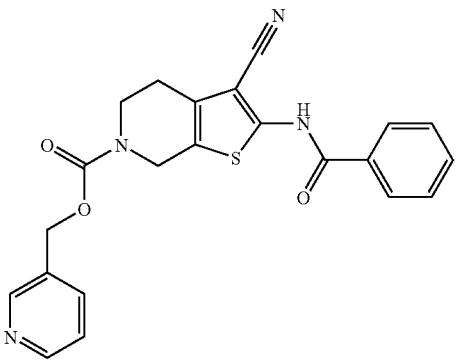

MS: calc.: C22H18N4O3S (418.48) Fnd.: 419.2 [M+H]

64. 3-Cyano-2-[(1-phenyl-methanoyl)-amino]-4,7-dihydro-5H-thieno[2,3-c]pyridine-6-carboxylic acid propyl ester

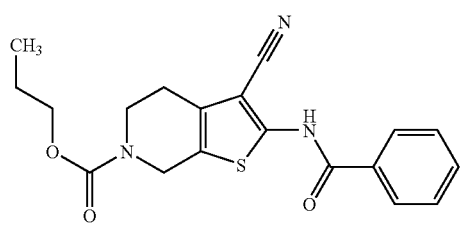

MS: calc.: C19 H19 N3 O3 S (369.45) Fnd.: 370.1 [M+H]

65. 3-Cyano-2-[(1-phenyl-methanoyl)-amino]-4,7-dihydro-5H-thieno[2,3-c]pyridine-6-carboxylic acid phenethyl ester 68. 3-Cyano-2-[(1-phenyl-methanoyl)-amino]-4,7-dihydro-5H-thieno[2,3-c]pyridine-6-carboxylic acid 2-pyridin-2-yl-ethyl ester

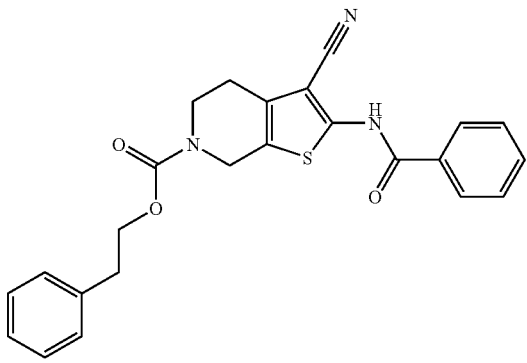

MS: calc.: C24H21N3O3S (431.52) Fnd.: 432.1 [M+H]

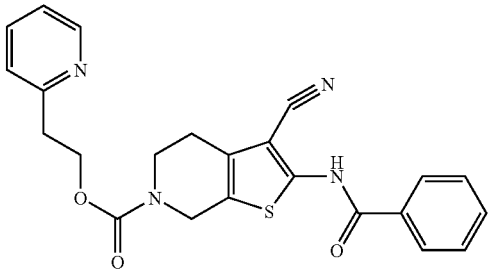

MS: calc.: C23 H20 N4 O3 S (432.5) Fnd.: 433.1 [M+H]

66. 3-Cyano-2-[(1-phenyl-methanoyl)-amino]-4,7-dihydro-5H-thieno[2,3-c]pyridine-6-carboxylic acid pyridin-4-ylmethyl ester 69. 3-Cyano-2-[(1-phenyl-methanoyl)-amino]-4,7-dihydro-5H-thieno[2,3-c]pyridine-6-carboxylic acid 3-pyridin-4-yl-propyl ester

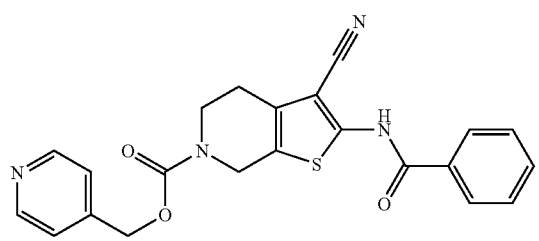

MS: calc.: C22H18N4O3S (418.48) Fnd.: 419.3 [M+H]

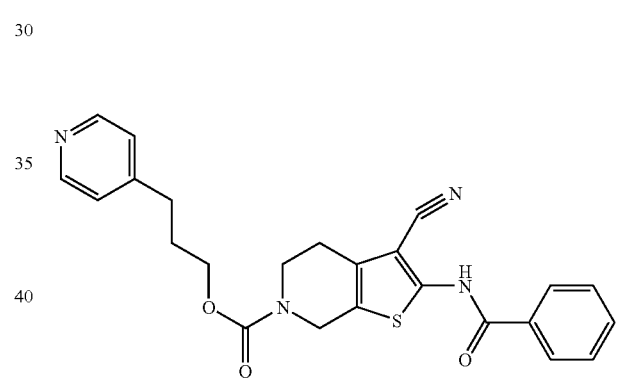

MS: calc.: C24 H22 N4 O3 S (446.53) Fnd.: 447.3 [M+H]

67. 3-Cyano-2-[(1-phenyl-methanoyl)-amino]4,7-dihydro-5H-thieno[2,3-c]pyridine-6-carboxylic acid 2-morpholin-4-yl-ethyl ester 70. 3-Cyano-2-[(1-phenyl-methanoyl)-amino]-4,7-dihydro-5H-thieno[2,3-c]pyridine-6-carboxylic acid 3-morpholin-4-yl-propyl ester

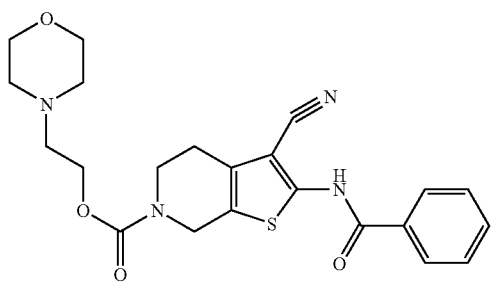

MS: calc.: C22 H24 N4 O4 S (440.52) Fnd.: 441.2 [M+H]

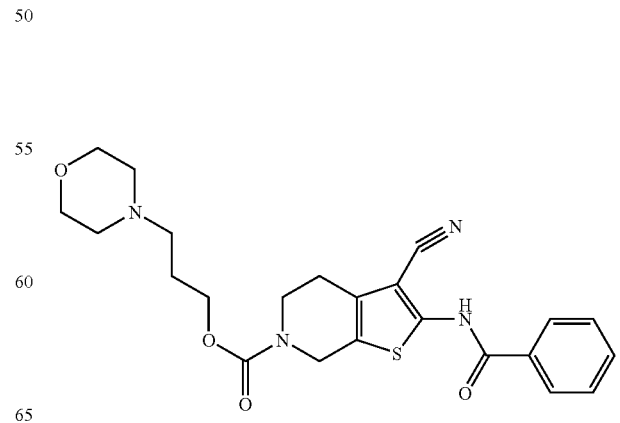

MS: calc.: C23 H26 N4 O4 S (454.55) Fnd.: 455.2 [M+H]

71. 3-Cyano-2-[(1-phenyl-methanoyl)-amino]-4,7-dihydro-5H-thieno[2,3-c]pyridine-6-carboxylic acid 3-pyridin-2-yl-propyl ester

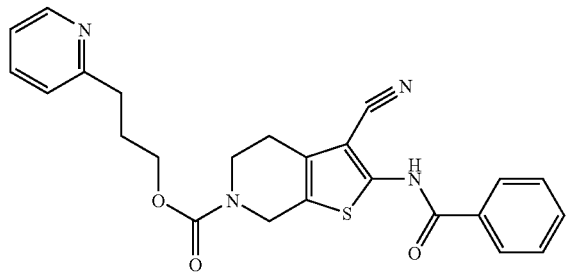

MS: calc.: C24 H22 N4 O3 S (446.53) Fnd.: 447.1 [M+H]

72. 3-Cyano-2-[(1-phenyl-methanoyl)-amino]-4,7-dihydro-5H-thieno[2,3-c]pyridine-6-carboxylic acid 3-pyridin3-yl-propyl ester

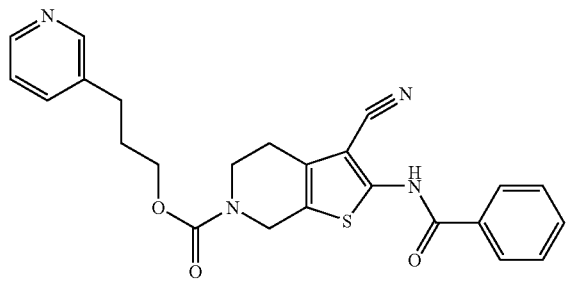

MS: calc.: C24 H22 N4 O3 S (446.53) Fnd.: 447.2 [M+H]

73. 3-Cyano-2-[(1-phenyl-methanoyl)-amino]4,7-dihydro-5H-thieno[2,3-c]pyridine-6-carboxylic acid 2-pyridin4-yl-ethyl ester

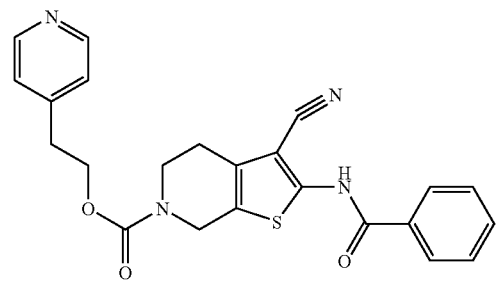

MS: calc.: C23 H20 N4 O3 S (432.5) Fnd.: 433.1 [M+H]

74. 3-Cyano-2-[(1-phenyl-methanoyl)-amino]-4,7-dihydro-5H-thieno[2,3-c]pyridine-6-carboxylic acid 2,2-dimethyl-[1,3]dioxolan-4-ylmethyl ester

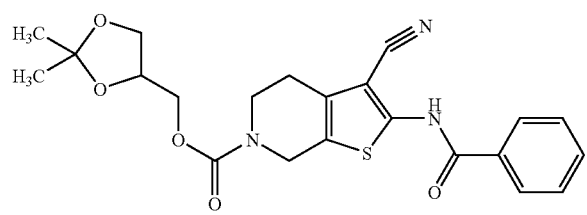

MS: calc.: C22 H23 N3 O5 S (441.51) Fnd.: 442 [M+H]

75. 3-Cyano-2-[(1-phenyl-methanoyl)amino]-4,7-dihydro-5H-thieno[2,3-c]pyridine-6-carboxylic acid 2-(2-methoxy-ethoxy)-ethyl ester

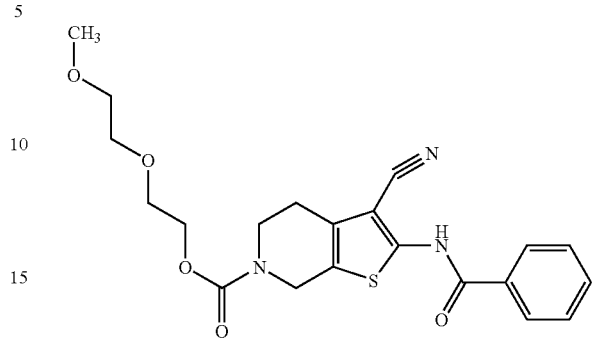

MS: calc.: C21 H23 N3 O5 S (429.5) Fnd.: 430 [M+H]

76. 3-Cyano-2-[(1-phenyl-methanoyl)-amino]-4,7-dihydro-5H-thieno[2,3-c]pyridine-6-carboxylic acid 2,3-dihydroxy-propyl ester

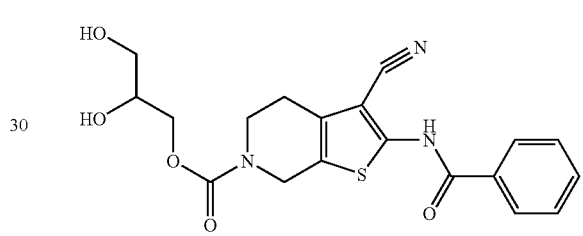

0.26 mmol of 3-Cyano-2-[(1-phenyl-methanoyl)-amino]-4,7-dihydro-5H-thieno[2,3-c]pyridine-6-carboxylic acid 2,2-dimethyl-[1,3]dioxolan-4-ylmethyl ester are dissolved in 10 ml AcCN/H2O (2/1) and 0.1 eq PTSA is added. After stirring over night, some triethylamine is added and the solvent removed. Recrystalization from ethanol gives the desired product in 80% yield.

MS: calc.: C19 H19 N3 O5 S (401.44) Fnd.: 402.1 [M+H]

The following compounds can be prepared using the appropriate building blocks (e.g. compound B2) and reagents, which are known to the person skilled in the art or which can be obtained as described exemplarily herein or analogously or similarly thereto, according to the belowmentioned preparation D1.

77. N-[3-Cyano-6-(6-morpholin-4-yl-pyridine-3-sulfonyl)-4,5,6,7-tetrahydro-thieno[2,3-c]pyridin-2-yl]-benzamide

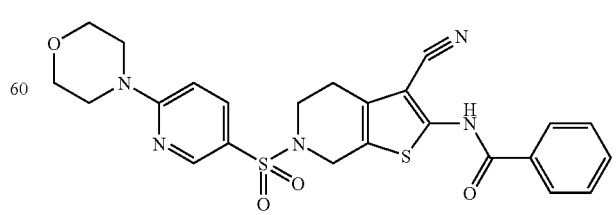

MS: calc.: C24 H23 N5 O4 S2 (509.61) Fnd.: 510.2 [M+H]

78. N-[3-Cyano-6-(5-methyl-1-phenyl-1H-pyrazole-4-sulfonyl)-4,5,6,7-tetrahydro-thieno[2,3-c]pyridin-2-yl]-benzamide

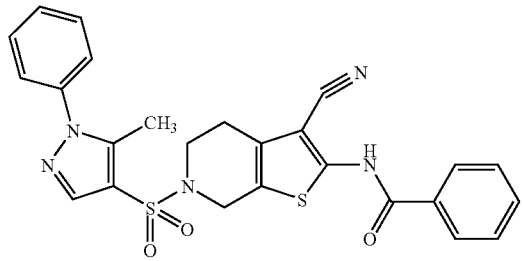

MS: calc.: C25 H21 N5 O3 S2 (503.61) Fnd.: 504.1. [M+H]

79. N-[3-Cyano-6-(4-methoxy-benzenesulfonyl)-4,5,6,7-tetrahydro-thieno[2,3-c]pyridin-2-yl]-benzamide

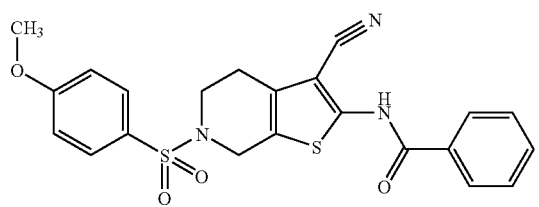

MS: calc.: C22 H19 N3 O4 S2 (453.54) Fnd.: 454.1. [M+H]

The following compounds can be prepared using the appropriate building blocks (e.g. compound B2) and reagents, which are known to the person skilled in the art or which can be obtained as described exemplarily herein or analogously or similarly thereto, according to the belowmentioned preparation F.

80. 3-Cyano-2-[(1-phenyl-methanoyl)-amino]-4,7-dihydro-5H-thieno[2,3-c]pyridine-6-carboxylic acid (2-pyridin-4-yl-ethyl)-amide

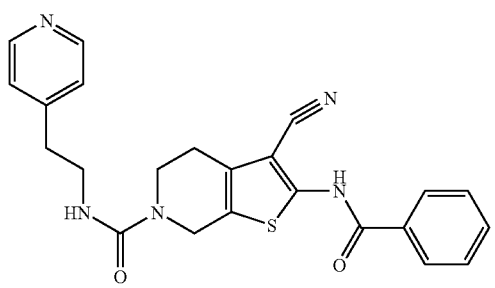

MS: calc.: C23 H21 N5 O2 (431.52) Fnd.: 432.1 [M+H]

81. 3-Cyano-2-[(1-phenyl-methanoyl)-amino]-4,7-dihydro-5H-thieno[2,3-c]pyridine-6-carboxylic acid [2-(1H-indol-3-yl)-ethyl]-amide

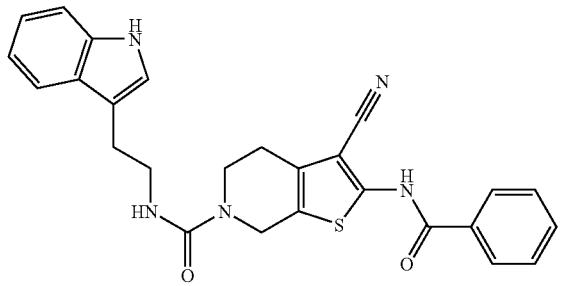

MS: calc.: C26 H23 N5 O2S (469.57) Fnd.: 470.1 [M+H]

82. 3-Cyano-2-[(1-phenyl-methanoyl)amino]-4,7-dihydro-5H-thieno[2,3-c]pyridine-6-carboxylic acid [2-(4-nitro-phenyl)-ethyl]-amide

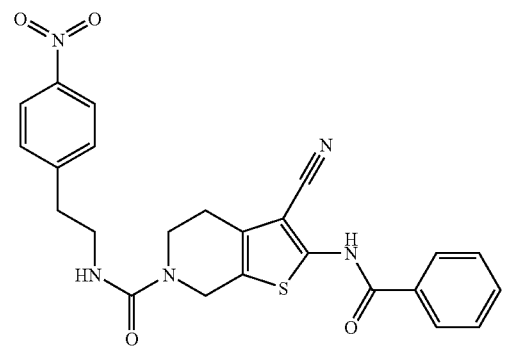

MS: calc.: C24 H21 N5 O4S (475.53) Fnd.: 476 [M+H]

The following compounds can be prepared using the appropriate building blocks (e.g. compound B2) and reagents, which are known to the person skilled in the art or which can be obtained as described exemplarily herein or analogously or similarly thereto, according to the abovementioned preparation A1.

83. N-[3-Cyano-6-(3-dimethylcarbamoyl-propanoyl)-4,5,6,7-tetrahydro-thieno[2,3-c]pyridin-2-yl]-benzamide

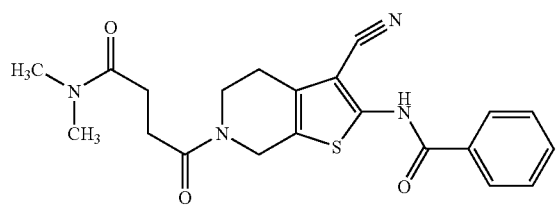

MS: calc.: C21 H22 N4 O3 S (410.5) Fnd.: 411.0 [M+H]

84. Acetic acid 2-3-cyano-2-[(1-phenyl-methanoyl)-amino]-4,7-dihydro-5H-thieno[2,3-c]pyridin-6-yl-2-oxo-ethyl ester

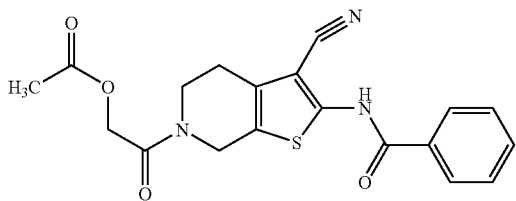

MS: calc: C19 H17 N3 O4 S (383.43) Fnd.: 384.0. [M+H]

85. N-[3-Cyano-6-(4-imidazol-1-yl-butanoyl)-4,5,6,7-tetrahydro-thieno[2,3-c]pyridin-2-yl]-benzamide

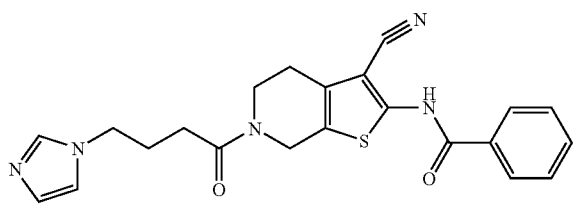

MS: calc.: C22 H21 N5 O2 S (419.51) Fnd.: 420.1 [M+H]

86. Acetic acid 4-{3-cyano-2-[(1-phenyl-methanoyl)-amino]4,7-dihydro-5H-thieno[2,3-c]pyridin-6-yl}-4-oxo-butyl ester

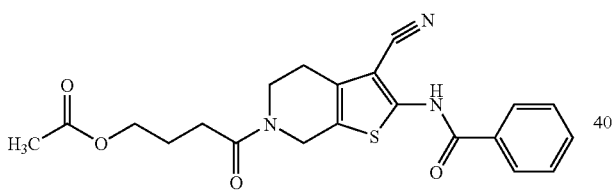

MS: calc.: C21 H21 N3 O4 S (411.48) Fnd.: 412.0 [M+H]

87. N-[3-Cyano-6-(2-hydroxy-ethanoyl)-4,5,6,7-tetrahydro-thieno[2,3-c]pyridin-2-yl]-benzamide

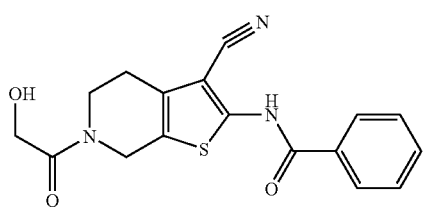

Acetic acid 2{3-cyano-2-[(1-phenyl-methanoyl)-amino]-4,7-dihydro-5H-thieno[2,3-c]pyridin-6-yl}-2-oxo-ethyl ester is stirred on 1N NaOH over night at room temperature. Workup as described in general procedure A3 gives the desired product.

MS: calc.: C17 H15 N3 O3 S (341.39) Fnd.: 342.0 [M+H]

88. N-[3-Cyano-6-(4-hydroxy-butanoyl)-4,5,6,7-tetrahydro-thieno[2,3-c]pyridin-2-yl]-benzamide

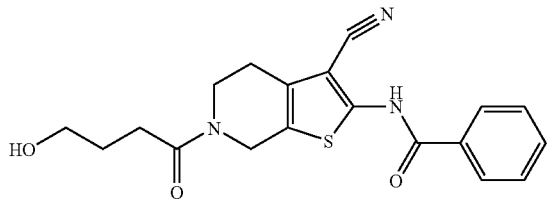

The title compound can be prepared from compound 86 similarly as described for compound 87.

MS: calc.: C19 H19 N3 O3 S (369.45) Fnd.: 370.0 [M+H]

The following compounds can be prepared using the appropriate building blocks (e.g. compound B2) and reagents, which are known to the person skilled in the art or which can be obtained as described exemplarily herein or analogously or similarly thereto, according to the belowmentioned preparation E1.

89. 3-Cyano-2-[(1-phenyl-methanoyl)-amino]4,7-dihydro-5H-thieno[2,3-c]pyridine-6-carboxylic acid 2-dimethylamino-ethyl ester

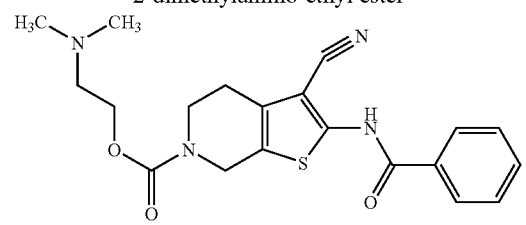

MS: calc.: C20 H22 N4 O3 S (398.49) Fnd.: 399.1 [M+H]

90. 3-Cyano-2-[(1-phenyl-methanoyl)-amino]4,7-dihydro-5H-thieno[2,3-c]pyridine-6-carboxylic acid 2-pyrrolidin-1-yl-ethyl ester

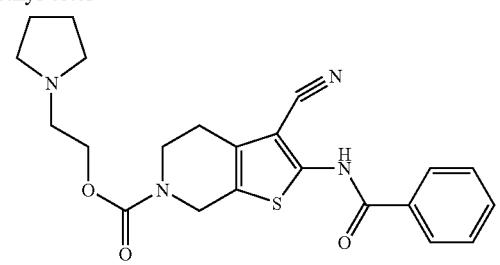

MS: calc.: C22 H24 N4 O3 S (424.53) Fnd.: 425.2 [M+H]

91. 3-Cyano-2-[(1-phenyl-methanoyl)-amino]-4,7-dihydro-5H-thieno[2,3-c]pyridine-6-carboxylic acid 3-(4-methyl-piperazin-1-yl)-propyl ester

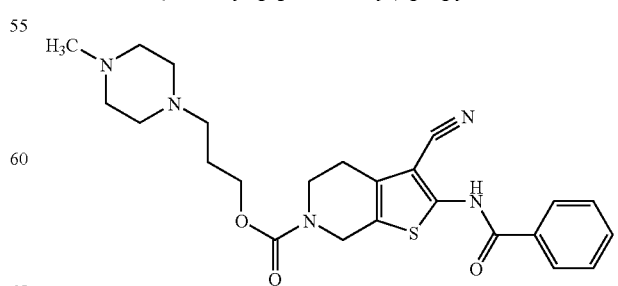

MS: calc.: C24 H29 N5 O3 S (467.59) Fnd.: 468.2 [M+H]

92. 3-Cyano-2-[(1-phenyl-methanoyl)-amino]4,7-dihydro-5H-thieno[2,3-c]pyridine-6-carboxylic acid 2-piperidin-1-yl-ethyl ester

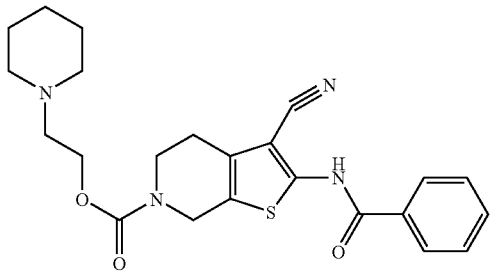

MS: calc.: C23 H26 N4 O3 S (438.55) Fnd.: 439.2 [M+H]

93. 3-Cyano-2-[(1-phenyl-methanoyl)-amino]-4,7-dihydro-5H-thieno[2,3-c]pyridine-6-carboxylic acid methoxycarbonylmethyl ester

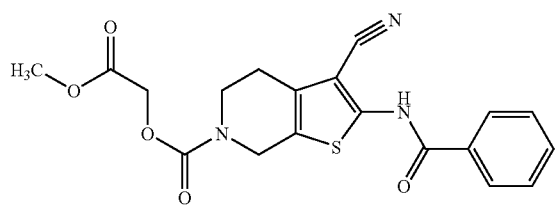

MS: calc.: C19 H17 N3 O5 S (399.43) Fnd.: 400.0 [M+H]

94. 3-Cyano-2-[(1-phenyl-methanoyl)-amino]4,7-dihydro-5H-thieno[2,3-c]pyridine-6-carboxylic acid 2-acetylamino-ethyl ester

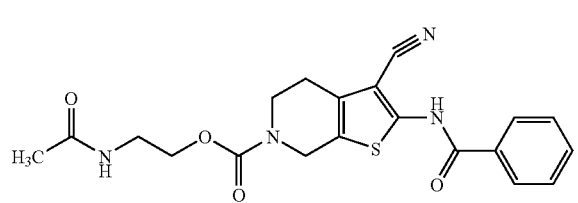

MS: calc.: C20 H20 N4 O4 S (412.47) Fnd.: 413.1 [M+H]

95. 3-Cyano-2-[(1-phenyl-methanoyl-amino]4,7-dihydro-5H-thieno[2,3-c]pyridine-6-carboxylic acid 2-imidazol-1-yl-ethyl ester

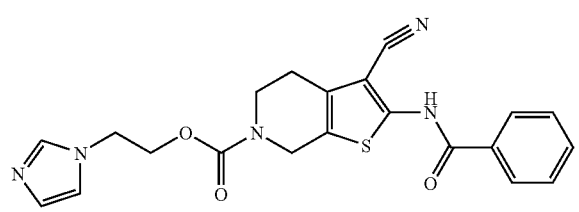

MS: calc.: C21 H19 N5 O3 S (421.48) Fnd.: 422.1 [M+H]

96. 3-Cyano-2-[(1-phenyl-methanoyl)-amino]-4,7-dihydro-5H-thieno[2,3-c]pyridine-6-carboxylic acid 2-acetoxy-ethyl ester

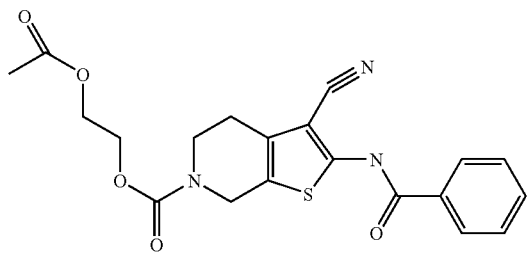

97. 3-Cyano-2-[(1-phenyl-methanoyl)-amino]-4,7-dihydro-5H-thieno[2,3-c]pyridine-6-carboxylic acid 2-hydroxy-ethyl ester

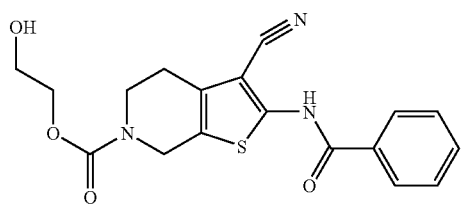

The title compound can be prepared from compound 96 similarly as described for compound 87.

MS: calc.: C18 H17 N3 O4 S (371.42) Fnd.: 372.1 [M+H]

The following compounds can be prepared using the appropriate building blocks (e.g. compound B2) and reagents, which are known to the person skilled in the art or which can be obtained as described exemplarily herein or analogously or similarly thereto, according to the belowmentioned preparation F. 98. 3-Cyano-2-[(1-phenyl-methanoyl)-amino]-4,7-dihydro-5H-thieno[2,3-c]pyridine-6-carboxylic acid ethylamide

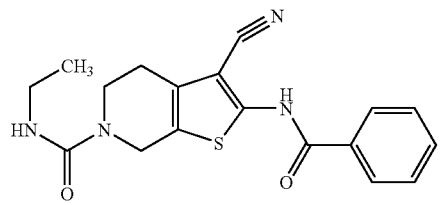

MS: calc.: C18 H18 N4 O2 S (354.43) Fnd.: 355.0 [M+H]

99. 3-Cyano-2-[(1-phenyl-methanoyl)-amino]-4,7-dihydro-5H-thieno[2,3-c]pyridine-6-carboxylic acid (2-pyridin-2-yl-ethyl)-amide

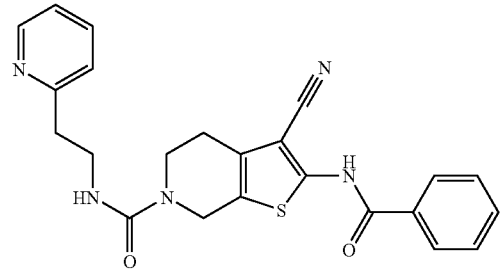

MS: calc.: C23 H21 N5 O2 S (431.52) Fnd.: 432.1 [M+H]

100. 3-Cyano-2-[(1-phenyl-methanoyl)-amino]-4,7-dihydro-5H-hieno[2,3-c]pyridine-6-carboxylic acid (3-ethoxy-propyl)-amide

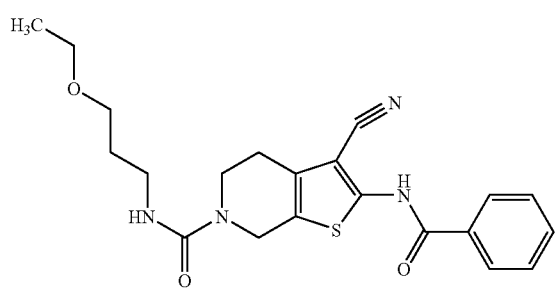

MS: calc.: C21 H24 N4 O3 S (412.51) Fnd.: 413.0 [M+H]

The following compounds can be prepared using the appropriate building blocks (e.g. compound B2) and reagents, which are known to the person skilled in the art or which can be obtained as described exemplarily herein or analogously or similarly thereto, according to the belowmentoned preparation G1.

101. 3-Cyano-2-[(1-phenyl-methanoyl)-amino]-4,7-dihydro-5H-thieno[2,3-c]pyridine6-carbothioic acid S-pentyl ester

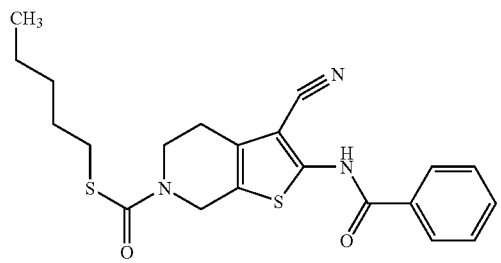

MS: calc.: C21 H23 N3 O2 S2 (413.56) Fnd.: 414.2 [M+H]

102. 3-(1{3-Cyano-2-[(1-phenyl-methanoyl)-amino]-4,7-dihydro-5H-thieno[2,3-c]pyridin-6-yl}-methanoylsulfanyl)-propionic acid methyl ester

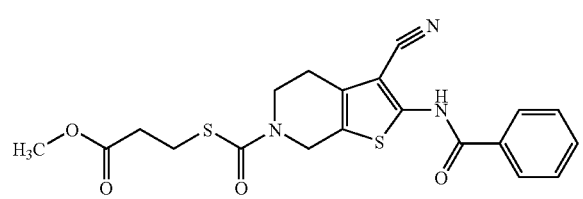

MS: calc.: C20 H19 N3 O4 S2 (429.52) Fnd.: 430.0 [M+H]

103. 3-(1-{3-Cyano-2-[(1-phenyl-methanoyl)-amino]-4,7-dihydro-5H-thieno[2,3-c]pyridin-6-yl}-methanoylsulfanyl)-propionic acid

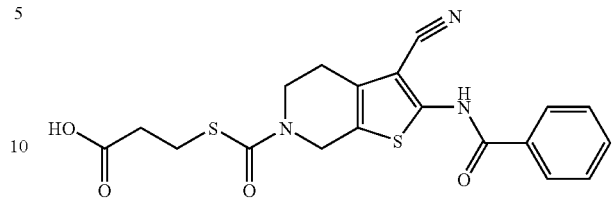

The title compound can be obtained from compound 102 by art-known saponification reaction.

MS: calc.: C19 H17 N3 O4 S2 (415.49) Fnd.: 416.0 [M+H]

Starting Materials:

A1. 2-Amino-3-cyano-4,7-dihydro-thieno[2,3-c]pyridine-6(5H)-carboxylic acid ethyl ester

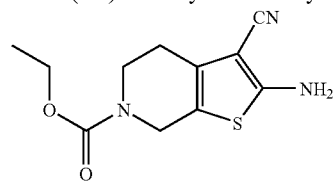

Prepared according to general procedure B described below starting from N-carbethoxy4-piperidone.

MS: calc.: $C_{11}H_{13}N_3O_2S$ (251.31). Fnd.: 252.0 [M+H]

B. General Procedure for Condensed 2-amino-thiophene-3-carbonitrile Derivatives 500 mmol of cyclic ketone and 500 mmol of malononitrile are dissolved in a minimal volume of ethanol and 500 mmol elemental sulfur are added. After addition of 500 mmol diethyl amine, the reaction mixture is heated to 60-70° C. for some minutes and then stirred at room temperature for several hours. The reaction mixture is poured on ice/water and the precipitate filtered off. In case there is no or only some precipitate formed, the aqueous layer is extracted several times with dichloromethane or another appropriate organic solvent, the combined organic layers are dried (e.g. MgSO$_4$) and concentrated in vacuo. Purification of the crude product is achieved by flash chromatography and/or recristallization from an appropriate solvent (e.g. ethanol).

A2. 2-Amino-3-cyano-4,7-dihydro-thieno[2,3-c]pyridine-6(5H)-carboxylic acid 1,1-dimethylethyl ester

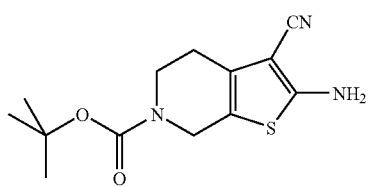

Prepared according to general procedure B starting from Boc4-piperidone.

MS: calc.: $C_{13}H_{17}N_3O_2S$ (279.36). Fnd.: 280.0 [M+H]

A3. 6-Acetyl-2-amino-3-cyano-4,5,6,7-tetrahydro-thieno[2,3-c]pyridine

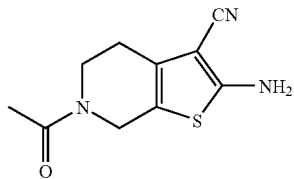

Prepared according to general procedure B starting from acetyl4-piperidone.
MS: calc.: $C_{10}H_{11}N_3OS$ (221.28). Fnd.: 222.0 [M+H]

B1. N-(3-cyano-4,5,6,7-tetrahydro-thieno[2,3-c]pyridin-2-yl)-3,5-dimethoxybenzamide

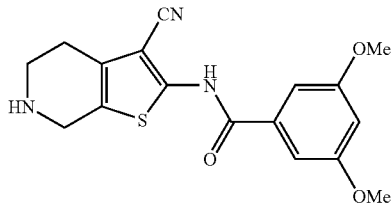

Prepared according to general procedure C starting from N-(6-tert.-butyloxycarbonyl-3-cyano-4,5,6,7-tetrahydro-thieno[2,3-c]pyridin-2-yl)-3,5-dimethoxybenzamide (compound 2).
MS: calc.: $C_{17}H_{17}N_3O_3S$ (343.41). Fnd.: 344.0 [M+H]

B2. N-(3-cyano-4,5,6,7-tetrahydro-thieno[2,3-c]pyridin-2-yl)-benzamide

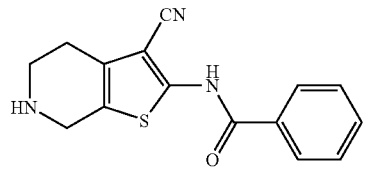

Prepared according to general procedure C starting from N-(6-tert.-butyloxycarbonyl-3-cyano4,5,6,7-tetrahydro-thieno[2,3-c]pyridin-2-yl)-benzamide (compound 1).
MS: calc.: $C_{15}H_{13}N_3OS$ (283.35). Fnd.: 284.0 [M+H]

B3. N-(3-Cyano-4,5,6,7-tetrahydro-thieno[2,3-c]pyridin-2-yl)-3-methoxybenamide

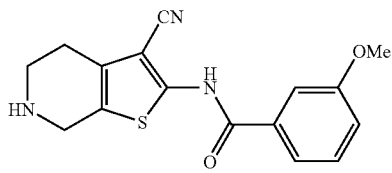

Prepared according to general procedure C starting from N-(6-tert.-butyloxycarbonyl-3-cyano-4,5,6,7-tetrahydro-thieno[2,3-c]pyridin-2-yl)-3-methoxybenzamide (compound 3).
MS: calc.: $C_{16}H_{15}N_3O_2S$ (313.38). Fnd.: 314 [M+H]

B4. N-(3Cyano-4,5,6,7-tetrahydro-thieno[2,3-c]pyridin-2-yl)-3,5-dimethoxybenamide

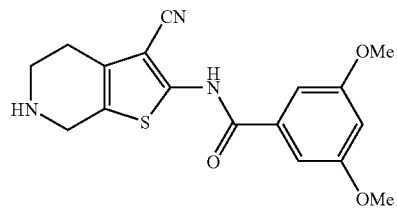

The title compound can be prepared according to general procedure C starting from N-(6-tert.-butyloxycarbonyl-3-cyano-4,5,6,7-tetrahydro-thieno[2,3-c]pyridin-2-yl)-3,5-dimethoxybenzamide (compound 2).

C. General Procedure for Removal of Boc Protecting Groups

The Boc protected compound is dissolved in dichloromethane/trifluoroacetic acid (TFA) (2/3) and stirred for several hours at room temperature. After evaporation of the solvent and recristalization from an appropriate solvent (e.g. ethanol), the desired product is obtained as TFA salt. The TFA salt may be converted into the free base in a manner customary per se to the skilled person.

D. General Procedure for Sulfonamide Bond Formation 100 mmol of the amine and 150 mmol of the sulfonyl chloride are dissolved in pyridine and stirred for some time at room temperature and, if necessary, is heated for some time either by conventional or microwave assisted heating. Then the solvent is either removed in vacuo or the reaction mixture is partitioned between water and an appropriate solvent (e.g. ethyl acetate). In the second case, the aqueous layer is extracted several times with the organic solvent, the combined organic layers are dried (e.g. $MgSO_4$) and concentrated in vacuo. Purification of the crude product is achieved by flash chromatography and/or recristalization from an appropriate solvent (e.g. ethanol).

D1. Alternative General Procedure for Sulfonamide Bond Formation 100 mmol of the amine and 150 mmol of the sulfonyl chloride are dissolved in pyridine and stirred for some time at room temperature and, if necessary, is heated for some time either by conventional or microwave assisted heating. Then the solvent is either removed in vacuo or the reaction mixture is partitioned between water and an appropriate solvent (e.g. ethyl acetate). In the second case, the aqueous layer is extracted several times with the organic solvent, the combined organic layers are dried (e.g. MgSO4) and concentrated in vacuo. Purification of the crude product is achieved by flash chromatography and/or recristalization from an appropriate solvent (e.g. ethanol).

E. General Procedure for Carbamate Formation 100 mmol pyridine and 65 mmol triphosgene are dissolved in dichloromethane. 65 mmol of the alcohol are added at 0° C. and the reaction is stirred at room temperature for 3 hours. This solution is added to 200 mmol of the amine in dichloromethane at −78° C. and the reaction mixture is allowed to warm to room temperature and stirred for some time. Then the solvent is either removed in vacuo or the reaction mixture is partitioned between water and an appropriate solvent (e.g. ethyl acetate). In the second case, the aqueous layer is extracted several times with the organic solvent, the combined organic layers are dried (e.g. $MgSO_4$) and concentrated in vacuo. Purification of the crude product is achieved by flash chromatography and/or recristalization from an appropriate solvent (e.g. ethanol).

E1. Alternative General Procedure for the Preparation of Carbamates

A) Preparation of the imidazole 1-carboxylic ester reagents:

A solution of the appropriate alcohol (10 mmol), 1,1'-carbonyidiimidazole (10 mmol) in dichloromethane (20 ml) is stirred at room temperature for 2 to 3 h while the reaction is monitored by TLC. Then the reaction mixture is extracted by three portions of 10% sodium hydrogencarbonate solution and once by water. The organic layer is dried over sodium sulfate and evaporated to yield a pale yellow oil or colorless solid.

B) Synthesis of Carbamates:

To a suspension of the appropriate base (1 mmol) and reagent (1 mmole) in abs. dichloromethane (15 ml), DBU (1.15 mmol) is added and the mixture is stirred for 2 to 7 days, the reaction is monitored by TLC (silica, dichloromethane-methanol 10:1 mixture as an eluent). The reaction mixture is extracted twice by 10% sodium hydrogencarbonate solution, once by water, and the organic layer is dried over sodium sulfate. After evaporation the residue is treated with diethyl ether, the obtained solid is filtered off, washed with a small amount of acetonitrile and finally with diethyl ether. The crude product (51-81%) can be recrystallized from acetonitrile to yield the purified product (34-73%).

C) In case the apppropriate chloroformiates are commercially available 1 mmol of the chloroformiate is reacted with 1 mmol of the amino building block in pyridine. After the reaction is completed, the solvent is removed and the remaining crude product purified as described above.

F. General Procedure for the Formation of Urea 1 equivalent of the amine and 1 equivalent of the appropriate isocyanate are stirred in dichloromethane over night at ambient temperature. The mixture is concentrated and the residue is subjected to flash chromatography on silica gel (eluent dichloromethane/methanol) and/or recristalyzed from ethanol.

Alternatively, 1 equivalent of the amine, 1 equivalent of N,N-carbonyidimidazole and 1 equivalent of the second amine are stirred in a suitable solvent, e.g. dichloromethane, over night at ambient temperature. The mixture is concentrated and the residue is subjected to flash chromatography on silica gel and/or recristalyzed from ethanol.

G. General Procedure for Thiocarbamate Formation 1 equivalent of the amine and 1.3 equivalents of the appropriate chlorothioformate are stirred in pyridine for 3 h at ambient temperature. The mixture is concentrated and the thiocarbamate is crystallized from ethanol and/or purified by flash chromatography on silica gel.

G1. Alternative General Procedure for Thiocarbamate Formation a) Preparation of the imidazole 1-carboxylic thioester reagents: A solution of the appropriate thiol (10 mmol), 1,1'-carbonyldiimidazole (10 mmol) in abs. tetrahydrofurane (20 ml) is stirred at room temperature for 2 to 3 h, the reaction is monitored by TLC. The reaction mixture is extracted by three portions of 10% sodium hydrogencarbonate solution and once by water. The organic layer is dried over sodium sulfate, evaporated to yield a pale yellow oil or colorless solid.

b) Synthesis of thiocarbamates: To a suspension of the appropriate base (1 mmol) and reagent (1 mmole) in abs. dichloromethane (20 ml), DBU (1.2 mmol) is added, the mixture is stirred for 1 to 2 days, the reaction is monitored by TLC (silica, dichloromethane/ethyl acetate 10:1 mixture as an eluent, or, in some cases, ethyl acetate/methanol 1:1). The reaction mixture is extracted twice by 10% sodium hydrogencarbonate solution, once by water, and the organic layer is dried over sodium sulfate. After evaporation the residue is purified by column chromatography.

It is to be stated, that, starting from the starting compounds, which are mentioned herein or which can be prepared analogously to the herein-mentioned compounds, the person skilled in the art can apply—on the base of his/her expert knowledge, general art and/or analogous or similar art-known procedures—the general procedures described herein to the synthesis of those specific examples given herein and further specific examples encompassed from the scope of the present invention.

Commercial Applicability

The compounds according to the present invention have miscellaneous valuable pharmacological properties which can make them commercially applicable.

The compounds according to the invention therefore can be employed as therapeutic agents for the treatment and prophylaxis of diseases in human and veterinary medicine.

Thus, for example, in more embodimental detail, the compounds according to this invention are potent and highly efficacious cell-cycle specific inhibitors of cellular (hyper) proliferation and/or inducers of apoptosis in cancer cells. Therefore, these compounds are expected to be useful for treating (hyper)proliferative diseases and/or disorders responsive to the induction of apoptosis, in particular cancer.

Further on, these compounds can be useful in the treatment of benign or malignant neoplasia. A "neoplasia" is defined by cells displaying aberrant cell proliferation and/or survival and/or a block in differentiation. A "benign neoplasia" is described by hyperproliferation of cells, incapable of forming an aggressive, metastasizing tumor in-vivo. In contrast, a "malignant neoplasia" is described by cells with multiple cellular and biochemical abnormalities, capable of forming a systemic disease, for example forming tumor metastasis in distant organs.

Various diseases are caused by limitless replicative potential and aberrant cell proliferation ("hyperproliferation") as well as evasion from apoptosis. These diseases include e.g. benign hypoplasia like that of the prostate ("BPH") or colon epithelium, psoriasias, glomerulonephritis or osteoarthritis. Most importantly these diseases include malignant neoplasias commonly described as cancer and characterized by tumor cells finally metastasizing into distinct organs or tissues. Malignant neoplasia include solid and hematological tumors. Solid tumors are exemplified by tumors of the breast, bladder, bone, brain, central and peripheral nervus system, colon, endocrine glands (eg thyroid and adrenal cortex), esophagus, endometrium, germ cells, head and neck, kidney, liver, lung, larynx and hypopharynx, mesothelioma, sarcoma, ovary, pancreas, prostate, rectum, renal, small intestine, soft tissue, testis, stomach, skin, ureter, vagina and vulva. Malignant neoplasias include inherited cancers exemplified by Retinomblastoma and Wilms tumor. In addition, malignant neoplasia include primary tumors in said organs and corresponding secondary tumors in distant organs ("tumor metastases"). Hematological tumors are exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, cancers of unknown primary site as well as AIDS related malignancies.

It is to be noted that a cancer disease as well as a malignant neoplasia does not necessarily require the formation of metastases in distant organs. Certain tumors exert devastating effects on the primary organ itself through their aggressive growth properties. These can lead to the destruction of the tissue and organ structure finally resulting in failure of the assigned organ function.

Compounds of formula I according to the present invention will commercially applicable for treatment, prevention or amelioration of the diseases of benign and malignant behavior as described before.

Neoplastic cell proliferation might effect normal cell behaviour and organ function. For example the formation of new blood vessels, a process described as neovascularization, is induced by tumors or tumor metastases. Compounds of formula I according to this invention will commercially applicable for treatment of pathophysiological relevant processes caused by benign or neoplastic cell proliferation, such as but not limited to neovascularization by unphysiological proliferation of vascular endothelial cells.

Drug resistance is of particular importance for the frequent failure of standard cancer therapeutics. This drug resistance is caused by various cellular and molelcular mechanisms like overexpression of drug efflux pumps or mutation within the cellular target protein. The commercial applicability of the compounds of formula I according to this invention is not limited to $1^{st}$ line treatment of patients. Patients with resistance to defined cancer chemotherapeutics or target specific anti-cancer drugs ($2^{nd}$ or $3^{rd}$ line treatment) are also amenable for treatment with the compounds of formula I according to this invention.

The compounds according to the present invention display a cell cycle dependent cytotoxic activity, more precisely a mitosis confined activity, leading to a mitotic arrest which inevitably results in the onset of apoptosis and/or cell death.

In the context of their properties, functions and usabilities mentioned herein, the compounds according to the present invention are expected to be distinguished by valuable and desirable effects related therewith, such as e.g. by low toxicity, superior bioavailability in general (such as e.g. good enteral absorption), superior therapeutic window, absence of significant side effects, and/or further beneficial effects related with their therapeutic and pharmaceutical suitability.

The invention further includes a method for treating (hyper)proliferative diseases and/or disorders responsive to the induction of apoptosis, particularly those diseases, disorders, conditions or illnesses mentioned above, in mammals, including humans, suffering therefrom comprising administering to said mammals in need thereof a pharmacologically active and therapeutically effective and tolerable amount of one or more of the compounds of formula I according to this invention.

The present invention further includes a method useful to modulate apoptosis and/or aberrant cell growth in the therapy of benign or malignant neoplastic diseases, such as e.g. cancer, comprising administering to a subject in need of such therapy a therapeutically active and pharmacologically effective and tolerable amount of one or more of the compounds of formula I according to this invention which function by arresting aberrant cell growth and/or inducing apoptosis.

The present invention further relates to the use of the compounds of formula I according to this invention for the production of pharmaceutical compositions which are employed for the treatment, prophylaxis and/or amelioration of the illnesses mentioned.

The present invention further relates to the use of the compounds of formula I according to this invention for the production of pharmaceutical compositions which can be used in the treatment, prevention or amelioration of (hyper)proliferative diseases of benign or malignant behaviour and/or disorders responsive to the induction of apoptosis in a mammal, such as, for example, benign or malignant neoplasia, particularly cancer.

The present invention further relates to the use of the compounds of formula I according to this invention for the production of pharmaceutical compositions which can be used use in the treatment, prevention or amelioration of disorders responsive to arresting of aberrant cell growth and/or induction of apoptosis.

The present invention further relates to pharmaceutical compositions comprising one or more of the compounds of formula I according this invention and a pharmaceutically acceptable carrier or diluent.

The present invention further relates to pharmaceutical compositions made by combining one or more of the compounds according to this invention and a pharmaceutically acceptable carrier or diluent.

The present invention further relates to combinations comprising one or more of the compounds of formula I according to this invention and pharmaceutically acceptable auxiliaries, excipients or vehicles, e.g. for use in the treatment, prevention or amelioration of (hyper)proliferative diseases of benign or malignant behaviour and/or disorders responsive to the induction of apoptosis in a mammal, such as e.g. cancer.

The present invention further relates to a composition consisting essentially of a therapeutically effective and tolerable amount of one or more tetrahydropyridothiophene compounds of formula I according to this invention together with the usual pharmaceutically acceptable vehicles, diluents and/or excipients for use in therapy, e.g. for treating, preventing or ameliorating (hyper)proliferative diseases, such as e.g. cancer, and/or disorders responsive to induction of apoptosis.

The present invention further relates to compounds of formula I according to this invention for use in therapy, such as, for example, in the treatment, prevention or amelioration of (hyper)proliferative diseases of benign or malignant behaviour and/or disorders responsive to the induction of apoptosis, such as e.g. those diseases mentioned herein, particularly cancer.

The present invention further relates to compounds of formula I according to this invention having anti-proliferative and/or apoptosis inducing activity.

The present invention further relates to pharmaceutical compositions according to this invention having anti-proliferative activity.

The present invention further relates to pharmaceutical compositions according to this invention having apoptosis inducing activity.

The invention further relates to the use of a pharmaceutical composition comprising one or more of the compounds of formula I according to this invention as sole active ingredient(s) and a pharmaceutically acceptable carrier or diluent in the manufacture of pharmaceutical products for the treatment and/or prophylaxis of the illnesses mentioned above.

The pharmaceutical compositions according to this invention are prepared by processes which are known per se and familiar to the person skilled in the art. As pharmaceutical compositions, the compounds of the invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries, vehicles, excipients, diluents, carriers or adjuvants which are suitable for the desired pharmaceutical formulations, preparations or compositions on account of his/her expert knowledge. In addition to solvents, gel formers, ointment bases and other active compound excipients, for example antioxidants, dispersants, emulsifiers, pre-servatives, solubilizers, colorants, complexing agents or permeation promoters, can be used.

Additionally, the invention relates to an article of manufacture, which comprises packaging material and a pharmaceutical agent contained within said packaging material, wherein the pharmaceutical agent is therapeutically effective inhibiting cellular (hyper)proliferation and/or inducing apoptosis, ameliorating the symptoms of a (hyper)proliferative disorder and/or a disease responsive to the induction of apoptosis, and wherein the packaging material comprises a label or package insert which indicates that the pharmaceutical agent is useful for preventing or treating a (hyper)proliferative disorder and/or a diseases responsive to the induction of apoptosis, and wherein said pharmaceutical agent comprises one or more compounds according to the invention. The packaging material, label and package insert otherwise parallel or resemble what is generally regarded as standard packaging material, labels and package inserts for pharmaceuticals having related utilities.

Depending upon the particular disease, to be treated or prevented, additional therapeutic active agents, which are normally administered to treat or prevent that disease, may optionally be coadministered with the compounds of formula I according to this invention. As used herein, additional therapeutic agents that are normally administered to treat or prevent a particular disease are known as appropriate for the disease being treated.

For example, compounds according to this invention may be combined with one or more standard therapeutic agents used for treatment of the diseases as mentioned before. For further example, the compounds of formula I according to this invention may be combined with one or more known anti-cancer agents, such as e.g. chemotherapeutic and/or target specific anti-cancer agents as described below.

Examples of known chemotherapeutic anti-cancer agents frequently used for combination therapy include, but not are limited to (i) alkylating/carbamylating agents such as Cyclophosphamid (Endoxan®), Ifosfamid (Holoxan®), Thiotepa (Thiothepa Lederle®), Melphalan (Alkeran®), or chloroethyinitrosourea (BCNU); (ii) platinum derivatives like cisplatin (Platinex® BMS), oxaliplatin or carboplatin (Carboplat® BMS); (iii) antimitotic agents/tubulin inhibitors such as vinca alkaloids (vincristine, vinblastine, vinorelbine), taxanes such as Taxol (Paclitaxel®), Taxotere (Docetaxel®) and analogs as well as new formulations and conjugates thereof; (iv) topoisomerase inhibitors such as anthracyclines such as Doxorubicin (Adriblastin®), epipodophyllotoxines (such as Etoposide (Etopophos®) and camptothecin analogs such as Topotecan (Hycamtin®); (v) pyrimidine antagonists such as 5-fluorouracil (5-FU), Capecitabine (Xeloda®), Arabinosylcytosine/Cytarabin (Alexan®) or Gemcitabine (Gemzar®); (vi) purin antagonists such as 6-mercaptopurine (Puri-Nethol®), 6-thioguanine or fludarabine (Fludara®) and finally (vii) folic acid antagonists such as methotrexate (Farmitrexat®) and pemetrexed (Alimta®).

Examples of target specific anti-cancer agent classes used in experimental or standard cancer therapy include but are not limited to (i) kinase inhibitors such as e.g. Glivec (Imatinib®), ZD-1839/Iressa (Gefitinib®), Bay43-9006 (Sorafenib®), SU11248 (Sutent®) or OSI-774/Tarceva (Erlotinib®); (ii) proteasome inhibitors such as PS-341 (Velcade®); (iii) histone deacetylase inhibitors like SAHA, PXD101, MGCD0103, Depsipeptide/FK228, NVP-LBH589, Valproic acid (VPA) and butyrates; (iv) heat shock protein inhibitors like 17-allylaminogeldanamycin (17-AAG); (v) vascular targeting agents (VAT) like combretastatin A4 phosphate and anti-angiogenic drugs like the VEGF antibody Avastin (Bevacizumab®) or the KDR tyrosine kinase inhibitor PTK787/ZK222584 (Vatalanib®); (vi) monodonal antibodies such as Herceptin (Trastuzumab®) or MabThera/Rituxan (Rituximab®) or C225/Erbitux (Cetuximab®) as well as mutants and conjugates of monoclonal antibodies and antibody fragments; (vii) oligonucleotide based therapeutics like G-3139/Genasense (Oblimersen®); (viii) protease inhibitors (ix) hormonal therapeutics such as anti-estrogens (e.g. Tamoxifen), anti-androgens (e.g. Flutamide or Casodex), LHRH analogs (e.g. Leuprolide, Goserelin or Triptorelin) and aromatase inhibitors.

Other known anti-cancer agents which can be used for combination therapy include bleomycin, retinoids such as all-trans retinoic acid (ATRA), DNA methyltransferase inhibitors such as the 2-deoxycytidine derivative Decitabine (Docagen®), alanosine, cytokines such as interleukin-2 or interferons such as interferon α2 or interferon-γ, TRAIL, DR4/5 agonistic antibodies, FasL- and TNF-R agonists.

As exemplary anti-cancer agents for use in the combination therapy according to the present invention the following drugs may be mentioned, without being restricted thereto, 5 FU, actinomycin D, ABARELIX, ABCIXIMAB, ACLARUBICIN, ADAPALENE, ALEMTUZUMAB, ALTRETAMINE, AMINOGLUTETHIMIDE, AMIPRILOSE, AMRUBICIN, ANASTROZOLE, ANCITABINE, ARTEMISININ, AZATHIOPRINE, BASILIXIMAB, BENDAMUSTINE, BEXXAR, BICALUTAMIDE, BLEOMYCIN, BROXURIDINE, BUSULFAN, CAPECITABINE, CARBOPLATIN, CARBOQUONE, CARMUSTINE, CETRORELIX, CHLORAMBUCIL, CHLORMETHINE, CISPLATIN, CLADRIBINE, CLOMIFENE, CYCLOPHOSPHAMIDE, DACARBAZINE, DACLIZUMAB, DACTINOMYCIN, DAUNORUBICIN, DESLORELIN, DEXRAZOXANE, DOCETAXEL, DOXIFLURIDINE, DOXORUBICIN, DROLOXIFENE, DROSTANOLONE, EDELFOSINE, EFLORNITHINE, EMITEFUR, EPIRUBICIN, EPITIOSTANOL, EPTAPLATIN, ERBITUX, ESTRAMUSTINE, ETOPOSIDE, EXEMESTANE, FADROZOLE, FINASTERIDE, FLOXURIDINE, FLUCYTOSINE, FLUDARABINE, FLUOROURACIL, FLUTAMIDE, FORMESTANE, FOSCARNET, FOSFESTROL, FOTEMUSTINE, FULVESTRANT, GEFITINIB, GEMCITABINE, GLIVEC, GOSERELIN, GUSPERIMUS, HERCEPTIN, IDARUBICIN, IDOXURIDINE, IFOSFAMIDE, IMATINIB, IMPROSULFAN, INFLIXIMAB, IRINOTECAN, LANREOTIDE, LETROZOLE, LEUPRORELIN, LOBAPLATIN, LOMUSTINE, MELPHALAN, MERCAPTOPURINE, METHOTREXATE, METUREDEPA, MIBOPLATIN, MIFEPRISTONE, MILTEFOSINE, MIRIMOSTIM, MITOGUAZONE, MITOLACTOL, MITOMYCIN, MITOXANTRONE, MIZORIBINE, MOTEXAFIN, NARTOGRASTIM, NEBAZUMAB, NEDAPLATIN, NILUTAMIDE, NIMUSTINE, OCTREOTIDE, ORMELOXIFENE, OXALIPLATIN, PACLITAXEL, PALIVIZUMAB, PEGASPARGASE, PEGFILGRASTIM, PENTETREOTIDE, PENTOSTATIN, PERFOSFAMIDE, PIPOSULFAN, PIRARUBICIN, PLICAMYCIN, PREDNIMUSTINE, PROCARBAZINE, PROPAGERMANIUM, PROSPIDIUM CHLORIDE, RALTITREXED, RANIMUSTINE, RANPIRNASE, RASBURICASE, RAZOXANE, RITUXIMAB, RIFAMPICIN, RITROSULFAN, ROMURTIDE, RUBOXISTAURIN, SARGRAMOSTIM, SATRAPLATIN, SIROLIMUS, SOBUZOXANE, SPIROMUSTINE, STREPTOZOCIN, TAMOXIFEN, TASONERMIN, TEGAFUR, TEMOPORFIN, TEMOZOLOMIDE, TENIPOSIDE, TESTOLACTONE, THIOTEPA, THYMALFASIN, TIAMIPRINE, TOPOTECAN, TOREMIFENE, TRASTUZUMAB, TREOSULFAN, TRIAZIQUONE, TRIMETREXATE, TRIPTORELIN, TROFOSFAMIDE, UREDEPA, VALRUBICIN, VERTEPORFIN, VINBLASTINE, VINCRISTINE, VINDESINE, VINORELBINE, VOROZOLE and ZEVALIN.

The person skilled in the art is aware on the base of his/her expert knowledge of the total daily dosage(s) and administration form(s) of the additional therapeutic agent(s) coadministered. Said total daily dosage(s) can vary within a wide range.

In practicing the present invention, the compounds of formula I according to this invention may be administered in combination therapy separately, sequentially, simultaneously or chronologically staggered (such as e.g. as combined unit dosage forms, as separate unit dosage forms, as adjacent discrete unit dosage forms, as fixed or non-fixed combinations, as kit-of-parts or as admixtures) with one or more known anti-cancer agents or target specific anti-cancer agents, such as e.g. those mentioned above.

In this context, the present invention further relates to a combination comprising a first active ingredient, which is at least one tetrahydropyridothiophene compound of formula I according to this invention, and a second active ingredient, which is at least one anti-cancer agent or target specific anti-cancer agent, such as e.g. one or more of those mentioned herein above, for separate, sequential, simultaneous or chronologically staggered use in therapy, such as e.g. to treat, prevent or ameliorate hyperproliferative diseases of benign or malignant behaviour and/or disorders responsive to the induction of apoptosis in a mammal, such as e.g. those diseases mentioned herein, for example cancer.

The term "combination" according to this invention may be present as a fixed combination, a non-fixed combination or a kit-of-parts.

A "fixed combination" is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A "kit-of-parts" is defined as a combination wherein the said first active ingredient and the said second active ingredient are present in more than one unit. One example of a "kit-of-parts" is a combination wherein the said first active ingredient and the said second active ingredient are present separately. The components of the kit-of-parts may be administered separately, sequentially, simultaneously or chronologically staggered.

The present invention further relates to a pharmaceutical composition comprising a first active ingredient, which is at least one tetrahydropyridothiophene compound of formula I according to this invention, and a second active ingredient, which is at least one anti-cancer agent or target specific anti-cancer agent, such as e.g. one or more of those mentioned herein above, and, optionally, a pharmaceutically acceptable carrier or diluent, for separate, sequential, simultaneous or chronologically staggered use in therapy.

The present invention further relates to a combination product comprising a.) at least one compound according to this invention formulated with a pharmaceutically acceptable carrier or diluent, and b.) at least one art-known anti-cancer agent, such as e.g. one or more of those mentioned herein above, formulated with a pharmaceutically acceptable carrier or diluent.

The present invention further relates to a kit-of-parts comprising a preparation of a first active ingredient, which is a tetrahydropyridothiophene compound of formula I according to this invention, and a pharmaceutically acceptable carrier or diluent; a preparation of a second active ingredient, which is an art-known anti-cancer and/or target specific anti-cancer agent, such as one of those mentioned above, and a pharmaceutically acceptable carrier or diluent; for simultaneous, sequential, separate or chronologically staggered use in therapy. Optionally, said kit comprises instructions for its use in therapy, e.g. to treat hyperproliferative diseases and/or disorders responsive to the induction of apoptosis, such as e.g. cancer.

The present invention further relates to a combined preparation comprising at least one compound of formula I according to the present invention and at least one chemotherapeutic anti-cancer and/or target specific anti-cancer agent for simultaneous, sequential or separate administration.

In this connection, the present invention further relates to pharmaceutical combinations or compositions according to this invention having anti-proliferative and/or apoptosis inducing activity.

In addition, the present invention further relates to a method for treating in combination therapy hyperproliferative diseases and/or disorders responsive to the induction of apoptosis, such as e.g. cancer, in a patient comprising administering a combination, composition, formulation, preparation or kit as described herein to said patient in need thereof.

In addition, the present invention further relates to a method for treating hyperproliferative diseases of benign or malignant behaviour and/or disorders responsive to the induction of apoptosis, such as e.g. cancer, in a patient comprising administering in combination therapy separately, simultaneously, sequentially or chronologically staggered a pharmaceutically active and therapeutically effective and tolerable amount of a pharmaceutical composition, which comprises a tetrahydropyridothiophene compound of formula I according to this invention and a pharmaceutically acceptable carrier or diluent, and a pharmaceutically active and therapeutically effective and tolerable amount of one or more chemotherapeutic anti-cancer and/or target specific anti-cancer agents, such as e.g. one or more of those mentioned herein, to said patient in need thereof.

In addition, the present invention further relates to the use of a composition, combination, formulation, preparation or kit in the manufacture of a pharmaceutical product, such as e.g. a commercial package or a medicament, for treating, preventing or ameliorating hyperproliferative diseases, such as e.g. cancer, and/or disorders responsive to the induction of apoptosis, particularly those diseases mentioned herein, such as e.g. malignant or benign neoplasia.

The present invention further relates to a commercial package comprising one or more compounds of formula I of the present invention together with instructions for simultaneous, sequential or separate use with one or more chemotherapeutic and/or target specific anti-cancer agents, such as e.g. any of those mentioned herein.

The present invention further relates to a commercial package consisting essentially of one or more compounds of formula I of the present invention as sole active ingredient together with instructions for simultaneous, sequential or separate use with one or more chemotherapeutic and/or target specific anti-cancer agents, such as e.g. any of those mentioned herein.

The present invention further relates to a commercial package comprising one or more chemotherapeutic and/or target specific anti-cancer agents, such as e.g. any of those mentioned herein, together with instructions for simultaneous, sequential or separate use with one or more tetrahydropyridothiophene compounds of formula I according to the present invention.

The compositions, combinations, preparations, formulations, kits or packages mentioned in the context of the combination therapy according to this invention may also include more than one of the compounds according of formula I to this invention and/or more than one of the art-known anti-cancer agents mentioned.

The first and second active ingredient of a combination or kit-of-parts according to this invention may be provided as separate formulations (i.e. independently of one another), which are subsequently brought together for simultaneous, sequential, separate or chronologically staggered use in combination therapy; or packaged and presented together as separate components of a combination pack for simultaneous, sequential, separate or chronologically staggered use in combination therapy.

The type of pharmaceutical formulation of the first and second active ingredient of a combination or kit-of-parts according to this invention can be similar, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to this invention may together comprise a therapeutically effective amount for the treatment, prophylaxis or amelioration of a (hyper)proliferative diseases and/or a disorder responsive to the induction of apoptosis, particularly one of those diseases mentioned herein.

In addition, compounds of formula I according to the present invention can be used in the pre- or post-surgical treatment of cancer.

In further addition, compounds of formula I of the present invention can be used in combination with radiation therapy.

A combination according to this invention can refer to a composition comprising both the compounds of formula I according to this invention and the other active anti-cancer agent in a fixed combination (fixed unit dosage form), or a medicament pack comprising the two active ingredients as discrete separate dosage forms (non-fixed combination). In case of a medicament pack comprising the two active ingredients, the active ingredients are preferably packed into blister cards which are suited for improving compliance.

Each blister card preferably contains the medicaments to be taken on one day of treatment. If the medicaments are to be taken at different times of day, the medicaments can be disposed in different sections on the blister card according to the different ranges of times of day at which the medicaments are to be taken (for example morning and evening or morning, midday and evening). The blister cavities for the medicaments to be taken together at a particular time of day are accommodated in the respective range of times of day. The various times of day are, of course, also put on the blister in a clearly visible way. It is also possible, of course, for example to indicate a period in which the medicaments are to be taken, for example stating the times.

The daily sections may represent one line of the blister card, and the times of day are then identified in chronological sequence in this column.

Medicaments which must be taken together at a particular time of day are placed together at the appropriate time on the blister card, preferably a narrow distance apart, allowing them to be pushed out of the blister easily, and having the effect that removal of the dosage form from the blister is not forgotten.

The administration of the pharmaceutical compositions or combinations according to the invention may be performed in any of the generally accepted modes of administration available in the art. Illustrative examples of suitable modes of administration include intravenous, oral, nasal, parenteral, topical, transdermal and rectal delivery. Oral and intravenous delivery are preferred.

For the treatment of dermatoses, the compounds of the invention are in particular administered in the form of those pharmaceutical compositions which are suitable for topical application. For the production of the pharmaceutical compositions, the compounds of the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention are prepared by processes known per se. The dosage of the active compounds is carried out in the order of magnitude customary for inhibitors of cellular proliferation or apoptosis inducers. Topical application forms (such as ointments) for the treatment of dermatoses thus contain the active compounds in a concentration of, for example, 0.1-99%. The customary dose in the case of systemic therapy (p.o.) is between 0.3 and 30 mg/kg per day, (i. v.) is between 0.3 and 30 mg/kg/h.

The choice of the optimal dosage regime and duration of medication, particularly the optimal dose and manner of administration of the active compounds necessary in each case can be determined by a person skilled in the art on the basis of his/her expert knowledge.

Biological Investigations

The anti-proliferative/cytotoxic activity of the compounds described herein, can be tested on subdlones of RKO (RKOp27) human colon adenocarcinoma cells (Schmidt et al., Oncogene 19, 2423-2429; 2000) using the Alamar Blue cell viability assay (described in O'Brien et al. Eur J Biochem 267, 5421-5426, 2000). The compounds are dissolved as 20 mM solutions in dimethylsulfoxide (DMSO) and subsequently diluted in semi-logarithmic steps. DMSO dilutions are further diluted 1:100 into Dulbecco's modified Eagle's medium (DMEM) containing 10% fetal calf serum to a final concentration twice as much as the final concentration in the test. RKO subclones are seeded into 96 well flat bottom plates at a density of 4000 cells per well in a volume of 50 pi per well. 24 hours after seeding the 50 µl each of the compound dilutions in DMEM medium are added into each well of the 96 Well plate. Each compound dilution is tested as quadruplicates. Wells containing untreated control cells are filled with 50 µl DMEM medium containing 1% DMSO. The cells are then incubated with the substances for 72 hours at 37° C. in a humidified atmosphere containing 5% carbon dioxide. To determine the viability of the cells, 10 µl of an Alamar Blue solution (Biosource) are added and the fluorescence is measured at an extinction of 544 nm and an emission of 590 nm. For the calculation of the cell viability the emission value from untreated cells is set as 100% viability and the emission rates of treated cells are set in relation to the values of untreated cells. Viabilities are expressed as % values.

The corresponding $IC_{50}$ values of the compounds for anti-proliferative/cytotoxic activity are determined from the concentration-effect curves.

Representative $IC_{50}$ values for anti-proliferation/cytotoxicity determined for the compounds mentioned and numbered as Examples in the examples above follow from the following table A ($1^{st}$ column), in which the numbers of the compound correspond to the numbers of the examples. Any or all of the compounds according to the present invention which are listed in the Table A, as well as their salts, are to be mentioned as a particular interesting subject of the present invention.

TABLE A

Anti-proliferative/cytotoxic activity

| Compound | $IC_{50}$ RKO p27 uninduced [µM] | $IC_{50}$ RKO p27 induced [µM] |
|---|---|---|
| 1 | The IC50 values of these listed compounds are all ≤2 | >100 |
| 3 | | >100 |
| 4 | | 100 |
| 5 | | 80 |
| 6 | | >100 |
| 7 | | >100 |
| 8 | | >100 |
| 12 | | >100 |
| 13 | | >100 |
| 14 | The IC50 values of these listed compounds are all ≤2 | >100 |
| 17 | | >100 |
| 18 | | >100 |
| 19 | | >100 |
| 22 | | >100 |
| 24 | | >100 |
| 25 | | >100 |
| 26 | | >100 |
| 27 | | >100 |
| 28 | | >100 |
| 29 | | >100 |
| 20 | 3 | >100 |
| 30 to 42, 44 to 77, and 79 to 82 | The IC50 values of these listed compounds are all ≤3 | The IC50 values of these listed compounds are all >60 |
| 83 to 88, 93 to 95, 97 to 103 | The IC50 values of these listed compounds are all ≤3 | The IC50 values of these listed compounds are all >100 |

To determine the cell cycle specific mode of action, subdlones of RKO colon adenocarcinoma cells (RKOp27 or RKOp21 as described by Schmidt et al. in Oncogene 19, 2423-2429; 2000) are seeded into 96 well flat bottom plates at a density of 16000 cells per well in a volume of 50 µl per well in DMEM growth medium with 10% FCS containing 10 µM Ponasterone A. 24 hours after seeding the 50 µl each of the compound dilutions in DMEM medium are added into each well of the 96 Well plate. Each compound dilution is tested as quadruplicates. Wells containing untreated control cells are filled with 50 µl DMEM medium containing 1% DMSO. The cells are then incubated with the substances for 72 hours at 37° C. in a humidified atmosphere containing 5% carbon dioxide. To determine the viability of the cells, 10 µl of an Alamar Blue solution (Biosource) are added and the fluorescence was measured at an extinction of 544 nm and an emission of 590 nm. For the calculation of the cell viability the emission value from untreated cells is set as 100% viability and the emission rates of treated cells are set in relation to the values of untreated cells. Viabilities are expressed as % values. Viability is compared of proliferating cells grown in the absence of the inducer Ponasterone A, versus viability of cells arrested by the expression of ectopic p27Kip1 induced by Ponasterone A. The data of this experimental setting are summarized in table A ($2^{nd}$ column).

To test the anti-proliferative activity/cytotoxicity on cells known to be highly resistant towards distinct classes of chemotherapeutics, HCT15 cells (with P-glycoprotein overexpression) and MCF7 ADR cells, both of them are known to overexpress certain classes of multidrug resistance transporters are used in Alamar Blue assays as described above. Briefly, the compounds are dissolved as 20 mM solutions in dimethylsulfoxide (DMSO) and subsequently diluted in semi-logarithmic steps. DMSO dilutions were further diluted 1:100 into Dulbecco's modified Eagle's medium (DMEM) containing 10% fetal calf serum to a final concentration twice as much as the final concentration in the test. The cells to be tested are seeded into 96 well flat bottom plates at a density of 10000 cells per well in a volume of 50 µl per well. 24 hours after seeding the 50 µl each of the compound dilutions in DMEM medium are added into each well of the 96 Well plate. Each compound dilution is tested as quadruplicates. Wells containing untreated control cells are filled with 50 µl DMEM medium containing 1% DMSO. The cells are then incubated with the substances for 72 hours at 37° C. in a humidified atmosphere containing 5% carbon dioxide. To determine the viability of the cells, 10 µl of an Alamar Blue solution (Biosource) are added and the fluorescence was measured at an extinction of 544 nm and an emission of 590 nm. For the calculation of the cell viability the emission value from untreated cells is set as 100% viability and the emission rates of treated cells are set in relation to the values of untreated cells. Viabilities are expressed as % values.

The induction of apoptosis can be measured by using a Cell death detection ELISA (Roche Biochemicals, Mannheim, Germany). RKO subclones are seeded into 96 well flat bottom plates at a density of 10000 cells per well in a volume of 50 µl per well. 24 hours after seeding the 50 µl each of the compound dilutions in DMEM medium are added into each well of the 96 Well plate. Each compound dilution is tested at least as triplicates. Wells containing untreated control cells are filled with 50 µl DMEM medium containing 1% DMSO. The cells are then incubated with the substances for 24 hours at 37° C. in a humidified atmosphere containing 5% carbon dioxide. As a positive control for the induction of apoptosis, cells are treated with 50 µM Cisplatin (Gry Pharmaceuticals, Kirchzarten, Germany). Medium is then removed and the cells are lysed in 200 µl lysis buffer. After centrifugation as described by the manufacturer, 10 µl of cell lysate is processed as described in the protocol. The degree of apoptosis is calculated as follows: The absorbance at 405 nm obtained with lysates from cells treated with 50 µM cisplatin is set as 100 cpu (cisplatin units), while an absorbance at 405 nm of 0.0 was set as 0.0 cpu. The degree of apoptosis is expressed as cpu in relation to the value of 100 cpu reached with the lysates obtained from cells treated with 50 µM cisplatin.

The mitotis-confined activity can be measured using a methylen blue/eosin staining kit (Merck, Darmstadt, Germany). RKO subclones are seeded into 6 well issue culture plates at a density of 200000 cells per well in a volume of 2 ml per well. 24 hours after seeding each of the compound dilutions in DMEM containing up to 1% DMSO are added onto each 6 well plate. The cells are then incubated with the substances for 24 hours at 37° C. in a humidified atmosphere containing 5% carbon dioxide. As a positive control for the induction of mitosis, the cells are treated with 20 nM vincristine or paclitaxel. The cells are then harvested by trypsinization and subsequent centrifugation, and washed once with phosphate-buffered saline. Subsequently, the cells are centrifuged on microscope slides for 1 min at 1200 rpm using a cytospin. Cells are then fixed with methanol and stained with methylen blue and eosin according to the manufacturer's recommendations. Mitotic figures can then be visualized by standard microscopy.

Another method to determine the mitosis confined activity can be immunoblotting of cell extracts with an antibody specific for phosphorylated histone H3, which is a generally accepted marker of mitosis. RKO subclones are seeded into 6 well tissue culture plates at a density of 200000 cells per well in a volume of 2 ml per well. 24 hours after seeding each of the compound dilutions in DMEM containing up to 1% DMSO are added onto each 6 well plate. The cells are then incubated with the substances for another 24 hours at 37° C. in a humidified atmosphere containing 5% carbon dioxide. As a positive control for the induction of mitosis, the cells are treated with 20 nM vincristine or paclitaxel. The cells are then harvested by trypsinization and subsequent centrifugation, and washed once with phosphate-buffered saline. Subsequently, the cells are lysed in a lysis buffer containing 50 mM Tris, pH 7.4, 150 mM NaCl, 1% NP40, 50 mM NaF, 1 mM $Na_3VO_4$, 1 mM phenylmethylsulfonyl fluoride. The lysates are cleared by centrifugation and the supernatants are collected. Equal amounts of lysate protein are separated in an SDS-polyacrylamide electrophoresis using 12.5% gels and subsequently blotted on immobilon membranes (Millipore, schwalbach, Germany). After blocking unspecific binding sites by incubation of the membrane in 3% bovine serum albumine in tris-puffered saline containing 0.05% tween 20, antibodies specific for phospho-histone H3 (Cell Signaling Technology, Beverley, USA) were added for 1 hour. After intensive washing with tris-puffered saline containing 0.05% tween 20, specific signals were visualized using a horseradish-peroxidase-coupled secondary antibody and the use of the ECL chemoluminescence detection kit (Amersham, Braunschweig, Germany) according to the manufacturer's recommendations.

The invention claimed is:

1. A compound of formula I

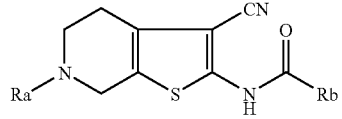

(I)

wherein
Ra is —C(O)R1, —C(O)OR2, —C(O)SR2, —C(O)N(R3)R4, —S(O)$_2$R1, or —S(O)$_2$N(R3)R4;

Rb is optionally substituted by Rba and/or Rbb and/or Rbc, and is aryl,
aryl is phenyl, or naphthyl;
R1, R2 and R3 may be the same or different and are independently selected from the group consisting of: hydrogen, 1-7C-alkyl, 3-7C-cycloalkyl, Ar, Har and Het, wherein each of said 1-7C-alkyl, 3-7C-cycloalkyl, Ar, Har and Het can be unsubstituted or substituted by at least one substituent independently selected from R5;
each R4 is independently selected from the group consisting of: hydrogen, 1-7C-alkyl, and 3-7C-cycloalkyl, wherein each of said 1-7C-alkyl and 3-7C-cycloalkyl can be unsubstituted or substituted by at least one substituent independently selected from R5;
R5, Rba, Rbb and Rbc may be the same or different and are independently selected from the group consisting of: 1-7C-alkyl, 3-7C-cycloalkyl, Ar, Har, Het, halogen, trifluoromethyl, nitro, cyano, guanidino, amidino, —C(O)R6, —C(O)OR7, —C(O)N(R8)R9, —S(O)$_2$R6, —S(O)$_2$N(R8)R9, —N(R10)C(O)R6, —N(R10)C(O)OR7, —N(R10)C(O)N(R8)R9, —N(R10)S(O)$_2$R6, —N(R10)S(O)$_2$N(R8)R9, —OC(O)R6, —OC(O)N(R8)R9, —OR7, —N(R8)R(9), and —SR7, wherein each of said 1-7C-alkyl, 3-7C-cycloalkyl, Ar, Har and Het can be unsubstituted or substituted by at least one substituent independently selected from R11;
R6, R7 and R8 may be the same or different and are independently selected from the group consisting of: hydrogen, 1-7C-alkyl, 3-7C-cycloalkyl, Ar, Har and Het, wherein each of said 1-7C-alkyl, 3-7C-cycloalkyl, Ar, Har and Het can be unsubstituted or substituted by at least one substituent independently selected from R12;
each R9 is independently selected from the group consisting of: hydrogen, 1-7C-alkyl, and 3-7C-cycloalkyl, wherein each of said 1-7C-alkyl and 3-7C-cycloalkyl can be unsubstituted or substituted by at least one substituent independently selected from R12;
each R10 is independently selected from the group consisting of: hydrogen, 1-7C-alkyl, and 3-7C-cycloalkyl;
R11 is R5;
each R12 is independently selected from R5;
each Ar is independently selected from the group consisting of phenyl and naphthyl;
each Har is the same or different and is independently a fully aromatic or partially aromatic mono- or fused bicyclic ring or ring system, which contains at least one heteroatom in the ring or ring system, made up of
a first constituent being a 5- or 6-membered monocyclic unsaturated, aromatic heteroaryl ring A,
which heteroaryl ring A comprises at least one heteroatom independently selected from the group consisting of nitrogen, oxygen and sulfur,
and, optionally, fused to said first constituent,
a second constituent being a benzene ring, a 5-6C-cycloalkane ring, an additional heteroaryl ring A, or a heterocyclic ring B,
wherein said Har ring or ring system is attached via a substitutable ring carbon or ring nitrogen atom of Har;
each Het is independently a fully saturated or partially unsaturated mono- or fused bicyclic ring or ring system made up of
a first constituent being a 3- or 7-membered monocyclic fully saturated or partially unsaturated, non-aromatic heterocyclic ring B,
which heterocyclic ring B comprises one to three heteroatoms independently selected from the group consisting of nitrogen, oxygen and sulfur, and which heterocyclic ring B is optionally substituted by one or two oxo groups, and, optionally, fused to said first constituent, a second constituent being a benzo group, a 3-7C-cycloalkane group, or an additional heterocyclic ring B, wherein said Het ring or ring system is attached via a substitutable ring carbon or ring nitrogen atom;

or a salt thereof.

2. A compound of formula I as defined in claim 1, wherein

Ra is —C(O)R1, or —C(O)SR2;

Rb is optionally substituted by Rba and/or Rbb and/or Rbc, and is aryl, aryl is phenyl, or naphthyl;

R1 is selected from the group consisting of: hydrogen and 1-4C-alkyl, wherein said 1-4C-alkyl can be unsubstituted or substituted by at least one substituent independently selected from R5;

R2 is selected from the group consisting of: 1-7C-alkyl, 3-7C-cycloalkyl, Ar, Har and Het, wherein each of said 1-7C-alkyl, 3-7C-cycloalkyl, Ar, Har and Het can be unsubstituted or substituted by at least one substituent independently selected from R5;

R5, Rba, Rbb and Rbc may be the same or different and are independently selected from the group consisting of: 1-7C-alkyl, 3-7C-cycloalkyl, Ar, Har, Met, halogen, trifluoromethyl, nitro, cyano, guanidino, amidino, —C(O)R6, —C(O)OR7, —C(O)N(R8)R9, —S(O)$_2$R6, —N(R10)C(O)R6, —N(R10)C(O)OR7, —N(R10)C(O)N(R8)R9, —N(R10)S(O)$_2$R6, —N(R10)S(O)$_2$N(R8)R9, —OC(O)R6, —OC(O)N(R8)R9, —OR7, —N(R8)R(9), and —SR7, wherein each of said 1-7C-alkyl, 3-7C-cycloalkyl, Ar, Har and Het can be unsubstituted or substituted by at least one substituent independently selected from R11;

R6, R7 and R8 may be the same or different and are independently selected from the group consisting of: hydrogen, 1-7C-alkyl, 3-7C-cycloalkyl, Ar, Mar and Met, wherein each of said 1-7C-alkyl, 3-7C-cycloalkyl, Ar, Mar and Het can be unsubstituted or substituted by at least one substituent independently selected from R12;

each R9 is independently selected from the group consisting of: hydrogen, 1-7C-alkyl, and 3-7C-cycloalkyl, wherein each of said 1-7C-alkyl and 3-7C-cycloalkyl can be unsubstituted or substituted by at least one substituent independently selected from R12;

each R10 is independently selected from the group consisting of: hydrogen, 1-7C-alkyl, and 3-7C-cycloalkyl;

R11 is R5;

each R12 is R5;

each Ar is independently selected from the group consisting of phenyl and naphthyl;

each Har is the same or different and is independently a fully aromatic or partially aromatic mono- or fused bicyclic ring or ring system, which contains at least one heteroatom in the ring or ring system, made up of a first constituent being a 5- or 6-membered monocyclic unsaturated, aromatic heteroaryl ring A, which heteroaryl ring A comprises at least one heteroatom independently selected from the group consisting of nitrogen, oxygen and sulfur, and, optionally, fused to said first constituent, a second constituent being a benzene ring, a 5-6C-cycloalkane ring, an additional heteroaryl ring A, or a heterocyclic ring B, wherein said Har ring or ring system is attached via a substitutable ring carbon or ring nitrogen atom of Har;

each Het is independently a fully saturated or partially unsaturated mono- or fused bicyclic ring or ring system made up of a first constituent being a 3- or 7-membered monocyclic fully saturated or partially unsaturated, non-aromatic heterocyclic ring B, which heterocyclic ring B comprises one to three heteroatoms independently selected from the group consisting of nitrogen, oxygen and sulfur, and which heterocyclic ring B is optionally substituted by one or two oxo groups, and, optionally, fused to said first constituent, a second constituent being a benzo group, a 3-7C-cycloalkane group, or an additional heterocyclic ring B, wherein said Het ring or ring system is attached via a substitutable ring carbon or ring nitrogen atom;

or a salt thereof.

3. A compound of formula I as defined in claim 2, wherein

Ra is —C(O)OR2, or a salt thereof.

4. A compound of formula I according to claim 2, in which

Ra is—C(O)R1,

R1 is 1-4C-alkyl, or

R1 is 1-4C-alkyl which is substituted by one R5, or

R1 is 2-4C-alkyl which is substituted by two hydroxyl groups on different carbon atoms, or R1 is 2,2-dimethyl-[1,3]dioxolan-4-yl, or 1-2C-alkyl which is substituted by 2,2-dimethyl-[1,3]dioxolan-4-yl;

or in which

Ra is —C(O)SR2,

R2 is 1-7C-alkyl, or

R2 is 1-7C-alkyl which is substituted by one R5, or

R2 is 3-4C-alkyl which is substituted by two hydroxyl groups on different carbon atoms, or R2 is 1-2C-alkyl which is substituted by 2,2-dimethyl-[1,3]dioxolan-4-yl;

and in which

Rb is substituted by Rba and/or Rbb, and is phenyl, or

Rb is unsubstituted phenyl, or

Rb is unsubstituted naphthyl;

each R5 is independently selected from the group consisting of:

1-4C-alkoxy, 1-4C-alkoxy-2-4C-alkoxy, (1-4C-alkoxy-2-4C-alkoxy)-2-4C-alkoxy, hydroxyl, 1-4C-alkylcarbonyloxy, phenoxy, phenyl-1-4C-alkoxy, 1-4C-alkoxycarbonyl, carboxyl, amino, mono- and di-1-4C-alkylamino, mono- and di-1-4C-alkylaminocarbonyl, carbamoyl, ureido, guanidino, 1-4C-alkylcarbonylamino, Het, Har and phenyl, wherein each of said Har or phenyl radicals alone or part of another group may be unsubstituted or substituted by one or two substituents independently selected from the group consisting of halogen, 1-4C-alkoxy, nitro, trifluoromethyl, 1-4C-alkyl, 1-4C-alkoxycarbonyl and carboxyl, Har is
- a 5-membered monocyclic heteroaryl radical comprising one, two or three nitrogen atoms and/or one heteroatom independently selected from the group consisting of oxygen and sulphur, or
- a 6-membered monocyclic heteroaryl radical comprising one or two nitrogen atoms, or
- a 9-membered fused bicyclic heteroaryl radical comprising one, two or three heteroatoms independently selected from the group consisting of nitrogen, oxygen and sulphur, or
- a 10-membered fused bicyclic heteroaryl radical comprising one, two or three heteroatoms independently selected from the group consisting of nitrogen, oxygen and sulphur, wherein said Har ring or ring system is attached via a ring carbon atom or ring nitrogen atom of Har, Het is morpholino, piperidino, pyrrolidino, 4N-H-piperazino, 4N-(1-4C-alkyl)-piperazino, thiomorpholino, S-oxo-thiomorpholino or S,S-dioxo-thiomorpholino;

Rba is halogen, trifluoromethyl, 1-4C-alkyl, hydroxyl, nitro, phenoxy or 1-4C-alkoxy, Rbb is halogen, trifluoromethyl, 1-4C-alkyl or 1-4C-alkoxy;

or a salt thereof.

5. A compound of formula I according to claim 2, in which
Ra is —C(O)R1,
R1 is 1-4C-alkyl,
or
R1 is 1-4C-alkyl which is mono-substituted by R5,
R5 is 1-4C-alkoxy, 1-4C-alkoxy-2-4C-alkoxy, (1-4C-alkoxy-2-4C-alkoxy)-2-4C-alkoxy, hydroxyl, phenyl-1-4C-alkoxy, phenoxy, pyridyl, pyrimidinyl, pyrazinyl, indolyl, benzofuranyl, benzothiophenyl, thiophenyl, furanyl, thiazolyl, oxazolyl, 1N-(1-4C-alkyl)-imidazolyl, 1N-(1-4C-alkyl)-pyrazolyl, phenyl, 1-4C-alkoxycarbonyl, carboxyl, amino, morpholino, piperidino, pyrrolidino, 4N-(1-4C-alkyl)-piperazino, mono- or di-1-4C-alkylamino, mono- or di-1-4C-alkylaminocarbonyl, carbamoyl, ureido, guanidino, imidazolo, triazolo, pyrazolo, 1-4C-alkylcarbonyl, 1-4C-alkylcarbonyloxy or 1-4C-alkylcarbonylamino,
   wherein each of said pyridyl, pyrimidinyl, pyrazinyl, indolyl, benzofuranyl, benzothiophenyl, thiophenyl, furanyl, thiazolyl, oxazolyl, 1N-(1-4C-alkyl)-imidazolyl, 1N-(1-4C-alkyl)-pyrazolyl, imidazolo, pyrazolo or phenyl radicals alone or part of another group may be unsubstituted or substituted by one or two substituents independently selected from the group consisting of halogen, 1-4C-alkoxy, nitro and 1-4C-alkyl,
or
R1 is 3-4C-alkyl which is substituted by two hydroxyl groups on different carbon atoms,
or
R1 is 1-2C-alkyl which is substituted by 2,2-dimethyl-[1,3]dioxolan-4-yl;
or in which
Ra is —C(O)SR2,
R2 is 1-6C-alkyl,
or
R2 is 1-4C-alkyl which is mono-substituted by R5,
R5 is pyridyl, pyrimidinyl, pyrazinyl, indolyl, benzofuranyl, benzothiophenyl, thiazolyl, oxazolyl, 1N-(1-4C-alkyl)-imidazolyl, 1N-(1-4C-alkyl)-pyrazolyl, phenyl, 1-4C-alkoxycarbonyl, carboxyl, mono- or di-1-4C-alkylaminocarbonyl or carbamoyl,
   wherein each of said pyridyl, pyrimidinyl, pyrazinyl, indolyl, benzofuranyl, benzothiophenyl, thiazolyl, oxazolyl, 1N-(1-4C-alkyl)-imidazolyl, 1N-(1-4C-alkyl)-pyrazolyl or phenyl radicals can be unsubstituted or substituted by one or two substituents independently selected from the group consisting of halogen, 1-4C-alkoxy, nitro and 1-4C-alkyl,
or
R2 is 2-4C-alkyl which is mono-substituted by R5,
R5 is 1-4C-alkoxy, 1-4C-alkoxy-2-4C-alkoxy, (1-4C-alkoxy-2-4C-alkoxy)-2-4C-alkoxy, hydroxyl, phenyl-1-4C-alkoxy, phenoxy, amino, morpholino, piperidino, pyrrolidino, 4N-(1-4C-alkyl)-piperazino, mono- or di-1-4C-alkylamino, ureido, guanidino, imidazolo, triazolo, pyrazolo, 1-4C-alkylcarbonyloxy or 1-4-alkylcarbonylamino,
   wherein each of said imidazolo, pyrazolo or phenyl radicals alone or part of another group can be unsubstituted or substituted by one or two substituents independently selected from the group consisting of halogen, 1-4C-alkoxy, nitro and 1-4C-alkyl;
and in which
Rb is unsubstituted phenyl,
or
Rb is unsubstituted naphthyl,
or
Rb is substituted by Rba and/or Rbb, and is phenyl,
Rba is chlorine, fluorine, bromine, trifluoromethyl, methyl, ethyl, methoxy or ethoxy,
Rbb is chlorine, fluorine, bromine, trifluoromethyl, methyl, ethyl, methoxy or ethoxy,
or a salt thereof.

6. A compound of formula I according to claim 2,
in which
Ra is —C(O)R1,
R1 is methyl, ethyl, propyl or butyl,
or
R1 is methyl which is mono-substituted by R5, ethyl which is mono-substituted by R5, or propyl which is mono-substituted by R5,
R5 is methoxy, ethoxy, 2-methoxyethoxy, 2-(2-methoxyethoxy)-ethoxy, hydroxyl, pyridyl, pyrimidinyl, pyrazinyl, indolyl, thiophenyl, furanyl, thiazolyl, oxazolyl, 1N-methyl-imidazolyl, 1N-methyl-pyrazolyl, phenyl, methoxycarbonyl, ethoxycarbonyl, carboxyl, dimethylaminocarbonyl, morpholino, piperidino, pyrrolidino, 4N-(methyl)-piperazino, carbamoyl, ureido, guanidino, acetyl, imidazolo, triazolo, pyrazolo, ethylcarbonyloxy or methylcarbonyloxy,
or
R1 is propyl or butyl, each of which is substituted by two hydroxyl groups on different carbon atoms,
or
R1 is methyl or ethyl, each of which is substituted by 2,2-dimethyl-[1,3]dioxolan-4-yl;
or in which
Ra is —C(O)SR2,
R2 is methyl, ethyl, propyl, butyl or pentyl,
or
R2 is methyl which is mono-substituted by R5, ethyl which is mono-substituted by R5, or propyl which is mono-substituted by R5,
R5 is pyridyl, or R2 is ethyl which is mono-substituted by R5, or propyl which is mono-substituted by R5, R5 is hydroxyl, methoxy or ethoxy;

and in which

R5 is unsubstituted phenyl, or

Rb is substituted by Rba and/or Rbb, and is phenyl,

Rba is chlorine, methyl, methoxy or ethoxy,

Rbb is chlorine, methyl, methoxy or ethoxy, or a salt thereof.

7. A compound of formula I according to claim 2, in which

Ra is—C(O)R1,

R1 is methyl, ethyl or propyl, or

R1 is (R5)-methyl, 2-(R5)-ethyl, or 3-(R5)-propyl,

R5 is methoxy, ethoxy, 2-methoxyethoxy, 2-(2-methoxyethoxy)-ethoxy, hydroxyl, pyridyl, pyrimidinyl, pyrazinyl, imidazolo, pyrazolo or methylcarbonyloxy, or R1 is 2,3-dihydroxy-propyl;

or in which

Ra is —C(O)SR2,

R2 is methyl, ethyl or propyl, or

R2 is (R5)-methyl, 2-(R5)-ethyl, or 3-(R5)-propyl,

R5 is pyridyl, or

R2 is 2-(R5)-ethyl, or 3-(R5)-propyl,

R5 is hydroxyl;

and in which

Rb is unsubstituted phenyl, or

Rb is substituted by Rba and/or Rbb, and is phenyl,

Rba is attached in the meta position with respect to the binding position in which said phenyl ring is bonded to the adjacent carbonyl group, and is methoxy or ethoxy, Rbb is attached in the meta or para position with respect to the binding position in which said phenyl ring is bonded to the adjacent carbonyl group, and is methoxy or ethoxy, or a salt thereof.

8. A compound of formula I according to claim 2, in which

Ra is—C(O)R1,

R1 is (R5)-methyl, or 2-(R5)-ethyl,

R5 is methoxy, 2-methoxyethoxy, hydroxyl or pyridyl, or

R1 is 2,3-dihydroxy-propyl;

or in which

Ra is —C(O)SR2,

R2 is ethyl, or

R2 is (R5)-methyl, or 2-(R5)-ethyl,

R5 is pyridyl, or

R2 is 2-(R5)-ethyl,

R5 is hydroxyl;

and in which

Rb is 3-methoxy-phenyl or 3,5-dimethoxy-phenyl;

or a salt thereof.

9. A compound of formula I according to claim 3, in which

Ra is —C(O)OR2,

R2 is 1-7C-alkyl, 3-7C-cycloalkyl, phenyl, pyridyl, or phenyl mono-substituted by 1-4C-alkoxy or 1-4C-alkoxycarbonyl, or R2 is 1-7C-alkyl which is substituted by one R5, or R2 is 3-4C-alkyl which is substituted by two hydroxyl groups on different carbon atoms, or R2 is 1-2C-alkyl which is substituted by 2,2-dimethyl-[1,3]dioxolan-4-yl;

and in which

Rb is substituted by Rba and/or Rbb, and is phenyl, or

Rb is unsubstituted phenyl, or

Rb is unsubstituted naphthyl;

each R5 is independently selected from the group consisting of:

1-4C-alkoxy, 1-4C-alkoxy-2-4C-alkoxy, (1-4C-alkoxy-2-4C-alkoxy)-2-4C-alkoxy, hydroxyl, 1-4C-alkylcarbonyloxy, phenoxy, phenyl-1-4C-alkoxy, 1-4C-alkoxycarbonyl, carboxyl, amino, mono- and di-1-4C-alkylamino, mono- and di-1-4C-alkylaminocarbonyl, carbamoyl, ureido, guanidino, 1-4C-alkylcarbonylamino, Het, Har and phenyl, wherein each of said Har or phenyl radicals alone or part of another group may be unsubstituted or substituted by one or two substituents independently selected from the group consisting of halogen, 1-4C-alkoxy, nitro, trifluoromethyl, 1-4C-alkyl, 1-4C-alkoxycarbonyl and carboxyl, Har is a 5-membered monocyclic heteroaryl radical comprising one, two or three nitrogen atoms and/or one heteroatom independently selected from the group consisting of oxygen and sulphur, or a 6-membered monocyclic heteroaryl radical comprising one or two nitrogen atoms, or a 9-membered fused bicyclic heteroaryl radical comprising one, two or three heteroatoms independently selected from the group consisting of nitrogen, oxygen and sulphur, or a 10-membered fused bicyclic heteroaryl radical comprising one, two or three heteroatoms independently selected from the group consisting of nitrogen, oxygen and sulphur, wherein said Har ring or ring system is attached via a ring carbon atom or ring nitrogen atom of Har, Het is morpholino, piperidino, pyrrolidino, 4N-H-piperazino, 4N-(1-4C-alkyl)-piperazino, thiomorpholino, S-oxo-thiomorpholino or S,S-dioxo-thiomorpholino;

Rba is halogen, trifluoromethyl, 1-4C-alkyl, hydroxyl, nitro, phenoxy or 1-4C-alkoxy, and Rbb is halogen, trifluoromethyl, 1-4C-alkyl or 1-4C-alkoxy;

or a salt thereof.

10. A compound of formula I according to claim 3, in which

Ra is —C(O)OR2,

R2 is 1-6C-alkyl, or

R2 is phenyl, pyridyl, or phenyl mono-substituted by 1-4C-alkoxy or 1-4-alkoxycarbonyl, or R2 is 1-4C-alkyl which is mono-substituted by R5, R5 is pyridyl, pyrimidinyl, pyrazinyl, indolyl, benzofuranyl, benzothiophenyl, thiazolyl, oxazolyl, 1N-(1-4C-alkyl)-imidazolyl, 1N-(1-4C-alkyl)-pyrazolyl, phenyl, 1-4C-alkoxycarbonyl, carboxyl, mono- or di-1-4C-alkylaminocarbonyl or carbamoyl, wherein each of said pyridyl, pyrimidinyl, pyrazinyl, indolyl, benzofuranyl, benzothiophenyl, thiazolyl, oxazolyl, 1N-(1-4C-alkyl)-imidazolyl, 1N-(1-4C-alkyl)-pyrazolyl or phenyl radicals can be unsubstituted or substituted by one or two substituents independently selected from the group consisting of halogen, 1-4C-alkoxy, nitro and 1-4C-alkyl, or R2 is 2-4C-alkyl which is mono-substituted by R5, R5 is 1-4C-alkoxy, 1-4C-alkoxy-2-4C-alkoxy, (1-4C-alkoxy-2-4C-alkoxy)-2-4C-alkoxy, hydroxyl, phenyl-1-4C-alkoxy, phenoxy, amino, morpholino, piperidino, pyrrolidino, 4N-(1-4C-alkyl)-piperazino, mono- or di-1-4C-alkylamino, ureido, guanidino, imidazolo, triazolo, pyrazolo, 1-4C-alkylcarbonyloxy or 1-4C-alkyl-carbonylamino, wherein each of said imidazolo, pyrazolo or phenyl radicals alone or part of another group can be unsubstituted or substituted by one or two substituents independently selected from the group consisting of halogen, 1-4C-alkoxy, nitro and 1-4C-alkyl, or R2 is 3-4C-alkyl which is substituted by two hydroxyl groups on different carbon atoms, or R2 is 1-2C-alkyl which is substituted by 2,2-dimethyl-[1,3]dioxolan-4-yl;

and in which

Rb is unsubstituted phenyl, or

Rb is unsubstituted naphthyl, or

Rb is substituted by Rba and/or Rbb, and is phenyl,

Rba is chlorine, fluorine, bromine, trifluoromethyl, methyl, ethyl, methoxy or ethoxy, and Rbb is chlorine, fluorine, bromine, trifluoromethyl, methyl, ethyl, methoxy or ethoxy, or a salt thereof.

11. A compound of formula I according to claim 3, in which

Ra is —C(O)OR2,

R2 is methyl, ethyl, propyl or butyl, or

R2 is phenyl, pyridyl, (1-2C-alkoxycarbonyl)-phenyl, or (1-2C-alkoxy)-phenyl, or R2 is methyl which is mono-substituted by R5, ethyl which is mono-substituted by R5, or propyl which is mono-substituted by R5, R5 is pyridyl, pyrim idinyl, pyrazinyl, 1N-methyl-imidazolyl, 1N-methyl-pyrazolyl, (methyl)-thiazolyl, phenyl, (1-2C-alkoxy)-phenyl, methoxycarbonyl, ethoxycarbonyl, carboxyl, di-methylaminocarbonyl or carbamoyl, or R2 is ethyl which is mono-substituted by R5, or propyl which is mono-substituted by R5, R5 is methoxy, ethoxy, 2-methoxyethoxy, 2-(2-methoxyethoxy)-ethoxy, hydroxyl, benzyloxy, phenoxy, morpholino, piperidino, pyrrolidino, 4N-(methyl)-piperazino, dimethylamino, imidazolo, triazolo, pyrazolo, methylcarbonyloxy, ethylcarbonyloxy, methylcarbonylamino or ethylcarbonylamino, or R2 is propyl or butyl, each of which is substituted by two hydroxyl groups on different carbon atoms, or R2 is methyl or ethyl, each of which is substituted by 2,2-dimethyl-[1,3]dioxolan-4-yl;

and in which

Rb is unsubstituted phenyl, or

Rb is substituted by Rba and/or Rbb, and is phenyl,

Rba is chlorine, methyl, methoxy or ethoxy, and

Rbb is chlorine, methyl, methoxy or ethoxy, or a salt thereof.

12. A compound of formula I according to claim 3, in which

Ra is —C(O)OR2,

R2 is methyl, ethyl or propyl, or

R2 is (R5)-methyl, 2-(R5)-ethyl, or 3-(R5)-propyl,

R5 is pyridyl, pyrazinyl or pyrimidinyl, or

R2 is 2-(R5)-ethyl, or 3-(R5)-propyl,

R5 is methoxy, ethoxy, 2-methoxyethoxy, 2-(2-methoxyethoxy)-ethoxy, hydroxyl, imidazolo, pyrazolo or methylcarbonyloxy, or R2 is 2,3-dihydroxy-propyl;

and in which

Rb is unsubstituted phenyl, or

Rb is substituted by Rba and/or Rbb, and is phenyl,

Rba is attached in the meta position with respect to the binding position in which said phenyl ring is bonded to the adjacent carbonyl group, and is methoxy or ethoxy, and Rbb is attached in the meta or para position with respect to the binding position in which said phenyl ring is bonded to the adjacent carbonyl group, and is methoxy or ethoxy, or a salt thereof.

13. A compound of formula I according to claim 3, in which

Ra is —C(O)OR2,

R2 is ethyl, or

R2 is (R5)-methyl, or 2-(R5)-ethyl,

R5 is pyridyl, or

R2 is 2-(R5)-ethyl,

R5 is methoxy, 2-methoxyethoxy or hydroxyl, or

R2 is 2,3-dihydroxy-propyl;

and in which

Rb is 3-methoxy-phenyl or 3,5-dimethoxy-phenyl;

or a salt thereof.

14. A compound of formula I according to claim 2, in which

Rb is selected from the group consisting of 3-chloro-phenyl, 4-chloro-phenyl, 2-methyl-phenyl, 3-methyl-phenyl, 4-methyl-phenyl, 3-methoxy-phenyl, 4-methoxy-phenyl and 3,5-dimethoxy-phenyl;

or a salt thereof.

15. A compound of formula I according to claim 2, in which,
Ra is—C(O)R1,
R1 is 1-4C-alkyl;
or in which,
Ra is-C(O)R1,
R1 is 1-4C-alkyl, which is substituted by R5,
R5 is selected from the group consisting of: hydroxyl, pyridinyl, —C(O)OR7, methoxy, ethoxy, 2-methoxy-ethoxy, and 2-(2-methoxy-ethoxy)-ethoxy,
R6 is methyl or ethyl,
R7 is selected from the group consisting of: hydrogen, methyl and ethyl,
or in which,
Ra is —C(O)SR2,
R2 is 1-4C-alkyl;
and
in which,
Rb is unsubstituted phenyl;
or in which,
Rb is substituted by Rba and/or Rbb, and is phenyl,
Rba is attached in the mete position with respect to the binding position in which said phenyl ring is bonded to the adjacent carbonyl group, and is 1-2C-alkoxy, and
Rbb is attached in the meta or para position with respect to the binding position in which said phenyl ring is bonded to the adjacent carbonyl group, and is 1-2C-alkoxy,
or a salt thereof.

16. A compound of formula I according to claim 1, in which
Ra is —C(O)R1,
R1 is 1-7C-alkyl, or 1-4C-alkyl substituted by R5,
R5 is 1-4C-alkoxycarbonyl, 1-4C-alkylcarbonyl, carbamoyl, 1-4C-alkoxy, or Har,
Har is optionally substituted by R11 and is a 5- or 6-membered monocyclic unsaturated, aromatic heteroaryl radical comprising at least one heteroatom independently selected from the group consisting of nitrogen, oxygen and sulphur, which is optionally fused to a benzene ring,
R11 is 1-4C-alkyl;
or
Ra is —C(O)OR2,
R2 is 1-7C-alkyl, or 2-4C-alkyl substituted by R5,
R5 is 1-4C-alkoxy, or Har,
Har is optionally substituted by R11, and is a 5- or 6-membered monocyclic unsaturated, aromatic heteroaryl radical comprising at least one heteroatom independently selected from the group consisting of nitrogen, oxygen and sulphur, which is optionally fused to a benzene ring,
R11 is 1-4C-alkyl;
or
Ra is —C(O)SR2,
R2 is 1-7C-alkyl;
and
Rb is substituted by Rba and/or Rbb, and is phenyl,
Rba is attached in the meta position with respect to the binding position in which said phenyl ring is bonded to the adjacent carbonyl group, and is halogen, trifluoromethyl, 1-4C-alkyl, 1-4C-alkoxy, or phenoxy, and
Rbb is attached in the meta or para position with respect to the binding position in which said phenyl ring is bonded to the adjacent carbonyl group, and is trifluoromethyl, 1-4C-alkyl, or 1-4C-alkoxy,
or a salt thereof.

17. A pharmaceutical composition comprising one or more compounds of formula I according to claim 1 or a pharmaceutically acceptable salt thereof, together with a pharmaceutically acceptable excipient and/or vehicle.

18. A pharmaceutical composition comprising one or more compounds of formula I according to claim 2 or a pharmaceutically acceptable salt thereof, together with a pharmaceutically acceptable excipient and/or vehicle.

19. A compound of formula I as defined in claim 1, wherein
Ra is —C(O)R1, —C(O)SR2, —C(O)N(R3)R4, —S(O)$_2$R1, or —S(O)$_2$N(R3)R4.

20. A compound of formula I as defined in claim 1, wherein
Ra is —C(O)R1, —C(O)SR2, —C(O)N(R3)R4, or —S(O)$_2$ N(R3)R4.

21. A compound of formula I as defined in claim 1, wherein
aryl is phenyl.

22. A compound of formula I as defined in claim 1, wherein
aryl is naphthyl.

23. A compound of formula I as defined in claim 19, wherein
aryl is naphthyl.

24. A compound of formula I as defined in claim 1, wherein
Rb is substituted by Rba and/or Rbb and/or Rbc.

* * * * *

UNITED STATES PATENT AND TRADEMARK OFFICE
CERTIFICATE OF CORRECTION

PATENT NO.        : 7,714,134 B2
APPLICATION NO.   : 11/628369
DATED             : May 11, 2010
INVENTOR(S)       : Klaus Pekari Page 1 of 1

It is certified that error appears in the above-identified patent and that said Letters Patent is hereby corrected as shown below:

Column 117, line 26 reads: "1-7C-alkyl, 3-7C-cycloalkyl, AR, Har, Met, Halogen, tri-"

Should read: -- 1-7C-alkyl, 3-7C-cycloalkyl, AR, Har, Het, Halogen, tri- --

Column 117, line 38 reads: "hydrogen, 1-7C-alkyl, 3-7C-cycloalkyl, AR, Mar and"

Should read: -- hydrogen, 1-7C-alkyl, 3-7C-cycloalkyl, AR, Har and --

Column 117, line 39 reads: "Met, wherein each of said 1-7C-alkyl, 3-7C-cycloalkyl,"

Should read: -- Het, wherein each of said 1-7C-alkyl, 3-7C-cycloalkyl, --

Column 117, line 40 reads: "Ar, Mar and Het can be unsubstituted or substituted by at"

Should read: -- Ar, Har and Het can be unsubstituted or substituted by at --

Signed and Sealed this
Eighth Day of February, 2011

David J. Kappos
*Director of the United States Patent and Trademark Office*